US007741306B2

(12) United States Patent
Slack et al.

(10) Patent No.: US 7,741,306 B2
(45) Date of Patent: Jun. 22, 2010

(54) REGULATION OF ONCOGENES BY MICRORNAS

(75) Inventors: Frank J. Slack, Guilford, CT (US); Steven M. Johnson, Redwood City, CA (US); Helge Grosshans, Basel (CH); Joanne Barnes Weidhaas, Westport, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 11/876,503

(22) Filed: Oct. 22, 2007

(65) Prior Publication Data

US 2008/0119436 A1 May 22, 2008

Related U.S. Application Data

(63) Continuation-in-part of application No. 11/219,379, filed on Sep. 2, 2005.

(60) Provisional application No. 60/606,855, filed on Sep. 2, 2004, provisional application No. 60/853,061, filed on Oct. 20, 2006, provisional application No. 60/931,740, filed on May 25, 2007.

(51) Int. Cl.
*A01N 43/04* (2006.01)
*C12Q 1/68* (2006.01)
*C19P 19/34* (2006.01)
*C07H 21/04* (2006.01)

(52) U.S. Cl. .......................... 514/44; 435/6; 435/91.1; 435/91.31; 435/455; 536/23.1; 536/24.31; 536/24.5

(58) Field of Classification Search .................. 435/6, 435/91.1, 91.31, 375, 455; 514/1, 2, 44; 536/23.1, 24.5, 24.31
See application file for complete search history.

(56) References Cited

U.S. PATENT DOCUMENTS

| 3,832,253 A | 8/1974 | Di Palma et al. |
| 3,854,480 A | 12/1974 | Zaffaroni |
| 4,452,775 A | 6/1984 | Kent |
| 4,667,013 A | 5/1987 | Reichle |
| 4,675,189 A | 6/1987 | Kent et al. |
| 4,748,034 A | 5/1988 | de Rham |
| 5,075,109 A | 12/1991 | Tice et al. |
| 5,133,974 A | 7/1992 | Paradissis et al. |
| 5,223,618 A | 6/1993 | Cook et al. |
| 5,239,660 A | 8/1993 | Ooi |
| 5,272,071 A | 12/1993 | Chappel |
| 5,378,825 A | 1/1995 | Cook et al. |
| 5,407,686 A | 4/1995 | Patel et al. |
| 5,466,786 A | 11/1995 | Buhr et al. |
| 5,489,743 A | 2/1996 | Robinson et al. |
| 5,578,461 A | 11/1996 | Sherwin et al. |
| 5,602,240 A | 2/1997 | De Mesmaeker et al. |
| 5,610,289 A | 3/1997 | Cook et al. |
| 5,614,617 A | 3/1997 | Cook et al. |
| 5,672,697 A | 9/1997 | Buhr et al. |
| 5,705,629 A | 1/1998 | Bhongle |
| 5,714,606 A | 2/1998 | Acevedo et al. |
| 5,736,152 A | 4/1998 | Dunn |
| 5,777,092 A | 7/1998 | Cook et al. |
| 5,858,988 A | 1/1999 | Wang |
| 6,919,208 B2 | 7/2005 | Levy et al. |
| 2005/0227256 A1* | 10/2005 | Hutvagner et al. ............. 435/6 |
| 2006/0141600 A1* | 6/2006 | Joshua-Tor et al. ......... 435/199 |
| 2008/0182245 A1* | 7/2008 | Brown et al. .................. 435/6 |

FOREIGN PATENT DOCUMENTS

| WO | WO 84/03564 | 9/1984 |
| WO | WO 91/06667 | 5/1991 |
| WO | WO 91/09955 | 7/1991 |
| WO | WO 92/20808 | 11/1992 |
| WO | WO 93/09222 | 5/1993 |
| WO | WO 94/12650 | 6/1994 |
| WO | WO 94/28122 | 12/1994 |
| WO | WO 2004/076622 | * 9/2004 |

OTHER PUBLICATIONS

Crooke, S.T., Annu. Rev. Med., vol. 55, pp. 61-95 (2004).*
Peracchi, A. et al., Rev. Med. Virol., vol. 14, pp. 47-64 (2004).*
Chirila, T. et al., Biomaterials, vol. 23, pp. 321-342 (2002).*
Agrawal, S. et al., Molecular Med. Today, vol. 6, pp. 72-81 (2000).*
Opalinska, J.B. et al., Nature Reviews, vol. 1, pp. 503-514 (2002).*
Branch, A. Trends, in Biochem. Sci., vol. 23, pp. 45-50 (1998).*
Agrawal, et al., "Antisense therapeutics: is it as simple as complementary base recognition?", *Molecular Med. Today*, 6(2):72-81 (2000).
Branch, "A good antisense molecule is hard to find", *Trends in Biochem. Sci.*, 23(2):45-50 (1998).
Chirila, "The use of synthetic polymers for delivery of therapeutic antisense oligodeoxynucleotides", *Biomaterials*, 23(2):321-342 (2002).
Crooke, "Antisense Research and Application", Chapter 1, pp. 1-50 (Ed. By S. Crooke). Springer-Verlag (1998).

(Continued)

*Primary Examiner*—Jane Zara
(74) *Attorney, Agent, or Firm*—Mintz Levin Cohn Ferris Glovsky and Popeo, P.C.; Ivor R. Elrifi, Esq.; Katherine J. Miller

(57) ABSTRACT

Naturally occurring miRNAs that regulate human oncogenes and methods of use thereof are described. Suitable nucleic acids for use in the methods and compositions described herein include, but are not limited to, pri-miRNA, pre-miRNA, mature miRNA, or fragments of variants thereof that retain the biological activity of the mature miRNA and DNA encoding a pri-miRNA, pre-miRNA, mature miRNA, fragments or variants thereof, or regulatory elements of the miRNA. The compositions are administered to a subject prior to administration of a cytotoxic therapy in an amount effective to sensitize cells or tissues to be treated to the effects of the cytotoxic therapy.

11 Claims, 34 Drawing Sheets

OTHER PUBLICATIONS

Opalinska, "Nucleic-acid therapeutics: basic principles and recent applications", *Nature Rev. Drug Discov.*, 1(7):503-514 (2002).

Peracchi, "Prospects for antiviral ribozymes and deoxyribozymes", *Rev. Med. Virol.*, 14(1):47-64 (2004).

Abrahante, et al., "The *Caenorhabditis elegans* hunchback-like gene lin-57/hbl-1 controls developmental time and is regulated by microRNAs", *Dev Cell*, 4(5):625-637 (2003).

Ahrendt, et al., "Cigarette smoking is strongly associated with mutation of the K-ras gene in patients with primary adenocarcinoma of the lung", *Cancer*, 92:1525-1530 (2001).

Akao, et al., "let-7 microRNA functions as a potential growth suppressor in human colon cancer cells", *Biol. Pharm. Bull.*, 29(5):903-6 (2006).

Ambros, "Cell cycle-dependent sequencing of cell fate decisions in *Caenorhabditis elegans* vulva precursor cells", *Development*, 126:1947-1956 (1999).

Ambros and Horvitz, "Heterochronic mutants of the nematode *Caenorhabditis elegans*", *Science*, 226:409-416 (1984).

Antebi, "The tick-tock of aging?", Science, 310:1911-1913 (2005).

Baker and Sanger, "The density of clonogenic cells in human solid tumors", *Int. J. Cell Cloning*, 9(2):155-65 (1991).

Banerjee and Slack, "Control of developmental timing by small temporal RNAs: a paradigm for RNA-mediated regulation of gene expression", *Bioessays*, 24(2):119-29 (2002).

Bartel, "MicroRNAs: Genomics, Biogenesis, Mechanism, and Function", *Cell*, 116(2):281-97 (2004).

Beitel, et al., "*Caenorhabditis elegans* ras gene let-60 acts as a switch in the pathway of vulval induction", *Nature*, 348(6301):503-509 (1990).

Berset, et al., "Notch inhibition of RAS signaling through MAP kinase phosphatase LIP-1 during *C. elegans* vulval development", *Science*, 291:1055-1058 (2001).

Boehm and Slack, "A developmental timing microRNA and its target regulate life span in *C. elegans*", *Science*, 310:1954-1957 (2005).

Brennecke, et al., "Bantam encodes a developmentally regulated microRNA that controls cell proliferation and regulates the proapoptotic gene hid in *Drosophila*", *Cell*, 113(1):25-36 (2003).

Brenner, "The genetics of *Caenorhabditis elegans*", *Genetics*, 77(1):71-94 (1974).

Brown and Wilson, "Apoptosis genes and resistance to cancer therapy: what does the experimental and clinical data tell us?", *Cancer Biol. Ther.*, 2(5):477-90 (2003).

Brummelkamp, et al., "Stable suppression of tumorigenicity by virus-mediated RNA interference", *Cancer Cell*, 2(3):243-7 (2002).

Calin, et al., "Human microRNA gene are frequently located at fragile sites and genomic regions involved in cancers", *Proc Natl Acad Sci U S A*, 101:2999-3004 (2004).

Calin, et al., "Frequent deletions and doenregulation of microRNA genes *miR*15 and *miR*16 at 13q14 in chronic lymphocytic leukemia", *Proc Natl Acad Sci U S A*, 99(24):15524-9 (2002).

Capecchi, "Altering the genome by homologous recombination", *Science*, 244:1288-1292 (1989).

Carmell, et al., "The Argonaute family: tentacles that reach into RNAi, developmental control, stem cell maintenance, and tumorigenesis", *Genes Dev.*, 16(21):2733-42 (2002).

Caudy, et al., "A micrococcal nuclease homologue in RNAi effector complexes", *Nature*, 425(6956):411-4 (2003).

Ceol and Horvitz, "A new class of *C. elegans* synMuv genes implicates a Tip60/NuA4-like HAT complex as a negative regulator of Ras signaling", *Dev Cell*, 6:563-576 (2004).

Chang, et al., "MicroRNAs act sequentially and asymmetrically to control chemosensory laterality in the nematode", *Nature*, 430(7001):785-9 (2004).

Chen, et al., "The developmental miRNA profiles of zebrafish as determined by small RNA cloning", *Genes Dev.*, 19(11):1288-93 (2005).

Chen, et al., "MicroRNAs Modulate HematopoieticLineage Differentiation", *Science*, 303(5654):83-6 (2004).

Dent and Han, "Post-embryonic expression pattern of *C. elegans* let-60 ras reporter constructs", *Mech Dev*, 72:179-182 (1998).

Duursma and Agami, "Ras interference as cancer therapy", *Semin. Cancer Biol.*, 13(4):267-73 (2003).

Eisenmann and Kim, "Mechanism of activation of the *Caenorhabditis elegans* ras homologue let-60 by a novel, temperature-sensitive, gain-of-function mutation", *Genetics*, 146:553-565 (1997).

Esquela-Kerscher, et al., "Post-embryonic expression of *C. elegans* microRNAs belonging to the lin-4 and let-7 families in the hypodermis and the reproductive system", *Dev. Dyn.*, 234(4):868-77 (2005).

Feinbaum and Ambros, "The timing of lin-4 RNA accumulation controls the timing of postembryonic developmental events in *Caenorhabditis elegans*", *Dev Biol*, 210(1):87-95 (1999).

Freemont, "The Ring finger. A novel protein sequence motif related to the zinc finger", *Ann. New York. Acad. Sci.*, 684:174-192 (1993).

Garigan, et al., "Genetic analysis of tissue aging in *Caenorhabditis elegans*: a role for heat-shock factor and bacterial proliferation", *Genetics*, 161(3), 1101-12 (2002).

Gauwerky, et al., "Activation of MYC in a masked t(8;17) translocation results in an aggressive B-cell leukemia", *Proc Natl Acad Sci U S A*, 86(22):8867-71 (1989).

Giovanella, et al., Heterotransplantation of human malignant tumors in "nude" thymusless mice. II. Malignant tumors induced by injection of cell cultures derived from human solid tumors, *J. Natl. Can. Inst.*, 52:921-30 (1974).

Grishok, at al., "Genes and mechanisms related to RNA interference regulate expression of the small temporal RNAs that control *C. elegans* developmental timing", *Cell*, 106(1):23-34 (2001).

Groβshans, et al., "The temporal patterning microRNA let-7 regulates several transcription factors at the larval to adult transition in *C. elegans*", *Dev Cell*, 8(3):321-30 (2005).

Haasch, et al., "T cell activation induces a noncoding RNA transcript sensitive to inhibition by immunosuppressant drugs and encoded by the proto-oncogene, BIC", *Cell Immunol*, 217(1-2):78-86 (2002).

Hamilton and Baulcombe, "A species of small antisense RNA in posttranscriptional gene silencing in plants", *Science*, 286(5441):950-2 (1999).

Han and Sternberg, "let-60, a gene that specifies cell fates during *C. elegans* vulval induction, encodes a ras protein", *Cell*, 63:921-931 (1990).

Han, et al., "The let-60 locus controls the switch between vulval and nonvulval cell fates in *Caenorhabditis elegans*", *Genetics*, 126:899-913 (1990).

Hasegawa, et al., "Ring finger motif regulates transforming activity of the rfp/ret fusion gene", *Biochem Biophys Res Commun*, 225(2):627-31 (1996).

He, et al., "A microRNA polycistron as a potential human oncogene", *Nature*, 435(7043):828-33 (2005).

Hewitt and Wilson, "Further studies relating to the implications of radiation survival curve data for treatment of CBA mouse leukaemia by whole-body irradiation", *Br. J. Cancer*, 14:186-94 (1960).

Hopper, et al., "ARK-1 inhibits EGFR signaling in *C. elegans*", *Mol Cell*, 6:65-75 (2000).

Hsu, et al., "Regulation of aging and age-related disease by DAF-16 and heat-shock factor", *Science*, 300(5622):1142-5 (2003).

Huang, et al., "Functional silencing of hepatic microsomal glucose-6-phosphate gene expression in vivo by adenovirus-mediated delivery of short hairpin RNA", *FEBS Lett.*, 558(1-3):69-73 (2004).

Hutvagner and Zamore, "A microRNA in a multiple-turnover RNAi enzyme complex", *Science*, 297(5589):2056-60 (2002).

Hutvagner, et al., "Sequence-specific inhibition of small RNA function", *PLoS Biol*, 2(4):04 65-0475 (2004).

Hutvagner, et al., "A cellular function for the RNA-interference enzyme Dicer in the maturation of the let-7 small temporal RNA", *Science*, 293(5531):834-8 (2001).

Johnson, et al., "RAS Is Regulated by the *let-7* MicroRNA Family", *Cell*, 120(5):635-47 (2005).

Johnson, et al., "The time of appearance of the *C. elegans* let-7 microRNA is transcriptionally controlled utilizing a temporal regulatory element in its promoter", *Dev Biol*, 259:364-379 (2003).

Johnson, et al., "Somatic activation of the *K-ras* oncogene causes early onset lung cancer in mice", *Nature*, 410:1111-1116 (2001).

Johnston and Hobert, "A microRNA controlling left/right neuronal asymmetry in *Caenorhabditis elegans*", *Nature*, 426(6968):845-9 (2003).

Kakizuka, et al., "Chromosomal translocation t(15;17) in human acute promyelocytic leukemia fuses RAR alpha with a novel putative transcription factor, PML", *Cell*, 66:663-674 (1991).

Karube, et al., "Reduced expression of Dicer associated with poor prognosis in lung cancer patients", *Cancer Sci*, 96(2):111-5 (2005).

Katz, et al, "Different levels of the *C. elegans* growth factor LIN-3 promote distinct vulval precursor fates", *Cell*, 82:297-307 (1995).

Kawasaki and Taira, "Short hairpin type of dsRNAs that are controlled by tRNA(Val) promoter significantly induce RNAi-mediated gene silencing in the cytoplasm of human cells", *Nucleic Acids Res.*, 31(2):700-7 (2003).

Kenyon, et al., "A *C. elegans* mutant that lives twice as long as wild type", *Nature*, 366(6454):461-4(1993).

Lagos-Quintana, et al., "New microRNAs from mouse and human", *RNA*, 9(2):175-179 (2003).

Lagos-Quintana, et al., "Identification of tissue-specific microRNAs from mouse", *Curr Biol*, 12(9):735-9 (2002).

Lagos-Quintana, et al., "Identification of novel genes coding for small expressed RNAs", *Science*, 294(5543):853-8 (2001).

Lai, et al., "Pervasive regulation of *Drosophila* Notch target genes by GY-box-, Brd-box-, and K-box-class microRNAs", *Genes Dev.*, 19(9):1067-80 (2005).

Lau, et al., "An abundant class of tiny RNAs with probable regulatory roles in *Caenorhabditis elegans*", *Science*, 294(5543):858-62 (2001).

Le Douarin, et al., "The N-terminal part of TIF1, a putative mediator of the ligand-dependent activation function (AF-2) of nuclear receptors, is fused to B-raf in the oncogenic protein T18", *EMBO J.*, 14(9):2020-2033 (1995).

Lecellier, et al., "A cellular microRNA mediates antiviral defense in human cells", *Science*, 308(5721):557-60 (2005).

Lee and Ambros, "An extensive class of small RNAs in *Caenorhabditis elegans*", *Science*, 294(5543):862-4 (2001).

Lee, et al., "The nuclear RNase III Drosha initiates microRNA processing", *Nature*, 425(6956):415-9 (2003).

Lee, et al., "unc-101, a gene required for many aspects of *Caenorhabditis elegens* development and behavior, encodes a clathrin-associated protein", *Genes Dev.*, 8:60-73 (1994).

Lee, et al., "The *C. elegans* heterochronic gene lin-4 encodes small RNAs with antisense complementarity to lin-14", *Cell*, 75(5):843-854 (1993).

Lee, et al., "Depletion of human micro-RNA miR-125b reveals that it is critical for the proliferation of differentiated cells but not for the down-regulation of putative targets during differentiation", *Jour. Biol. Chem.*, 280(17):16635-16641 (2005).

Li, et al., "A modified Boyden Chamber assay for tumor cell transendothelial migration in vitro", *Clin. Exp. Metastasis*, 17:423-9 (1999).

Li, et al., "Expression of the putative proto-oncogene His-1 in normal and neoplastic tissues", *Am J Pathol*, 150:1297-305 (1997).

Lim, et al., "The microRNAs of *Caenorhabditis elegans*", *Genes Dev.*, 17(8):991-1008 (2003).

Lin, et al., "Regulation of the *Caenorhabitits elegans* longevity protein DAF-16 by insulin/IGF-1 and germline signaling", *Nature Genetics*, 28:139-145 (2001).

Lin, et al., "The *C. elegans* hunchback homolog, hbl-1, controls temporal patterning and is a probable microRNA target", *Dev Cell*, 4(5):639-50 (2003).

Liu, et al., "Regulation of signaling genes by TGFbeta during entry into dauer diapause in *C. elegans*", *BMC Developmental Biology*, 4:11 (2004).

Lorenz, et al., "Steroid and lipid conjugates of siRNAs to enhance cellular uptake and gene silencing in liver cells", *Bioorg. Med. Chem. Lett.*, 14(19):4975-4977 (2004).

Lu, et al., "Gene regulation and DNA damage in the ageing human brain", *Nature*, 429(6994), 883-91 (2004).

Lu, et al., "MicroRNA expression profiles classify human cancers", *Nature*, 435(7043):834-838 (2005).

Ma, et al., "Nuclease-resistant external guide sequence-induced cleavage of target RNA by human ribonuclease P", *Antisense Nucleic Acid Drug Dev.*, 8:415-426 (1998).

Malumbres, et al., "RAS oncogenes: the first 30 years", *Nat Rev Cancer*, 3(6):459-65 (2003).

McCarroll, et al., "Comparing genomic expression patterns across species identifies shared transcriptional profile in aging", *Nat. Genet.*, 36(2):197-204 (2004).

McKay, et al., "Transformation and stimulation of DNA synthesis in NIH-3T3 cells are a titratable function of normal p21N-ras expression", *EMBO J*, 5:2617-2621 (1986).

McManus, "MicroRNAs and cancer", *Seminars in Cancer Biology*, 13:253-258 (2003).

Meister, et al., "Sequence-specific inhibition of microRNA- and siRNA-induced RNA silencing", *RNA*, 10:544-550 (2004).

Meng, et al., "Automated docking with grid-based energy evaluation", *J. Comp. Chem.*, 13:505-524 (1992).

Michael, et al., "Reduced accumulation of specific microRNAs in colorectal neoplasia", *Mol Cancer Res*, 1(12):882-91 (2003).

Moss, et al., "The Cold Shock Domain Protein LIN-28 Controls Developmental Timing in *C. elegans* and Is Regulated by the *lin-4* RNA", *Cell*, 88(5):637-646 (1997).

Mourelatos, et al., "miRNPs: a novel class of ribonucleoproteins containing numerous microRNAs", *Genes Dev.*, 16(6):720-8 (2002).

Nyce and Metzger, "DNA antisense therapy for asthma in an animal model", *Nature*, 385:721-725 (1997).

O'Donnell, et al., "c-Myc-regulated microRNAs modulate E2F1 expression", *Nature*, 435(7043):839-43 (2005).

Olsen and Ambros, "The lin-4 regulatory RNA controls developmental timing in *Caenorhabditis elegans* by blocking LIN-14 protein synthesis after the initiation of translation", *Dev Biol*, 216(2):671-80 (1999).

Pardridge, "Intravenous, non-viral RNAi gene therapy of brain cancer", *Expert Opin. Biol. Ther.*, 4(7):1103-13 (2004).

Pasquinelli, et al., "Conservation of the sequence and temporal expression of let-7 heterochronic regulatory RNA", *Nature*, 408(6808):86-9 (2000).

Pilkington, et al., "In vitro and in vivo models for the study of brain tumour invasion", *Anticancer Res.*, 17:4107-9 (1997).

Poy, et al., "A pancreatic islet-specific microRNA regulates insulin secretion", *Nature*, 432(7014):226-30 (2004).

Pulciani, et al., "Ras gene Amplification and malignant transformation", *Mol Cell Biol*, 5:2836-2841 (1985).

Reinhart, et al., "MicroRNAs in plants", *Genes Dev.*, 16:1616-1626 (2002).

Reinhart, et al., "The 21-nucleotide let-7 RNA regulates developmental timing in *Caenorhabditis elegans*", *Nature*, 403(6772):901-906 (2000).

Ribatti, et al., "The chick embryo chorioallantoic membrane as a model for in vivo research on angiogenesis", *Intl. J. Dev. Biol.*, 40:1189-97 (1999).

Rockwell, "In vivo-in vitro tumor systems: new models for studing the response of tumours to therapy", *Lab Anim. Sci.*, 27(5 Pt 2):831-51 (1977).

Rump, et al., "Modification of the plasma clearance and liver uptake of steroid ester-conjugated oligodeoxynucleotides by association with (lactosylated) low-density lipoprotein", *Biochem. Pharmacol.* 59(11):1407-1416 (2000).

Ruvkun et al., "The *Caenorhabditis elegans* heterochronic gene lin-14 encodes a nuclear protein that forms a temporal developmental switch", *Nature*, 338(6213):313-9 (1989).

Schneider, et al., "Building blocks for oligonucleotide analogs with dimethylene-sulfide, -sulfoxide and -sulfone groups replacing phosphodiester linkages", *Tetrahedron Lett.*, 31:335-38 (1990).

Slack, et al., "The lin-41 RBCC gene acts in the *C. elegans* heterochronic pathway between the let-7 regulatory RNA and the LIN-29 transcription factor", *Molec. Cell*, 5:659-669 (2000).

Slack and Ruvkun, "Temporal pattern formation by heterochronic genes", *Annu Rev Genet*, 31: 611-34 (1997).

Soutschek, et al., "Therapeutic silencing of an endogenous gene by systemic administration of modified siRNAs", *Nature*, 432(7014):173-178 (2004).

Stein, et al., "The genome sequence of *Caenorhabditis briggsae*: A platform for comparative genomics", *PLoS Biol*, 1(2):166-192 (2003).

Sternberg, "Lateral inhibition during vulval induction in *Caenorhabditis elegans*", *Nature*, 335:551-554 (1988).

Sullivan, et al., "SV40-encoded microRNAs regulate viral gene expression and reduce susceptibility to cytotoxic T cells", *Nature*, 435(7042):682-6 (2005).

Sulston and Horvitz, "Post embryonic cell lineages of the nematode *Caenorhabditis elegans*", *Dev Biol*, 56:110-156 (1977).

Takamizawa, et al., "Reduced expression of the let-7 microRNAs in human lung cancers in association with shortened postoperative survival", *Cancer Res*, 64:3753-3756 (2004).

Tam, et al., "Avian bic, a gene isolated from a common retroviral site in avian leukosis virus-induced lymphomas that encodes a noncoding RNA, cooperates with c-myc in lymphomagenesis and erythroleukemogenesis", *J Virol*, 76:4275-4286 (2002).

Tan, et al., "MAP kinase signaling specificity mediated by the LIN-1 Ets/LIN-31 WH transcription factor complex during *C. elegans* vulval induction", *Cell*, 93:569-580 (1998).

Timmons, et al., "Ingestion of bacterially expressed dsRNAs can produce specific and potent genetic interference in *Caenorhabditis elegans*", *Gene*, 263:103-112 (2001).

Tissenbaum and Guarente, "Model organisms as a guide to mammalian aging", *Dev. Cell*, 2(1), 9-19 (2002).

Uhlmann, et al., "Antisense oligonucleotides: A new therapeutic principle", *Chem. Rev.*, 90:543-584 (1990).

Valenzuela and Groffen, "Four human carcinoma cell lines with novel mutations in position 12 of c-K-ras oncogene", *Nucleic Acids Res.*, 14(2):843-52 (1986).

Vella, et al., "The *C. elegans* microRNA let-7 binds to imperfect let-7 complementary sites from the lin-41 3'UTR", *Genes Dev.*, 18(2):132-7 (2004).

Wang and Sternberg, "Pattern formation during *C. elegans* vulval induction", *Curr Top Dev Biol*, 51:189-220 (2001).

Wasserman, et al., "The evolution of B precursor leukemia in the Emu-ret mouse", *Blood*, 92(1):273-82 (1998).

Weidhaas, et al., "A *Caenorhabditis elegans* tissue model of radiation-induced reproductive cell death", *Proc. Natl. Acad. Sci. U.S.A.*, 103(26):9946-51 (2006).

Weidhaas, et al., "A conserved RAS/mitogen-activated protein kinase pathway regulates DNA damage-induced cell death postirradiation in Radelegans", *Cancer Res.*, 66(21):10434-8 (2006).

Wienholds, et al., "MicroRNA expression in zebrafish embryonic development", *Science*, 309(5732):310-1 (2005).

Wightman, et al., "Posttranscriptional regulation of the heterochronic gene lin-14 by lin-4 mediates temporal pattern formation in *C. elegans*", *Cell*, 75(5):855-862 (1993).

Wightman, et al., "Negative regulatory sequences in the lin-14 3'-untranslated region are necessary to generate a temporal switch during *Caenorhabditis elegans* development", *Genes Dev.*, 5(10):1813-24 (1991).

Xu, et al., "The *Drosophila* MicroRNA Mir-14 Suppresses Cell Death and Is Required for Normal Fat Metabolism", *Curr Biol*, 13(9):790-5 (2003).

Yang, et al., "Silencing of H-ras gene expression by retrovirus-mediated siRNA decreases transformation efficiency and tumorgrowth in a model of human ovarian cancer", *Oncogene*, 22(36):5694-701 (2003).

Yekta and Bartel, "MicroRNA-directed cleavage of HOXB8 mRNA", *Science*, 304(5670):594-6 (2004).

Yoo, et al., "Crosstalk between the EGFR and LIN-12/Notch pathways in *C. elegans* vulval development", *Science*, 303:663-666 (2004).

Yoon, et al., "Similarity of sli-1, a regulator of vulval development in *C. elegans*, to the mammalian proto-oncogene c-cbl", *Science*, 269:1102-1105 (1995).

Zeng, et al., "Both natural and designed micro RNAs can inhibit the expression of cognate mRNAs when expressed in human cells", *Mot. Cell*, 9(6):1327-33 (2002).

Zeng, et al., "MicroRNAs and small interfering RNAs can inhibit mRNA expression by similar mechanisms", *Proc. Natl. Acad. Sci. U.S.A.*, 100(17):9779-84 (2003).

Zhang, et al., "Intravenous RNA interference gene therapy targeting the human epidermal growth factor receptor prolongs survival in intracranial brain cancer", *Clin. Cancer Res.*, 10(11):3667-77 (2004).

Content of the Presentation given at Jaslock Hospital, Mumbai, India, Feb. 2004.

* cited by examiner

```
              T G A G G T A G - T A G G T T G T A T A G T T          Majority
                              |                   |
                             10                  20
                              |                   |
        1  T G A G G T A G - T A G T T T G T G C - - - T            let-7i RNA
        1  T G A G G T A G - T A G T G T G T A C A G T T            let-7h RNA
        1  T G A G G T A G - T A G T T T G T A C A G T A            let-7g RNA
        1  A G A G G T A G - T A G T T T G C A T A G T              let-7pred RNA
        1  A G A G G T A G - T A G G T T G C A T A G T              let-7d RNA
        1  T G A G G T A G - T A G A T T G T A T A G T T            let-7f-1 RNA
        1  T G A G G T A G - T A G G T T G T A T A G T T            let-7a-1 RNA
        1  T G A G G T A G - G A G G T T G T A T A G T              let-7e RNA
        1  T G A G G T A G - T A G G T T G T A T G G T T            let-7c RNA
        1  T G A G G T A G - T A G G T T G T G T G G T T            let-7b RNA
        1  T G A G G T A G - T A A G T T G T A T T G T T            mir-98 RNA
        1  T G A G G T A G - T A T G T A A T A T T G T A            mir-84 RNA
        1  T G A G G T A G G T G C G A G A A A T G - - A            mir-x RNA
        1  T G A G G T A G G C T C A G T A G T G C G A              mir-48 RNA T C C C T G A G A - - C C T C A A G T - G T G A          lin-4
           T C C C T G A G A - - C C C T A A C T T G T G A          mir-125b
           T C C C T G A G A A T T C T C G A A C A G C T T          mir-237
           T C C C T G A G A - - C C T T A A C C T G T G            mir-125a
```

FIG. 3

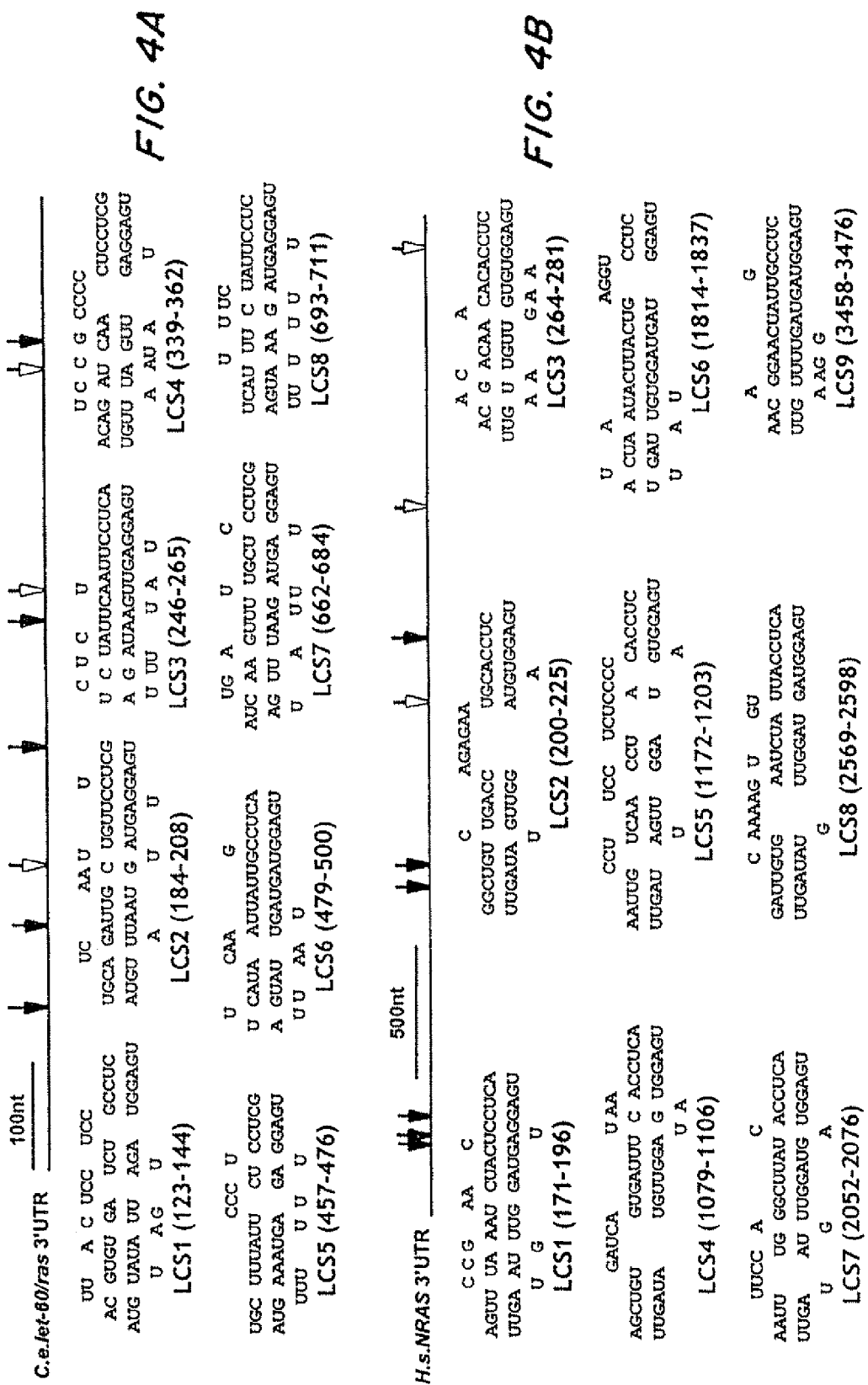

FIG. 4C

H.s.KRAS 3'UTR

|— 500nt —|

```
   A  GG      UU UU              G  C                         CCC    U   UU                   CA    U  G
GAC GU AAGUU U CCUCG       AUUAUGU AUCU UGCCUC            AAUG  UACA CUUAUU CCUCA          GGUUA GCGAUCUCUGCCUCG
UUG UA UUGGA GA GGAGU      UUGAUAUG UGGA AUGGAGU          UUGU AUGU GGAUGA GGAGU           UUGAU UGUUGGAGAUGGAGU
   A    G     U  U            U  UG                          A    U                          A    U
   LCS1 (153-177)             LCS2 (1805-1825)               LCS3 (1944-1968)                LCS4 (2364-2387)

GCG    C G       CCC                      G  U    G ACAG                          GCU  AGGG  AU     G
GGCUGU CAACU CUACCUCA GAUUA CACCUG GCCUCA    GG UGUAAGACUUAC     UACCUCG              AGU   UAUG  GAU UUA GCCUC
UUGAUA GUUGA GAUGGGG UUGAU GUGGAU UGGAGU     UU AUAUGUUGGAUG     AUGGAGU              UUG   AUAU  UUG GAU UGGAGU
      AUU    GA        U  GV                    G                                        U               GA
    LCS5 (2479-2502)  LCS6 (2506-2526)           LCS7 (3139-3157)                          LCS8 (3199-3226)
```

FIG. 4D

H.s.HRAS 3'UTR

|— 50nt —|

```
  CG GC  GGGACGCAG                    CCC   C  UA  CC                     CC  GUCC   CCAG
GAC UGGCGA U U  ACCCUC              GG AA CAGCCU GCU CCUC              AGC UUAC  CCU C GCCUC
UUG AUUGU G A  UGGGAGU              UU UU GUUGGA UGA GGAGU             UUG AAUG  GGA G UGGAGU
   A     G  AU                         GAA                  U             U  UU       A
   LCS1 (122-151)                       LCS2 (197-222)                    LCS3 (206-231)
```

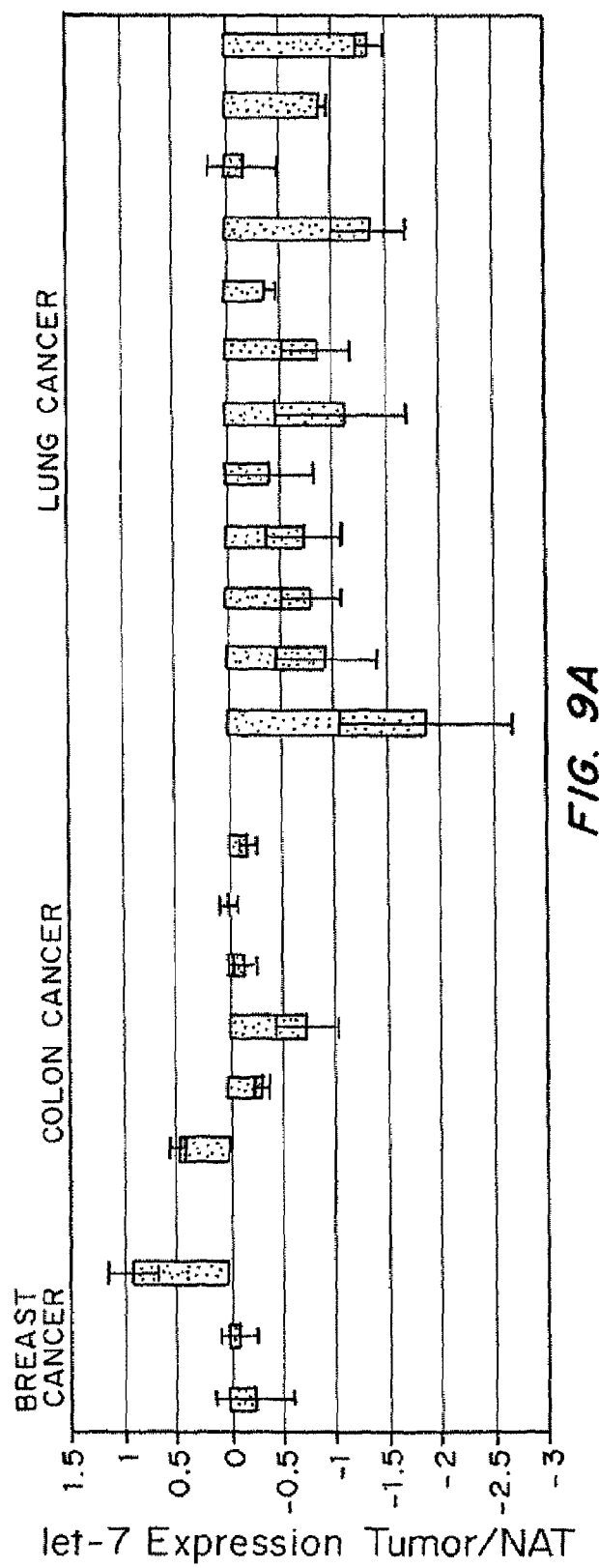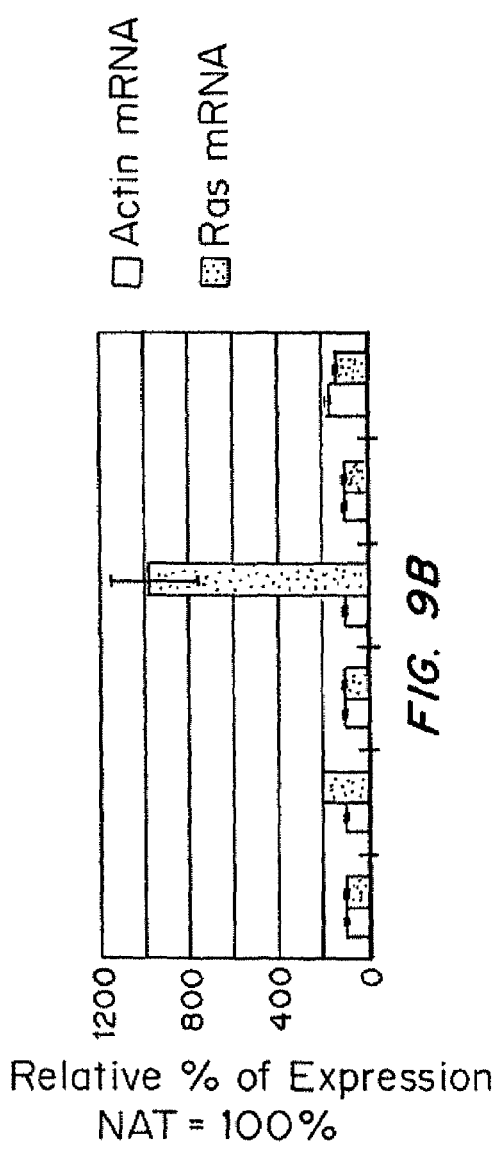
FIG. 9A
FIG. 9B

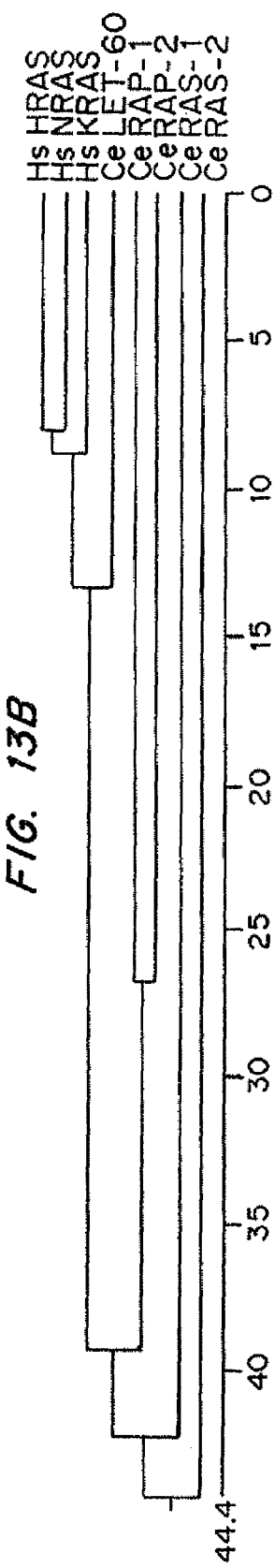
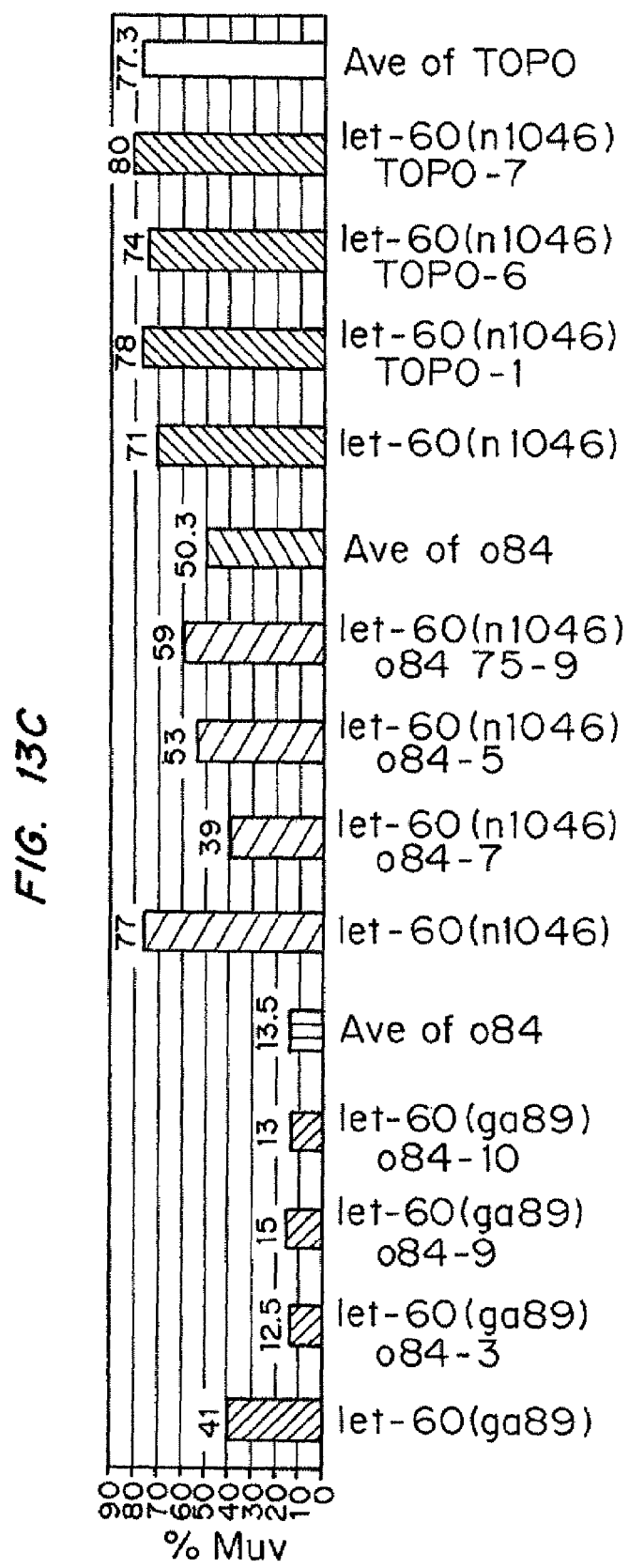
FIG. 13B
FIG. 13C

```
1171   TGGGGCCAAAATTCAGACTTGAAGTATGTTCTTTGAATACCTTAAGAAG    Hs NRAS short 3'UTR
2254   TGTGTCTGTAT----GACTGGTGTGGATCTCTAAAAAGTTTATTAAA     Hs NRAS long 3'UTR
2256   TGTGTCTGTAT----GACTGGTGTGGATCTCTAAAAAGTTTATTAAA     Rn nras 3'UTR
2190   TATGTCTATAT----GACTGGTGTGGATCTCTAAAAAGTTTATTAAA     Mn nras 3'UTR
464    TATGTCTATAT----GACTGGTGTGATCGTCGACC-TGCT            Cp nras 3'UTR
```

FIG. 14-5

X.l. NRAS 3'UTR

```
       CUUU  UA                    CU   G                 A    U    AG
AACAU    CAA  CCACUUACCUC    AAUU UGCU UUAUGCCUCA    AAC AAU GUUG CACCUC
UUGUA    GUU  GGUGGAUGGAGU   UUGA AUGU GAUAUGGAGU    UUG UUG UGAU GUGGAGU
    A U     A                    U   UG  G           AA  UG    A
      LCS1                         LCS2                   LCS3
```

D.r. NRAS 3'UTR

```
         U C                            G   U    U
AAUUAUACAUUUAC CCUCA           AAU AAUAAUUAUU CCUCA
UUGAUAUGUGGAUG GGAGU           UUG UUGUUGAUGA GGAGU
       U    AU                     A A         U
         LCS1                         LCS2
```

REGULATION OF ONCOGENES BY MICRORNAS

CROSS-REFERENCE TO RELATED APPLICATIONS

This application is a continuation in part of U.S. Ser. No. 11/219,379, filed Sep. 2, 2005, entitled "Regulation of Oncogenes by MicroRNAs" which claims priority to U.S. Ser. No. 60/606,855 entitled "Regulation of Oncogenes by MicroRNAs" filed Sep. 2, 2004, and also claims priority to U.S. Ser. No. 60/853,061 entitled "MicroRNA Manipulation to Alter the Radiation Response" filed Oct. 20, 2006 and U.S. Ser. No. 60/931,740 entitled "A Role for MicroRNA Manipulation in Altering Cellular Radiation Resistance" filed May 25, 2007.

STATEMENT REGARDING FEDERALLY FUNDED RESEARCH

The Federal Government has certain rights in this invention by virtue of Grant No. 1R01GM062594-01A1 and Grant No. 1R01GM064701-01 from the National Institutes of Health to Frank J. Slack.

BACKGROUND OF THE INVENTION

Cancer is a group of diseases characterized by uncontrolled growth and spread of abnormal cells. Cancer is caused by both external factors (tobacco, chemicals, radiation, and infections organisms) and internal factors (inherited mutations, hormones, immune conditions, and DNA damage). These factors may act together or sequentially to initiate and/or promote carcinogenesis. Cancer causes 1 of every 4 deaths and is the leading cause of death in people under age 85 in the United States. Nearly half of all men and a little over one third of all women in the U.S. will develop cancer during their lifetimes. Today, millions of people are living with cancer or have had cancer. The sooner a cancer is found and treatment begins, the better are the chances for living for many years.

Lung cancer is the leading cause of cancer deaths for both men and women in the United States. According to the American Cancer Society, about 160,000 people die annually of this disease, with about 170,000 newly diagnosed cases each year. Despite the use of surgery, chemotherapy, and radiation, the survival rate for patients remains extremely poor (>15% over 5 years). As estimated by the American Cancer Society, the 5-year survival rate for all cancers is about 64% for cancers diagnosed between 1995-2000. However, the survival rate varies depending on cancer type and the stage of cancer at time of detection. For example, the survival rate for brain, breast, and colon cancer is 33, 88, and 63%, respectively for cancers diagnosed between 1995-2000. Therefore, treatments in addition to the standard methods of treatment that include surgery, radiation, chemotherapy, immunotherapy, and hormone therapy are needed.

Misregulation of genes that control cell fate determination often contributes to cancer. Such altered genes are known as oncogenes. Oncogenes are called proto-oncogenes when they are normal (i.e., not mutated). Proto-oncogenes encode components of the cell's normal growth-control pathway. Some of these components are growth factors, receptors, signaling enzymes, and transcription factors.

Ras is one such oncogene. Mammalian ras genes code for closely related, small proteins (H-ras, K-ras and N-ras). Ras is found in normal cells, where it helps to relay signals by acting as a switch. When receptors on the cell surface are stimulated (by a hormone, for example), Ras is switched on and transduces signals that tell the cell to grow. If the cell-surface receptor is not stimulated, Ras is not activated and so the pathway that results in cell growth is not initiated. In about 30% of human cancers, Ras is mutated so that it is permanently switched on, telling the cell to grow regardless of whether receptors on the cell surface are activated or not. A high incidence of ras gene mutations is found in all lung cancers and adenocarcinomas (10% and 25%, respectively, K-ras), in malignant tumors of the pancreas (80-90%, K-ras), in colorectal carcinomas (30-60%, K-ras), in non-melanoma skin cancer (30-50%, H-ras), in hematopoietic neoplasia of myeloid origin (18-30%, K- and N-ras), and in seminoma (25-40%, K-ras). In other tumors, a mutant ras gene is found at a lower frequency: for example, in breast carcinoma (0-12%, K-ras), glioblastoma and neuroblastoma (0-10%, K- and N-ras).

Other oncogenes include members of the MYC family (c-MYC, N-MYC, and L-MYC), which have been widely studied, and amplification of myc genes has been found in a variety of tumor types including lung (c-MYC, N-MYC, L-MYC), colon (c-MYC), breast (c-MYC), and neuroblastoma (N-MYC). Genes that inhibit apoptosis have also been identified as oncogenes. The prototype of these genes is BCL-2. Originally identified at the chromosomal breakpoint in follicular lymphoma, this protein was found to inhibit cell death rather than promote cell growth. BCL-2 belongs to a family of intracellular proteins whose role is to regulate caspase activation that leads to DNA fragmentation and cell death. In melanoma, BCL-2 has been reported to be overexpressed in primary and metastatic lesions and this phenotype is associated with tumor progression.

Radiation therapy is one of the three primary modalities employed in cancer treatment. Although radiation has been in practice for over a century, the global genetic response necessary for tissues to survive radiation-induced injury remains largely unknown. This has limited the ability to develop meaningful routes to minimize normal tissue toxicity while enhancing tumor eradication. While single-protein targeting strategies have shown moderate success in preclinical models, few have been successful in human trials. Ras overexpression in tumors is considered a poor prognostic feature, and is hypothesized to be involved in the response to cytotoxic therapy. Ras signaling has been shown to be critical for protection from radiation induced target cell death (Brown and Wilson, *Canc. Biol. & Therapy*, 2:477-490 (2003)). Unfortunately, strategies directly targeting RAS or its upstream and/or downstream effectors have not successfully altered the radiation response in vivo.

A failure to identify radiation modulators may be due to the complex genetic cellular response to radiation, as indicated by microarray studies showing significant changes in the expression of at least 855 genes (>1.5 fold) within 4 hours of radiation. This suggests that regulatory molecules capable of regulating a large number of target genes in a rapid manner may be required to affect the radiation response.

Micro RNAs (referred to as "miRNAs") are small non-coding RNAs, belonging to a class of regulatory molecules found in plants and animals that control gene expression by binding to complementary sites on target messenger RNA (mRNA) transcripts (SEQ ID Nos. 1, 2 and 3). miRNAs are generated from large RNA precursors (termed pri-miRNAs) that are processed in the nucleus into approximately 70 nucleotide pre-miRNAs, which fold into imperfect stem-loop structures (Lee, Y., et al., Nature (2003) 425(6956):415-9) (FIG. 1). The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science (2001) 12:12 and Grishok, A., et al., Cell (2001) 106(1):23-34). mRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the RISC complex. This mechanism of miRNA-mediated gene silencing has been observed mainly in plants (Hamilton, A. J. and D. C. Baulcombe, Science (1999) 286(5441):950-2 and Reinhart, B. J., et al., *MicroRNAs in plants*. Genes and Dev. (2002) 16:1616-1626), but an example is known from animals (Yekta, S., I. H. Shih, and D. P. Bartel, Science (2004) 304(5670):594-6). In the second mechanism, miRNAs that bind to imperfect complementary sites on messenger RNA transcripts direct gene regulation at the posttranscriptional level but do not cleave their mRNA targets. mRNAs identified in both plants and animals use this mechanism to exert translational control of their gene targets (Bartel, D. P., Cell (2004) 116(2):281-97).

Hundreds of miRNAs have been identified in the fly, worm, plant and mammalian genomes. The biological role for the majority of the miRNAs remains unknown because almost all of these were found through cloning and bioinformatic approaches (Lagos-Quintana, M., et al., Curr Biol (2002) 12(9):735-9; Lagos-Quintana, M., et al., RNA (2003) 9(2): 175-179; Lagos-Quintana, M., et al., Science (2001) 294 (5543): 853-8; Lee, R. C. and V. Ambros, Science (2001) 294(5543):862-4; Lau, N. C., et al., Science (2001) 294(5543):858-62; Lim, L. P., et al., Genes Dev (2003) 17(8): 991-1008; Johnston, R. J. and O. Hobert, Nature (2003) 426 (6968):845-9; and Chang, S., et al., Nature (2004) 430(7001): 785-9).

It is likely that these uncharacterized miRNAs act as important gene regulators during development to coordinate proper organ formation, embryonic patterning, and body growth, but this remains to be established. In zebrafish, most miRNAs are expressed from organogenesis onward (Chen, P. Y., et al., Genes Dev (2005) 19(11):1288-93 and Wienholds, E., et al., Science, (2005)).

The biological roles for several miRNAs have been elucidated. These studies highlight the importance of these regulatory molecules in a variety of developmental and metabolic processes. For example, the *Drosophila* miRNA, bantam, was identified in a gain-of-function genetic screen for factors that caused abnormal tissue growth (Brennecke, J., et al., Cell (2003) 113(1):25-36). Bantam was found to induce tissue growth in the fly by both stimulating cell proliferation and inhibiting apoptosis (Brennecke, J., et al., Cell (2003). 113 (1):25-36). Although the proliferation targets for bantam have not been identified, a pro-apoptotic gene, hid, was shown to have multiple bantam complementary sites in its 3'UTR. Since hid gene expression was repressed by the bantam miRNA, this implicates a role for bantam in controlling apoptosis by blocking hid function. Another *Drosophila* miRNA, mir-14, was identified in a genetic screen for factors that modified Reaper-induced apoptosis in the fly eye (Xu, P., et al., Curr Biol (2003) 13(9):790-5). mir-14 was shown to be a strong suppressor of apoptosis. In addition, mir-14 also appears to play a role in the *Drosophila* stress response as well as in regulating fat metabolism. mRNAs also regulate Notch pathway genes in *Drosophila* (Lai, et al. Genes Dev (2005) 19(9):1067-80). A mammalian miRNA, mir-181, was shown to direct the differentiation of human B cells (Chen, C. Z., et al., Science (2004) 303(5654): 83-6), mir-373 regulates insulin secretion (Poy, M. N., et al., Nature (2004) 432(7014): 226-30), while other miRNAs regulate viral infections (Lecellier, C. H., et al., Science (2005) 308(5721):557-60 and Sullivan, C. S., et al., Nature (2005) 435(7042):682-6).

Studies to understand the mechanism of RNAi in *C. elegans, Drosophila* and human cells have shown that the miRNA and RNAi pathways may intersect (Grishok, A., et al. Cell (2001) 106(1):23-34 and Hutvagner, G., et al., Science (2001) 293(5531):834-8). mRNAs copurify with components of the RNAi effector complex, RISC, suggesting a link between miRNAs and siRNAs involved in RNAi (Mourelatos, Z., et al., Genes Dev (2002) 16(6):720-8; Hutvagner, G. and P. D. Zamore, Science (2002) 297(5589):2056-60; and Caudy, A. A., et al., Nature (2003) 425(6956): 411-4). There is also an indication that some protein factors may play a role in both the miRNA ribonucleoprotein (miRNP) and RISC and others might be unique to the miRNP (Grishok, A., et al., Cell (2001) 106(1): 23-34 and Carmell, M. A., et al., Genes Dev (2002) 16(21): 2733-42). For example, proteins of the argonaute/PAZ/PIWI family are components of both RISC and miRNPs. There is also mounting evidence that genes encoding these proteins are linked to cancer. hAgo3, hAgo1, and hAgo4 reside in region 1p34-35, often lost in Wilms' tumors, and Hiwi, is located on chromosome 12q24.33, which has been linked to the development of testicular germ cell tumors (Carmell, M. A., et al., Genes Dev (2002) 16(21):2733-42). In addition, DICER, the enzyme which processes miRNAs and siRNAs, is poorly expressed in lung cancers (Karube, Y., et al., Cancer Sci (2005) 96(2): 111-5).

It is therefore an object of the present invention to provide naturally occurring miRNAs for inhibition of expression of one or more oncogenes.

It is further an object of the present invention to provide naturally occurring nucleic acids for treatment or prophylaxis of one or more symptoms of cancer.

It is an even further object of the present invention to provide methods for sensitizing cancer cells to cytotoxic therapies including radiotherapy and chemotherapy.

BRIEF SUMMARY OF THE INVENTION

Genes that control cell differentiation and development are frequently mutated in human cancers. These include, but are not limited to, oncogenes such as RAS, c-myc and bcl-2. Naturally occurring microRNAs, in particular let-7, have been found that down regulate these oncogenes in humans. Some of the let-7 genes are located in chromosomal regions that are deleted in certain cancers. Therefore, up-regulating these specific microRNAs or providing analogous pharmaceutical compounds exogenously, should be effective cancer therapies for tumors resulting from activation or over-expression of these oncogenes. mRNAs nucleic acids including pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA, referred to jointly as "miRNAs" unless otherwise stated, are described. In one embodiment, the size range of the miRNA can be from 21 nucleotides to 170 nucleotides, although miRNAs of up to 2000 nucleotides can be utilized. In a preferred embodiment the size range of the miRNA is from 70 to 170 nucleotides in length. In another preferred embodiment, mature miRNAs of from 21 to 25 nucleotides in length can be used.

These miRNAs are useful as diagnostics and as therapeutics. In one embodiment, the compositions are administered prior to administration of radiotherapy to sensitize cells to the effects of the radiation. The compositions are administered to a patient in need of treatment of at least one symptom or manifestation (since disease can occur/progress in the absence of symptoms) of cancer. Aberrant expression of oncogenes is a hallmark of cancer, for example, lung cancer. The compositions can be administered alone or in combination with adjuvant cancer therapy such as surgery, chemotherapy, radiotherapy, thermotherapy, immunotherapy, hormone therapy and laser therapy, to provide a beneficial effect e.g. reduce tumor size, reduce cell proliferation of the tumor, inhibit angiogenesis, inhibit metastasis, or otherwise improve at least one symptom or manifestation of the disease.

BRIEF DESCRIPTION OF THE DRAWINGS

FIG. 3 depicts let-7 homologues from various species (SEQ ID Nos. 7, 8, 9, 10, 11, 12, 13, 14, 15, 16, 17, 18, 19, 20, 21, 22, 23, 24 and 25), including humans and mouse. There are 2 human homologues of lin-4 (SEQ ID No. 22), mir-125a (SEQ ID No. 25) and mir-125b (SEQ ID No. 23). mir-237 (SEQ ID No. 24) is a C. elegans lin-4 homologue.

FIGS. 4A-D depict potential LCSs in C. elegans let-60/RAS and in mammalian RAS genes. FIG. 4A C. elegans let-60/RAS mRNA 3'UTR, black arrows sites with similarity between C. elegans and C. briggsae and white arrows indicate non-similar sites. Shown below are predicted duplexes formed by LCSs (SEQ ID Nos. 26, 27, 28, 29, 32, 33, 34 and 35) (top) and miR-84 (SEQ ID Nos. 30 and 31) (bottom). let-7 and miR-84 are so similar that most let-7 sites are also potential miR-84 sites. FIGS. 4B, 4C, and 4D depict that H.s. NRAS, KRAS and HRAS mRNA 3'UTRs have 9 (SEQ ID Nos. 36, 37, 38, 40, 41, 42, 43, 44 and 45), 8 (SEQ ID Nos. 46, 47, 48, 49, 50, 51, 52 and 53) and 3 (SEQ ID Nos. 54, 55 and 56) potential LCSs, respectively. Black arrows indicate sites conserved among mammalian species (in most cases human, rat, mouse, hamster and guinea pig). Shown below are hypothesized duplexes formed by (top) and let-7a miRNA (SEQ ID No. 39) (bottom).

FIG. 7A is a graph of the quantification of the RAS antibody fluorescence from replicates of the transfections. Alternatively, HeLa cells were transfected with 100 nM let-7 inhibitor or negative control inhibitor. RAS immunofluorescence revealed that cells transfected with the let-7 inhibitor has increased levels of the RAS proteins relative to the negative control transfected cells.

FIG. 8A is a schematic showing the NRAS short (NRAS S) NRAS long (NRAS L) and KRAS 3'UTRs. Arrows indicate LCSs. The blackened areas indicate the sequence cloned behind the reporter. FIG. 8B is a graph of the relative repression of firefly luciferase expression standardized to a transfection control, renilla luciferase. pGL3-Cont is the empty vector. FIG. 8C is a graph of the induction of firefly luciferase expression when reporter plasmids with 3'UTR domains corresponding to KRAS and NRAS are co-transfected with an inhibitor of let-7, relative to a control inhibitor.

FIG. 9A is a graph of the expression of let-7 in 21 breast, colon, and lung tumors relative to associated normal adjacent tissue (NAT). Fluorescently labeled miRNA was hybridized to microarrays that included probes specific to let-7a and let-7c. Fluorescence intensities for the tumor and NAT were normalized by total fluorescence signal for all elements and the relative average signal from the let-7 probes in the tumor and normal adjacent samples are expressed as log ratios.

FIG. 9B is a graph of the correlation between RAS protein and let-7c expression in tumor and normal adjacent tissue samples from three lung squamous cell carcinomas. GAPDH and RAS proteins were measured from crude extracts of tumor and normal adjacent tissues using western analysis. The two proteins were assessed simultaneously by mixing the antibodies used for detection. The small RNA northern blot was assayed sequentially with radio-labeled probes specific to let-7c and U6 snRNA. NRAS mRNA in the tumor and normal adjacent tissues samples was measured by real-time PCR. The real-time data were normalized based on the real-time PCR detection of 18S rRNA in the various samples. The relative expression of NRAS in the normal adjacent tissues was taken to be 100% and the Ct value of NRAS in the tumor samples was used to assign the relative expression of NRAS in the tumor samples.

FIG. 12 is a sequence alignment of C. elegans (SEQ ID No. 81) (top) and C. briggsae (SEQ ID No. 82) (bottom) let-60/RAS mRNAs (consensus sequence shown in middle) (SEQ ID No. 83). LCSs are shown as black boxes.

FIGS. 13A-C show that Let-60 is the ortholog of human HRAS, KRAS, and NRAS proteins. FIG. 13A is a sequence alignment of C. elegans LET-60 (SEQ ID No. 87) with other RAS and RAS related proteins from humans (SEQ ID Nos. 84, 85 and 86) and C. elegans (SEQ ID Nos. 88, 89, 90 and 91). FIG. 13B is a dendrogram showing the relationship of LET-60 to other RAS related proteins. FIG. 13C is a graph showing quantification of the partial suppression of let-60(gf) alleles. o84-X are lines overexpressing mir-84, and TOPO-X are lines with the empty vector control. The average of each of the three experimental and control lines is indicated.

FIG. 14 is a sequence alignment of partial sequences from rodent (SEQ ID Nos. 94, 95 and 96) and human (SEQ ID Nos. 92 and 93) NRAS 3'UTRs. The LCSs shown in this alignment are boxed in black.

FIG. 15 (SEQ ID Nos. 97, 98, 99, 100, 101, 102 and 103) depicts potential let-7::LCS duplexes formed with *Xenopus laevis* and *Danio rerio* NRAS 3'UTRs.

FIG. 16A is a graph of the quantification of the antibody fluorescence from replicates of HepG2 cells transfected with let-7 or negative control siRNAs using antibodies specific to GAPDH or p21. FIG. 16B is a graph of the quantification of fluorescent signal from a single field of 50-100 cells for both the NRAS- and Negative Control siRNA transfections.

FIG. 19 depicts potential let-7 complementary sites (boxed) in the 3'UTR of human MYC (SEQ ID No. 104) and other vertebrates (SEQ ID Nos. 105, 106 and 107) and potential duplexes between let-7 (SEQ ID NOs. 39 and 110) and human MYC (SEQ ID Nos. 108 and 109).

FIG. 21A is a line graph showing the results obtained from RNA isolated from A549 cells. FIG. 21B is a line graph showing the results obtained from RNA isolated from CRL2741 lung epithelial cells.

DETAILED DESCRIPTION OF THE INVENTION

Definitions

Figure 1:
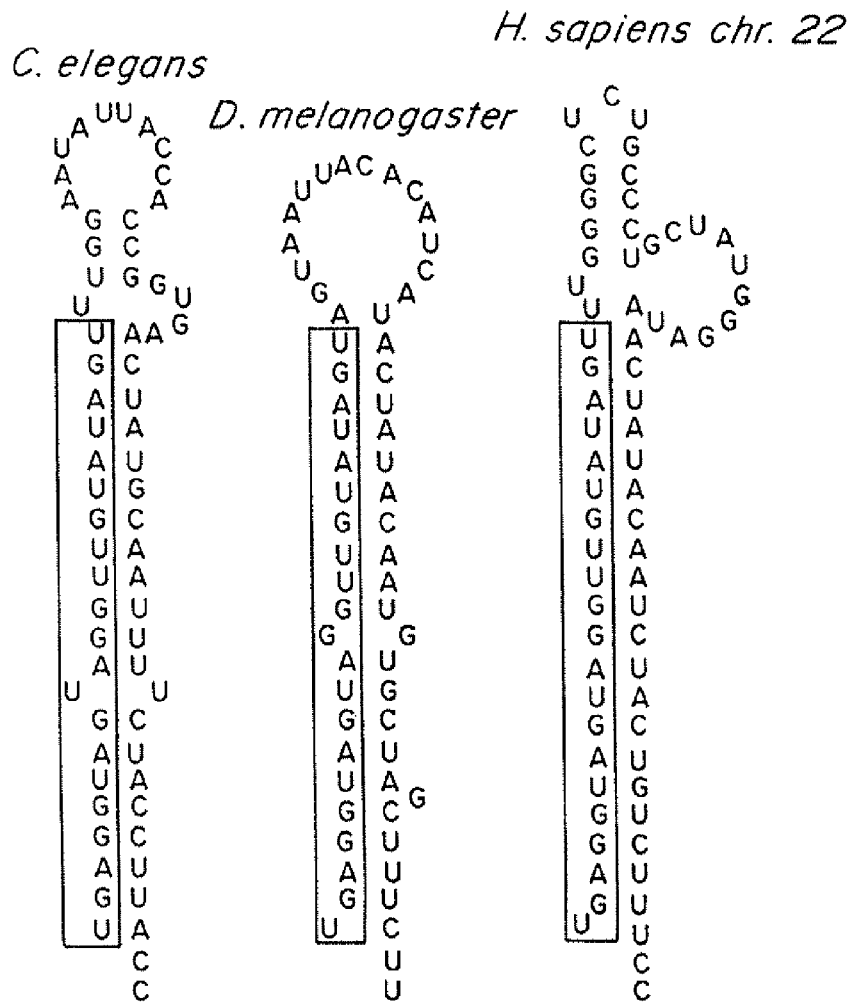
FIG. 1 depicts the predicted secondary structure of the let-7 pre-miRNA from various organisms (SEQ ID Nos. 1, 2 and 3). The shaded residues indicate the mature miRNA transcript excised by Dicer.

As used herein the term "nucleic acid" refers to multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). The term shall also include polynucleosides (i.e. a polynucleotide minus the phosphate) and any other organic base containing polymer. Purines and pyrimidines include but are not limited to adenine, cytosine, guanine, thymidine, inosine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art. Thus, the term nucleic acid also encompasses nucleic acids with substitutions or modifications, such as in the bases and/or sugars.

As used herein, the term "microRNA" refers to any type of interfering RNA, including but not limited to, endogenous microRNA and artificial microRNA. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA.

"MicroRNA flanking sequence" as used herein refers to nucleotide sequences including microRNA processing elements. MicroRNA processing elements are the minimal nucleic acid sequences which contribute to the production of mature microRNA from precursor microRNA. Precursor miRNA termed pri-miRNAs are processed in the nucleus into about 70 nucleotide pre-miRNAs, which fold into imperfect stem-loop structures.

The microRNA flanking sequences may be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. The artificial microRNA flanking sequences may be flanking sequences found naturally in the context of other microRNA sequences. Alternatively they may be composed of minimal microRNA processing elements which are found within naturally occurring flanking sequences and inserted into other random nucleic acid sequences that do not naturally occur as flanking sequences or only partially occur as natural flanking sequences.

The microRNA flanking sequences within the precursor microRNA molecule may flank one or both sides of the stem-loop structure encompassing the microRNA sequence. Preferred structures have flanking sequences on both ends of the stem-loop structure. The flanking sequences may be directly adjacent to one or both ends of the stem-loop structure or may be connected to the stem-loop structure through a linker, additional nucleotides or other molecules.

As used herein a "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures and terms are well known in the art. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base-pairing may not include any mismatches.

As used herein, the term "let-7" refers to the nucleic acid encoding the let-7 miRNA and homologues and variants thereof including conservative substitutions, additions, and deletions therein not adversely affecting the structure or function. Preferably, let-7 refers to the nucleic acid encoding let-7 from *C. elegans* (NCBI Accession No. AY390762), most preferably, let-7 refers to the nucleic acid encoding a let-7 family member from humans, including but not limited to, NCBI Accession Nos. AJ421724, AJ421725, AJ421726, AJ421727, AJ421728, AJ421729, AJ421730, AJ421731, AJ421732, and biologically active sequence variants of let-7, including alleles, and in vitro generated derivatives of let-7 that demonstrate let-7 activity.

Sequence variants of let-7 fall into one or more of three classes: substitutional, insertional or deletional variants. Insertions include 5' and/or 3' terminal fusions as well as intrasequence insertions of single or multiple residues. Insertions can also be introduced within the mature sequence of let-7. These, however, ordinarily will be smaller insertions than those at the 5' or 3' terminus, on the order of 1 to 4 residues.

Insertional sequence variants of let-7 are those in which one or more residues are introduced into a predetermined site in the target let-7. Most commonly insertional variants are fusions of nucleic acids at the 5' or 3? terminus of let-7.

Deletion variants are characterized by the removal of one or more residues from the let-7 RNA sequence. These variants ordinarily are prepared by site specific mutagenesis of nucleotides in the DNA encoding let-7, thereby producing DNA encoding the variant, and thereafter expressing the DNA in recombinant cell culture. However, variant let-7 fragments may be conveniently prepared by in vitro synthesis. The variants typically exhibit the same qualitative biological activity as the naturally-occurring analogue, although variants also are selected in order to modify the characteristics of let-7.

Substitutional variants are those in which at least one residue sequence has been removed and a different residue inserted in its place. While the site for introducing a sequence variation is predetermined, the mutation per se need not be predetermined. For example, in order to optimize the performance of a mutation at a given site, random mutagenesis may be conducted at the target region and the expressed let-7 variants screened for the optimal combination of desired activity. Techniques for making substitution mutations at predetermined sites in DNA having a known sequence are well known.

Nucleotide substitutions are typically of single residues; insertions usually will be on the order of about from 1 to 10 residues; and deletions will range about from 1 to 30 residues. Deletions or insertions preferably are made in adjacent pairs; i.e. a deletion of 2 residues or insertion of 2 residues. Substitutions, deletion, insertions or any combination thereof may be combined to arrive at a final construct. Changes may be made to increase the activity of the miRNA, to increase its biological stability or half-life. All such modifications to the nucleotide sequences encoding such miRNA are encompassed.

A DNA isolate is understood to mean chemically synthesized DNA, cDNA or genomic DNA with or without the 3' and/or 5' flanking regions. DNA encoding let-7 can be obtained from other sources by a) obtaining a cDNA library from cells containing mRNA, b) conducting hybridization analysis with labeled DNA encoding let-7 or fragments thereof (usually, greater than 100 bp) in order to detect clones in the cDNA library containing homologous sequences, and c) analyzing the clones by restriction enzyme analysis and nucleic acid sequencing to identify full-length clones.

As used herein nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTN using default parameters) are generally available. Software for performing BLAST analyses is publicly available through the National Center for Biotechnology Information (www.ncbi.nlm.nih.gov).

I. Compositions

Genes that control cell differentiation and development are frequently mutated in human cancers. These include, but are not limited to, oncogenes such as RAS, c-myc and bcl-2. Naturally occurring microRNAs, in particular let-7, have been found that down regulate these oncogenes in humans. Some of the let-7 genes are located in chromosomal regions that are deleted in certain cancers. Therefore, up-regulating these specific microRNAs or providing analogous pharmaceutical compounds exogenously, should be effective cancer therapies for tumors resulting from activation or over-expression of these oncogenes.

Figure 19:
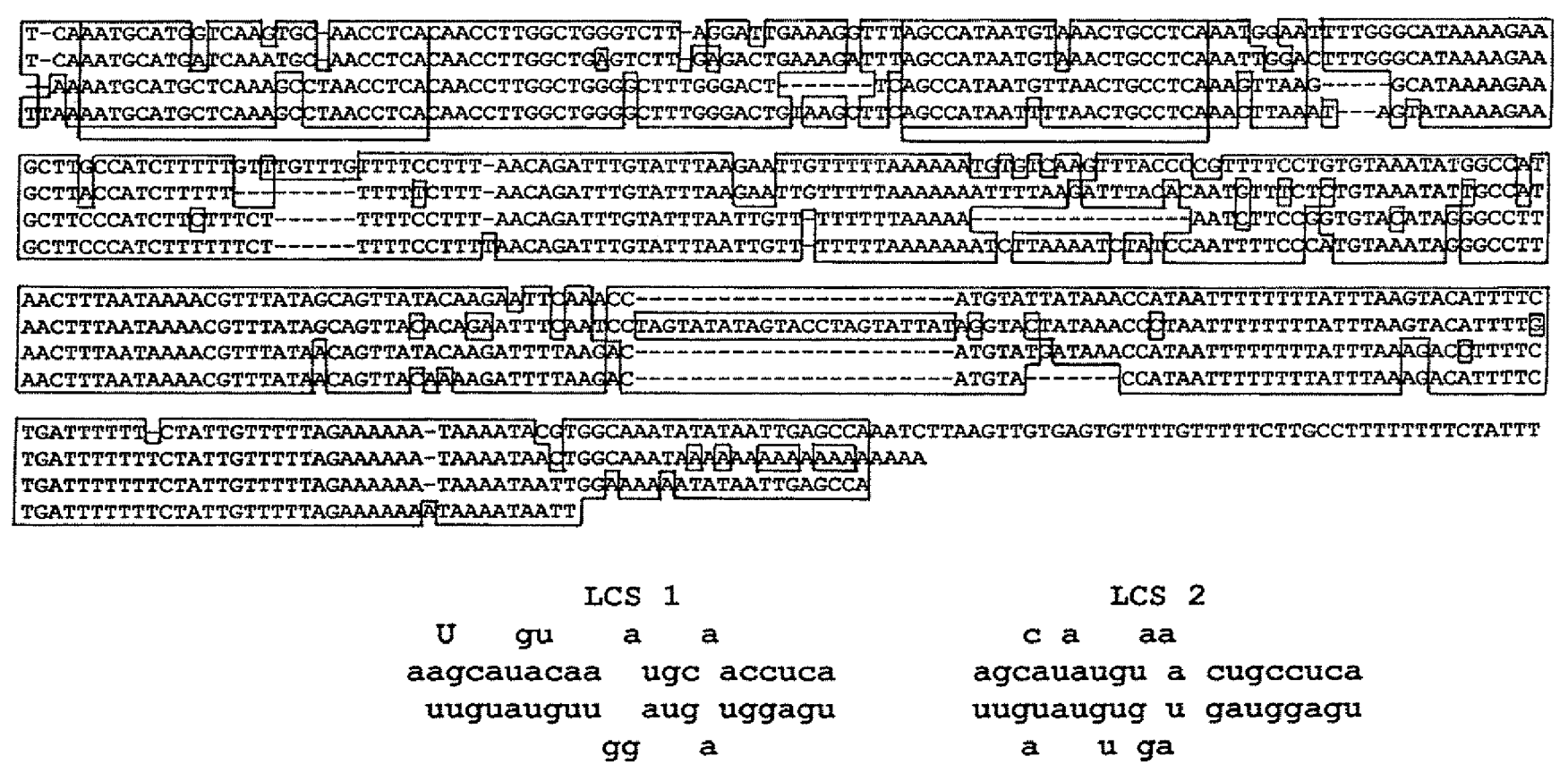

In preferred embodiments, the miRNA formulations are administered to individuals with a cancer that expresses one or more targets of let-7 or lin-4. More preferably, the formulations are administered to individuals with a cancer that over expresses RAS, MYC and/or BCL-2 or other target having one or more binding sites for the let-7. Multiple different pathways, along with the RAS/MAPK pathway, are implicated in cancer. The 3'UTRs of many known cancer genes have been examined and potential let-7 complementary sites have been identified in the 3'UTR of many of them (FIG. 19 and Table 1). These sites possess features of established let-7 complementary sites in known *C. elegans* let-7 targets (Reinhart, et al., Nature (2000) 403:901-906; Johnson, et al., Cell (2005) 120(5):635-47; Grosshans, et al., Dev Cell (2005) 8(3):321-30; Lin, et al., Dev Cell (2003) 4(5):639-50; Slack, et al., Molec. Cell (2000) 5:659-669; Vella, et al., Genes Dev (2004) 18(2):132-7). let-7 complementary sites (LCS) in the 3'UTRs of human c-MYC and BCL-2 have been identified (see FIG. 19 for c-MYC). Many of the potential target genes shown in Table 1 are also up-regulated in lung cancer as well as other cancers, leading to the conclusion that let-7 is responsible for repressing their expression in normal tissues. Some genes, like GRB2, have a similar number of LCSs as known let-7 target genes like KRAS (Table 1). VEGF was also identified as having let-7 complementary sites. These results indicate that let-7 can repress expression of multiple oncogenes. In addition to inhibiting cell proliferation, let-7 may also inhibit angiogenesis. Therefore, administration of let-7 may inhibit multiple pathways that promote survival of cancer or tumor cells (i.e., angiongenesis, decreased apoptosis and increased cell proliferation).

TABLE 1

Genes implicated in cancer that contain let-7 binding sites.

| *Homo sapiens* Gene | Number of LCS sites |
|---|---|
| EGF | 1 |
| EGFR | 1 |
| ERBB3 | 3 |
| GRB2 | 10 |
| NRAS | 9 |
| KRAS2 | 8 |
| HRAS | 3 |
| RAF1 | 1 |
| ARAF | 3 |
| MAP2K2 | 2 |
| MAPK1 | 1 |
| MAPK3 | 4 |
| MET | 3 |
| KIT | 3 |
| TP73L(AIX) | 5 |
| MYC | 2 |
| MYCL1 | 6 |
| MYCN | 4 |
| BCL2 | 5 |
| BCL2L1 | 5 |
| BCL2L2 | 6 |
| CCND1/cyclinD | 3 |
| CDK4 | 1 |
| MDM2/HDM2 | 4 |
| FES | 2 |
| FURIN | 2 |
| INSL3 | 2 |
| CSF1R/FMS | 1 |
| MYBL2 | 1 |
| MYB | 1 |
| PIK3CD | 6 |
| PIK3C2B | 4 |
| PIK3CG | 1 |
| PIK3R5 | 1 |
| TERT | 3 |
| AKT1 | 3 |
| AKT3 | 2 |
| VEGF | 3 |
| HLIN-41 | 4 |
| VDR | 7 |
| PXR | 3 |

TABLE 1-continued

Genes implicated in cancer that contain let-7 binding sites.

| *Homo sapiens* Gene | Number of LCS sites |
|---|---|
| FOXA1 | 2 |
| FOXA2 | A |
| ASH1L | 2 |
| ARID1B | 5 |
| GR | 2 |
| GLI2 | 1 |
| 14-3-3zeta | 6 |
| MO25 | 1 |
| SMG1 | 2 |
| FRAP1 | 3 |
| PER2 | 4 | miRNAS have Known Roles in Human Cancer

Recent studies from different laboratories show roles for miRNAs in human cancer (McManus, Seminars in Cancer Biology (2003) 13:253-258). The human miRNAs, mir-15 and mir-16, are preferentially deleted or down-regulated in patients with a common form of adult leukemia, B cell chronic lymphocytic leukemia (Calin, et al., Proc Natl Acad Sci USA (2002) 99(24):15524-9). This study suggests that miRNAs may function as tumor suppressor genes. The bic locus, which encodes the mir-155 miRNA works cooperatively with c-myc and induces B-cell lymphomas, presumably acting as a proto-oncogene (Haasch, D., et al., Cell Immunol (2002) 217(1-2): 78-86). miR142 acts as a tumor suppressor in chronic lymphocytic leukemia (Calin, G. A., et al., Proc Natl Acad Sci USA (2002) 99(24):15524-9; Lagos-Quintana, M., et al., Curr Biol (2002) 12(9):735-9). His-1 acts as an oncogene in B cell lymphoma (Haasch, D., et al., (2002); Lagos-Quintana, M., et al., (2002); Lagos-Quintana, M., et al., Science (2001) 294(5543):853-8; L1, et al. Am J Pathol (1997) 150:1297-305). Translocation of myc to the mir-142 locus causes B cell lymphoma (Lagos-Quintana, M., et al., (2002); Gauwerky, C. E., et al., Proc Natl Acad Sci USA, 1989. 86(22):8867-71). Mir-143 and mir-145 are poorly expressed in colorectal cancer (Michael, M. Z., et al., Mol Cancer Res (2003) 1(12):882-91). Over-expression of the mir-17, 18, 19, 20 locus is able to cause lymphomas in a mouse model and is up-regulated by MYC (He, L., et al., Nature (2005) 435(7043):828-33; O'Donnell, K. A., et al., Nature (2005) 435(7043):839-43).

Misregulation of genes that control cell fate determination often contributes to cancer. Genes that control cell differentiation and development are frequently mutated in human cancer. The model organism *Caenorhabditis elegans* has been used to identify genes required for cell differentiation in a stem-cell like lineage in the epidermis. *C. elegans* growth and development is divided into three major stages called embryo, larva and adult. Larval growth is subdivided into four larval stages (L1, L2, L3 and L4). Each larval stage ends in a molt and ultimately the animal matures into all adult. The genes that regulate timing of stage-appropriate cell division and differentiation are known as heterochronic genes (Slack, F. and G. Ruvkun, Annu Rev Genet (1997) 31:611-34; Banerjee, D. and F. Slack, Bioessays (2002) 24(2):119-29). In *C. elegans*, heterochronic genes control the timing of cell fate determination and differentiation. In heterochronic mutants, cells frequently fail to terminally differentiate, and instead divide again, a hallmark of cancer.

The founding members of the miRNA family, lineage defective-4 (lin-4) and lethal-7 (let-7), were identified through genetic analysis to control the timing of stage-appropriate cell division and differentiation in *C. elegans* (Lee, et al. *Cell* (1993) 75(5):843-854; Reinhart, B., et al., *Nature* (2000) 403: 901-906; Slack, F. and G. Ruvkun, *Annu Rev Genet* (1997) 31: 611-34; Banerjee, D. and F. Slack, *Bioessays* (2002) 24(2):119-29). let-7 and lin-4 control the timing of proliferation versus differentiation decisions. Some of these genes, like lin-4 and let-7, encode microRNAs (miRNAs) that are conserved in humans. Mutations in the lin-4 and let-7 miRNAs result in inappropriate reiterations of the first larval stage (L1) and the fourth larval stage (L4) fates, respectively, and these defects lead to disruptions in cell cycle exit (Lee, et al. Cell (1993) 75(5):843-854; Reinhart, B., et al., Nature (2000) 403:901-906). For example, in wild-type animals, specialized skin cells, known as seam cells, divide with a stem cell pattern and terminally differentiate at the beginning of the adult stage. The seam cells fail to terminally differentiate in lin-4 and let-7 mutant animals, and instead reiterate the larval fate and divide again. Lack of cell cycle control and failure to terminally differentiate are hallmarks of cancer.

The expression patterns for lin-4 and let-7 correlate with their role in directing developmental timing. lin-4 RNA accumulates during the L1 stage and is responsible for the L1/L2 transition in nematodes by inhibiting the expression of lin-14 and lin-28, repressors of post-L1 fates (Lee, et al. Cell (1993) 75(5):843-854; Ambros, V. and H. R. Horvitz, Science (1984) 226:409-416; Wightman, et al., Cell (1993) 75(5):855-862; Moss, et al. Cell (1997) 88(5): 37-46; and Feinbaum, R. and V. Ambros, Dev Biol (1999) 210(1):87-95). let-7 RNA accumulates during the L4 stage and is responsible for the L4/Adult transition by down-regulating the expression of lin-41, hbl-1 and RAS (Johnson, et al., Cell (2005) 120(5): 635-47; Grosshans, et al., Dev Cell (2005) 8(3) 321-30; Lin, et al., Dev Cell (2003) 4(5):639-50; Slack, F. J., Molec. Cell (2000) 5:659-669).

Figure 2:
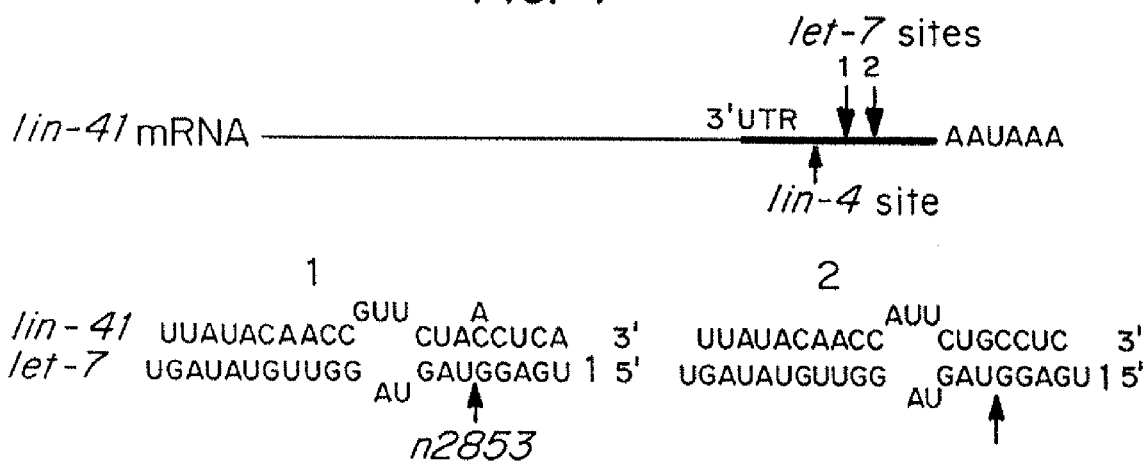
FIG. 2 is a schematic of potential RNA/RNA duplexes between a C. elegans miRNA, let-7, (SEQ ID No. 6) and the target mRNA, lin-41 (SEQ ID Nos. 4 and 5). The position of a loss-of-function mutation for the let-7 miRNA, let-7 (n2853), is shown by an arrow below the duplexes.

These 21-22 nucleotide miRNAs exert their effect by binding to imperfect complementary sites within the 3'-untranslated regions (3'UTRs) of their target protein-coding mRNAs and repress the expression of these genes at the level of translation (Lee, et al. Cell (1993) 75(5):843-854; Reinhart, B., et al., Nature (2000) 403:901-906; Moss, et al. Cell (1997) 88(5):637-46; Lin, S. Y., et al., Dev Cell (2003) 4(5):639-50; Slack, F. J., et al., Molec. Cell (2000) 5:659-669; Abrahante, J. E., et al., Dev Cell (2003) 4(5):625-37; and Olsen, P. H. and V. Ambros, Dev Biol (1999) 216(2):671-80). Deletion of let-7 miRNA complementary sites (LCS) (SEQ ID No. 4 and SEQ ID No. 5) from the lin-41 3'UTR (FIG. 2) showed abrogation of the normal down-regulation of lin-41 during the L4 and adult stages and recent work has shown that these complementary sites alone are sufficient for regulation on lin-41 (Reinhart, B., et al., Nature (2000) 403:901-906; Slack, F. J., et al., Molec, Cell (2000) 5:659-669; Vella, M. C., et al., Genes Dev (2004) 18(2):132-7).

The let-7 target gene, lin-41 is similar to known oncogenes. *C. elegans* lin-41 loss-of-function (lf) mutations cause cells to terminally differentiate precociously, opposite to of the effect seen with let-7(lf), while over-expression of lin-41 causes let-7(lf)-like seam cell proliferation (Reinhart, B., et al., Nature (2000) 403: 901-906; Slack, F. J., et al., Molec. Cell (2000) 5:659-669). Like let-7, lin-41 is an important cell proliferation and differentiation gene. let-7 and lin-41 work together to cause cells to proliferate or differentiate at the right time.

lin-41 encodes a member of the RBCC (RING finger, B box, Coiled Coil (Freemont, Ann. New York. Acad. Sci. (1993) 684:174-192) family of proteins. Members of this family have diverse proposed functions, such as transcription and RNA binding, and include the PML (Kakizuka, A., et al., Cell (1991) 66:663-674), TIF1 (Le Dourarin, B., et al., EMBO J. (1995) 14(9):2020-2033) and Rfp proto-oncogenes. The most common form of promyelocytic leukemia involves a translocation that fuses PML to the RARa gene. The N-terminal part of TIF1, is fused to B-raf in the oncogenic protein T18 (Le Dourarin, B., et al., EMBO J. (1995) 14(9):2020-2033). Emu-ret mice, carrying an RFP/RET fusion gene under the transcriptional control of the immunoglobulin heavy chain enhancer, develop B lineage leukemias and lymphomas (Wasserman, et al. Blood (1998) 92(1):273-82). In transformed NIH 3T3 cells, the amino-terminal half of Rfp with a RING finger motif is fused to a truncated Ret receptor tyrosine kinase, Rfp/Ret (Hasegawa, N., et al., Biochem Biophys Res Commun (1996) 225(2):627-31). Members of this family are associated with cancer progression. It is expected that mammalian lin-41 is also a proto-oncogene.

In addition to lin-41, let-7 regulates other target genes in a 3' UTR dependent manner, including hunchback-like1 (hbl-1) (Lin Shin-Yi, J., et al. Dev. Cell, 2003(4):1-20) and let-60, the *C. elegans* RAS oncogene homologue (see Example 1). As shown in Table 2, let-60/RAS contains multiple let-7 complimentary sites in its 3'UTR and let-60(lf) suppresses let-7 mutants. let-60/RAS is best understood for its role in *C. elegans* vulval development and let-60/RAS 3'UTR is sufficient to restrict let-60/RAS expression only to the vulval precursor cell (VPC) that absolutely requires let-60/ras activity (the primary induced cell, 1° or P6.p cell). In a normal animal, a let-7 family member, mir-84, is expressed in all the VPCs except the primary induced cell, and represses let-60/ras expression in these cells.

In animals carrying let-60 activating mutations, more than one VPC is induced to differentiate into the 1 cell fate, leading to excess vulvae. Over-expression of mir-84 suppresses activating mutations in let-60/RAS. Many activating mutations in the human NRAS, KRAS and HRAS genes alter the same amino acid affected by the *C. elegans* let-60 activating mutation. Since RAS is mutated in multiple human cancers (Malumbres, et al. Nat Rev Cancer (2003) 3(6):459-65), the hypothesis that human RAS is a target of human let-7 was tested and determined to be (see example 1 below).

lin-4 and let-7 miRNAs are evolutionarily conserved in higher animals, including humans (FIG. 3) (SEQ ID Nos. 7, 8, 9, 10, 11, 12, 13, 14, 15, 16, 17, 18, 19, 20, 21, 22, 23, 24 and 25) and temporally expressed (see examples below) which implies a universal role for these miRNAs during animal development (Lagos-Quintana, M., et al., Mouse. Curr Biol (2002) 12(9):735-9 and Pasquinelli, A. E., et al., Nature (2000) 408(6808):86-9). let-7 orthologues have been identified in mammals, including humans, and let-7 is expressed in human lung tissues as judged by northern blot (Pasquinelli, A. E., et al.). There are 3 exact copies of the mature let-7 sequence in the sequenced human genome (referred to as let-7a1, let-7a2, let-7a3 under control of separate promoters) and a variety of close homologues that differ from let-7 at certain nucleotide positions (e.g. let-7c (SEQ ID No. 16), see FIG. 3). The nematode, fly and human let-7 genes are processed from a precursor form (pre-let-7) that is predicted to form a stem loop structure which is also conserved (FIG. 1). Similarly, there are 2 human and mouse homologues of lin-4 (SEQ ID No. 22), named mir-125a (SEQ ID no. 25) and mir-125b (SEQ ID No. 23) (FIG. 3).

Recent work has demonstrated that microRNA expression profiles can accurately diagnose particular cancers better than standard messenger RNA expression profiles (Lu, et al, *Nature* 435:834-838 (2005)).

miRNAs Useful to Regulate Human Oncogenes

Naturally occurring microRNAs that regulate human oncogenes, pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA, have been identified. The size of the miRNA is typically from 21 nucleotides to 170 nucleotides, although nucleotides of up to 2000 nucleotides can be utilized. In a preferred embodiment the size range of the pre-miRNA is between 70 to 170 nucleotides in length and the mature miRNA is between 21 and 25 nucleotides in length.

Nucleic Acids

General Techniques

General texts which describe molecular biological techniques include Sambrook, Molecular Cloning: a Laboratory Manual ($2^{nd}$ ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, *Part I. Theory and Nucleic Acid Preparation*, P. Tijssen, ed. Elsevier, N.Y. (1993); Berger and Kimmel, Guide to Molecular Cloning Techniques Methods in Enzymology volume 152 Academic Press, Inc., San Diego, Calif. These texts describe mutagenesis, the use of vectors, promoters and many other relevant topics related to, e.g., the generation and expression of genes that encode let-7 or any other miRNA activity. Techniques for isolation, purification and manipulation of nucleic acids, genes, such as generating libraries, subcloning into expression vectors, labeling probes, and DNA hybridization are also described in the texts above and are well known to one of ordinary skill in the art.

The nucleic acids, whether miRNA, DNA, cDNA, or genomic DNA, or a variant thereof, may be isolated from a variety of sources or may be synthesized in vitro. Nucleic acids as described herein can be administered to or expressed in humans, transgenic animals, transformed cells, in a transformed cell lysate, or in a partially purified or a substantially pure form.

Nucleic acids are detected and quantified in accordance with any of a number of general means well known to those of skill in the art. These include, for example, analytical biochemical methods such as spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immuno-fluorescent assays, and the like, Southern analysis, Northern analysis, Dot-blot analysis, gel electrophoresis, RT-PCR, quantitative PCR, other nucleic acid or target or signal amplification methods, radiolabeling, scintillation counting, and affinity chromatography.

Various types of mutagenesis can be used, e.g., to modify a nucleic acid encoding a gene with let-7 or other miRNA activity. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, and mutagenesis using gapped duplex DNA. Additional suitable methods include point mismatch repair, mutagenesis using repair-deficient host strains, restriction-selection and restriction-purification, deletion mutagenesis, mutagenesis by total gene synthesis, double-strand break repair. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure. Changes may be made to increase the activity of the miRNA, to increase its biological stability or half-life.

Comparative hybridization can be used to identify nucleic acids encoding genes with let-7 or other miRNA activity, including conservative variations of nucleic acids.

Nucleic acids "hybridize" when they associate, typically in solution. Nucleic acids hybridize due to a variety of well characterized physico-chemical forces, such as hydrogen bonding, solvent exclusion, base stackinge. An extensive guide to the hybridization of nucleic acids is found in Tijssen (1993) Laboratory Techniques in Biochemistry and Molecular Biology-Hybridization with Nucleic Acid Probes part I chapter 2, "Overview of principles of hybridization and the strategy of nucleic acid probe assays," (Elsevier, N.Y.), as well as in Ausubel, supra. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Suitable nucleic acids for use in the methods described herein include, but are not limited to, pri-miRNA, pre-miRNA, mature miRNA or fragments of variants thereof that retain the biological activity of the miRNA and DNA encoding a pri-miRNA, pre-miRNA, mature miRNA, fragments or variants thereof, or DNA encoding regulatory elements of the miRNA.

Viral Vectors

In one embodiment the nucleic acid encoding a miRNA molecule is on a vector. These vectors include a sequence encoding a mature microRNA and in vivo expression elements. In a preferred embodiment, these vectors include a sequence encoding a pre-miRNA and in vivo expression elements such that the pre-miRNA is expressed and processed in vivo into a mature miRNA. In another embodiment, these vectors include a sequence encoding the pri-miRNA gene and in vivo expression elements. In this embodiment, the primary transcript is first processed to produce the stem-loop precursor miRNA molecule. The stem-loop precursor is then processed to produce the mature microRNA.

Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have general utility for the high-efficiency transduction of nucleic acids in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., N.Y. (1990) and Murry, E. J. Ed. "Methods in Molecular Biology," vol. 7, Humana Press, Inc., Cliffton, N.J. (1991).

Promoters

The "in vivo expression elements" are any regulatory nucleotide sequence, such as a promoter sequence or promoter-enhancer combination, which facilitates the efficient expression of the nucleic acid to produce the microRNA. The in vivo expression element may, for example, be a mammalian or viral promoter, such as a constitutive or inducible promoter or a tissue specific promoter. Examples of which are well known to one of ordinary skill in the art. Constitutive mammalian promoters include, but are not limited to, polymerase promoters as well as the promoters for the following genes: hypoxanthine phosphoribosyl transferase (HPTR), adenosine deaminase, pyruvate kinase, and beta.-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

Examples of tissue-specific promoters include, but are not limited to, the promoter for creatine kinase, which has been used to direct expression in muscle and cardiac tissue and immunoglobulin heavy or light chain promoters for expression in B cells. Other tissue specific promoters include the human smooth muscle alpha-actin promoter.

Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol 7-alpha hydroylase (CYP-7) promoter, beta-galactosidase alpha-2,6 sialyltransferase promoter, insulin-like growth factor binding protein (IGFBP-1) promoter, aldolase B promoter, human transferrin promoter, and collagen type I promoter.

Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1).

Exemplary tissue-specific expression elements for gastric tissue include but are not limited to the human H+/K+-ATPase alpha subunit promoter.

Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter.

Exemplary tissue-specific expression elements for the endometrium include, but are not limited to, the uteroglobin promoter.

Exemplary tissue-specific expression elements for adrenal cells include, but are not limited to, cholesterol side-chain cleavage (SCC) promoter.

Exemplary tissue-specific expression elements for the general nervous system include, but are not limited to, gamma-gamma enolase (neuron-specific enolase, NSE) promoter.

Exemplary tissue-specific expression elements for the brain include, but are not limited to, the neurofilament heavy chain (NF-H) promoter.

Exemplary tissue-specific expression elements for lymphocytes include, but are not limited to, the human COL-1/granzyme B promoter, the terminal deoxy transferase (TdT), lambda 5, VpreB, and lck (lymphocyte specific tyrosine protein kinase p56lck) promoter, the humans CD2 promoter and its 3' transcriptional enhancer, and the human NK and T cell specific activation (NKG5) promoter.

Exemplary tissue-specific expression elements for the colon include, but are not limited to, pp60c-src tyrosine kinase promoter, organ-specific neoantigens (OSNs) promoter, and colon specific antigen-P promoter.

Exemplary tissue-specific expression elements for breast cells include, but are not limited to, the human alpha-lactalbumin promoter.

Exemplary tissue-specific expression elements for the lung include, but are not limited to, the cystic fibrosis transmembrane conductance regulator (CFTR) gene promoter.

Other elements aiding specificity of expression in a tissue of interest can include secretion leader sequences, enhancers, nuclear localization signals, endosmolytic peptides, etc. Preferably, these elements are derived from the tissue of interest to aid specificity.

In general, the in vivo expression element shall include, as necessary, 5' non-transcribing and 5' non-translating sequences involved with the initiation of transcription. They optionally include enhancer sequences or upstream activator sequences.

Methods and Materials for Production of miRNA

The miRNA can be isolated from cells or tissues, recombinantly produced, or synthesized in vitro by a variety of techniques well known to one of ordinary skill in the art.

In one embodiment, miRNA is isolated from cells or tissues. Techniques for isolating miRNA from cells or tissues are well known to one of ordinary skill in the art. For example, miRNA can be isolated from total RNA using the mirVana miRNA isolation kit from Ambion, Inc. Another techniques utilizes the flashPAGE™ Fractionator System (Ambion, Inc.) for PAGE purification of small nucleic acids.

The miRNA can be obtained by preparing a recombinant version thereof (i.e., by using the techniques of genetic engineering to produce a recombinant nucleic acid which can then be isolated or purified by techniques well known to one of ordinary skill in the art). This embodiment involves growing a culture of host cells in a suitable culture medium, and purifying the miRNA from the cells or the culture in which the cells are grown. For example, the methods include a process for producing a miRNA in which a host cell containing a suitable expression vector that includes a nucleic acid encoding an miRNA is cultured under conditions that allow expression of the encoded miRNA. In a preferred embodiment the nucleic acid encodes let-7. The miRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the miRNA into the host cell can be effected by calcium phosphate transfection, DEAE, dextran mediated transfection, or electroporation (Davis, L. et al., *Basic Methods in Molecular Biology* (1986)).

Any host/vector system can be used to express one or more of the miRNAs. These include, but are not limited to, eukaryotic hosts such as HeLa cells and yeast, as well as prokaryotic host such as E. colt and *B. subtilis*. miRNA can be expressed in mammalian cells, yeast, bacteria, or other cells where the miRNA gene is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In the preferred embodiment, the miRNA is expressed in mammalian cells. Examples of mammalian expression systems include C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors will comprise an origin of replication, a suitable promoter, polyadenylation site, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Potentially suitable yeast strains include *Saccharomyces cerevisiae, Schizosaccharomyces pombe, Kluyveromyces strains, Candida*, or any yeast strain capable of expressing miRNA. Potentially suitable bacterial strains include *Escherichia coli, Bacillus subtilis, Salmonella typhimurium*, or any bacterial strain capable of expressing miRNA.

In a preferred embodiment, genomic DNA encoding let-7 is isolated, the genomic DNA is expressed in a mammalian expression system, RNA is purified and modified as necessary for administration to a patient. In a preferred embodiment the let-7 is in the form of a pre-miRNA, which can be modified as desired (i.e. for increased stability or cellular uptake).

Knowledge of DNA sequences of miRNA allows for modification of cells to permit or increase expression of an endogenous miRNA. Cells can be modified (e.g., by homologous recombination) to provide increased miRNA expression by replacing, in whole or in part, the naturally occurring promoter with all or part of a heterologous promoter so that the cells express the miRNA at higher levels. The heterologous promoter is inserted in such a manner that it is operatively linked to the desired miRNA encoding sequences. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also may be engineered to express an endogenous gene comprising the miRNA under the control of inducible regulatory elements, in which case the regulatory sequences of the endogenous gene may be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al.

The miRNA may be prepared by culturing transformed host cells under culture conditions suitable to express the miRNA. The resulting expressed miRNA may then be purified from such culture (i.e., from culture medium or cell extracts) using known purification processes, such as gel filtration and ion exchange chromatography. The purification of the miRNA may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether; immunoaffinity chromatography, or complementary cDNA affinity chromatography.

The miRNA may also be expressed as a product of transgenic animals, which are characterized by somatic or germ cells containing a nucleotide sequence encoding the miRNA. A vector containing DNA encoding miRNA and appropriate regulatory elements can be inserted in the germ line of animals using homologous recombination (Capecchi, Science 244:1288-1292 (1989)), such that the express the miRNA. Transgenic animals, preferably non-human mammals, are produced using methods as described in U.S. Pat. No. 5,489,743 to Robinson, et al., and PCT Publication No. WO 94/28122 by Ontario Cancer Institute. miRNA can be isolated from cells or tissue isolated from transgenic animals as discussed above.

In a preferred embodiment, the miRNA can be obtained synthetically, for example, by chemically synthesizing a nucleic acid by any method of synthesis known to the skilled artisan. The synthesized miRNA can then be purified by any method known in the art. Methods for chemical synthesis of nucleic acids include, but are not limited to, in vitro chemical synthesis using phosphotriester, phosphate or phosphoramidite chemistry and solid phase techniques, or via deosynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages may be preferred. Nucleic acids containing modified internucleoside linkages may also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), dimethylene-sulfoxide ($-CH_2-SO-CH_2-$), dimethylene-sulfone ($-CH_2-SO_2-CH_2-$), 2'-O-alkyl, and 2'-deoxy-2'-fluoro phosphorothioate internucleoside linkages are well known in the art (see Uhlmann et al., 1990, *Chem. Rev.* 90:543-584; Schneider et al., 1990, *Tetrahedron Lett.* 31:335 and references cited therein). U.S. Pat. Nos. 5,614,617 and 5,223,618 to Cook, et al., 5,714,606 to Acevedo, et al., 5,378,825 to Cook, et al., 5,672,697 and 5,466,786 to Buhr, et al., 5,777,092 to Cook, et al., 5,602,240 to De Mesmaeker, et al., 5,610,289 to Cook, et al. and 5,858, 988 to Wang, also describe nucleic acid analogs for enhanced nuclease stability and cellular uptake.

Formulations

The nucleic acids described above are preferably employed for therapeutic uses in combination with a suitable pharmaceutical carrier. Such compositions comprise an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids some of which are described herein.

It is understood by one of ordinary skill in the art that nucleic acids administered in vivo are taken up and distributed to cells and tissues (Huang, et al., *FEBS Lett.* 558(1-3): 69-73 (2004)). For example, Nyce et al. have shown that antisense oligodeoxynucleotides (ODNs) when inhaled bind to endogenous surfactant (a lipid produced by lung cells) and are taken up by lung cells without a need for additional carrier lipids (Nyce and Metzger, *Nature*, 385:721-725 (1997). Small nucleic acids are readily taken up into T24 bladder carcinoma tissue culture cells (Ma, et al., *Antisense Nucleic Acid Drug Dev.* 8:415-426 (1998). siRNAs have been used for therapeutic silencing of an endogenous genes by systemic administration (Soutschek, et al., *Nature* 432, 173-178 (2004)).

The nucleic acids described above may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The nucleic acids may also be encapsulated in suitable biocompatible microcapsules, microparticles or microspheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example in Sambrook et al., 1989, *Molecular Cloning: A Laboratory Manual*, Cold Spring Harbor Laboratory, New York; and Ausubel et al., 1994, *Current Protocols in Molecular Biology*, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. By way of example, and not by limitation, the nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, and thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose). Preservatives and other additives may also be present such as, for example, antimicrobials, antioxidants, chelating agents and inert gases. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The nucleic acids alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, and nitrogen. For administration by inhalation, the nucleic acids are conveniently delivered in the form of an aerosol spray presentation from pressurized packs or a nebulizer, with the use of a suitable propellant.

In some embodiments, the nucleic acids described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the nucleic acids are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al.,

*Bioorg. Med. Chem. Lett.* 14(19):4975-4977 (2004)) and in vivo (Soutschek, et al., *Nature* 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.* 59(11):1407-1416 (2000)). Other groups that can be attached or conjugated to the nucleic acids described above to increase cellular uptake, include, but are not limited to, acridinederivatives; cross-linkers such as psoralen derivatives, azidophenacyl, proflavin, and azidoproflavin; artificial endonucleases; metal complexes such as EDTA-Fe(II) and porphyrin-Fe(II); alkylating moieties,; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also described methods for enhanced delivery of nucleic acids molecules.

These pharmaceutical formulations may be manufactured in a manner that is itself known, e.g., by means of conventional mixing, dissolving, granulating, levigating, emulsifying, encapsulating, entrapping or lyophilizing processes.

The formulations described herein of the nucleic acids embrace fusions of the nucleic acids or modifications of the nucleic acids, wherein the nucleic acid is fused to another moiety or moieties, e.g., targeting moiety or another therapeutic agent. Such analogs may exhibit improved properties such as activity and/or stability. Examples of moieties which may be linked or unlinked to the nucleic acid include, for example, targeting moieties which provide for the delivery of nucleic acid to specific cells, e.g., antibodies to pancreatic cells, immune cells, lung cells or any other preferred cell type, as well as receptor and ligands expressed on the preferred cell type. Preferably, the moieties target cancer or tumor cells. For example, since cancer cells have increased consumption of glucose, the nucleic acids can be linked to glucose molecules. Monoclonal humanized antibodies that target cancer or tumor cells are preferred moieties and can be linked or unlinked to the nucleic acids. In the case of cancer therapeutics, the target antigen is typically a protein that is unique and/or essential to the tumor cells (e.g., the receptor protein HER-2).

II. Methods of Treatment

The compositions are administered to a patient in need of treatment of at least one symptom or manifestation (since disease can occur/progress in the absence of symptoms) of cancer where it acts as a radiation or chemotherapy sensitizer. The compositions described herein can be administered to a subject prior to administration of a cytotoxic therapy in an amount effective to sensitize cells or tissues to be treated to the effects of the cytotoxic therapy. In one embodiment the cytotoxic therapy is radiotherapy. In another embodiment the cytotoxic therapy is chemotherapy. Sensitization describes a condition of the cells or tissues to be treated in which prior administration of the compositions described herein increases at least one effect of the cytotoxic therapy on the cells or tissues relative to cells or tissues not receiving prior administration of the compositions described herein. The increased effect may be on reduction of tumor size, reduction in cell proliferation of a tumor, inhibition of angiogenesis, inhibition of metastasis, or improvement of at least one symptom or manifestation of the disease.

Aberrant expression of oncogenes is a hallmark of cancer such as lung cancer. In another embodiment, the compositions are administered in an effective amount to inhibit gene expression of one or more oncogenes. In yet another embodiment, the compositions are administered in an effective amount to inhibit gene expression of RAS, MYC, and/or BCL-2.

Methods for treatment or prevention of at least one symptom or manifestation of cancer are also described including administration of an effective amount of a composition containing a nucleic acid molecule to alleviate at least one symptom or decrease at least one manifestation. In a preferred embodiment, the cancer is lung cancer. The compositions described herein can be administered in effective dosages alone or in combination with adjuvant cancer therapy such as surgery, chemotherapy, radiotherapy, thermotherapy, immunotherapy, hormone therapy and laser therapy, to provide a beneficial effect, e.g. reduce tumor size, reduce cell proliferation of the tumor, inhibit angiogenesis, inhibit metastasis, or otherwise improve at least one symptom or manifestation of the disease.

Method of Administration

In general, methods of administering nucleic acids are well known in the art. In particular, the routes of administration already in use for nucleic acid therapeutics, along with formulations in current use, provide preferred routes of administration and formulation for the nucleic acids described above.

Nucleic acid compositions can be administered by a number of routes including, but not limited to: oral, intravenous, intraperitoneal, intramuscular, transdermal, subcutaneous, topical, sublingual, or rectal means. Nucleic acids can also be administered via liposomes. Such administration routes and appropriate formulations are generally known to those of skill in the art.

Administration of the formulations described herein may be accomplished by any acceptable method which allows the miRNA or nucleic acid encoding the miRNA to reach its target. The particular mode selected will depend of course, upon factors such as the particular formulation, the severity of the state of the subject being treated, and the dosage required for therapeutic efficacy. As generally used herein, an "effective amount" of a nucleic acid is that amount which is able to treat one or more symptoms of cancer or related disease, reverse the progression of one or more symptoms of cancer or related disease, halt the progression of one or more symptoms of cancer or related disease, or prevent the occurrence of one or more symptoms of cancer or related disease in a subject to whom the formulation is administered, as compared to a matched subject not receiving the compound or therapeutic agent. The actual effective amounts of drug can vary according to the specific drug or combination thereof being utilized, the particular composition formulated, the mode of administration, and the age, weight, condition of the patient, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. The composition can be injected intradermally for treatment or prevention of cancer, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

Preferably, the agent and/or nucleic acid delivery system are provided in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the miRNA over a certain time period, for example, hours, days, weeks, months or years. This may be accomplished, for example, by repeated administrations of a formulation or by a sustained or controlled release delivery system in which the miRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include, but are not limited to, time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the miRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the miRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose-administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the miRNA employed and the condition of the patient, as well as the body weight or surface area of the patient to be treated. The size of the dose is also determined by the existence, nature, and extent of any adverse side-effects that accompany the administration of a particular vector, and formulation, in a particular patient.

Therapeutic compositions comprising one or more nucleic acids are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment versus non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the patient. Administration can be accomplished via single or divided doses.

In vitro models can be used to determine the effective doses of the nucleic acids as a potential cancer treatment. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. JS. Dev. Biol., 40: 1189-97 (1999) and Li et al., Clin. Exp. Metastasis, 17:423-9 (1999), respectively. Suitable tumor cells lines are available, e.g. from American Type Tissue Culture Collection catalogs.

In vivo models are the preferred models to determine the effective doses of nucleic acids described above as potential cancer treatments. Suitable in vivo models include, but are not limited to, mice that carry a mutation in the KRAS oncogene (Lox-Stop-Lox K-Ras$^{G12D}$ mutants, Kras2$^{tm4Tyj}$) available from the National Cancer Institute (NCI) Frederick Mouse Repository. Other mouse models known in the art and that are available include but are not limited to models for gastrointestinal cancer, hematopoietic cancer, lung cancer, mammary gland cancer, nervous system cancer, ovarian cancer, prostate cancer, skin cancer, cervical cancer, oral cancer, and sarcoma cancer (see http://emice.nci.nih.gov/mouse_models/).

In determining the effective amount of the miRNA to be administered in the treatment or prophylaxis of disease the physician evaluates circulating plasma levels, formulation toxicities, and progression of the disease.

The dose administered to a 70 kilogram patient is typically in the range equivalent to dosages of currently-used therapeutic antisense oligonucleotides such as Vitravene®(fomivirsen sodium injection) which is approved by the FDA for treatment of cytomegaloviral RNA, adjusted for the altered activity or serum half-life of the relevant composition.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the nucleic acids can also be administered in therapeutically effective amounts as a portion of an anti-cancer cocktail. An anti-cancer cocktail is a mixture of the oligonucleotide or modulator with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the nucleic acids described herein include, but are not limited to: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

Diseases to be Treated

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic formulations described herein may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma. Therapeutic formulations can be administered in therapeutically effective dosages alone or in combination with adjuvant cancer therapy such as surgery, chemotherapy, radiotherapy, thermotherapy, immunotherapy, hormone therapy and laser therapy, to provide a beneficial effect, e.g. reducing tumor size, slowing rate of tumor growth, reducing cell proliferation of the tumor, promoting cancer cell death, inhibiting angiogenesis, inhibiting metastasis, or otherwise improving overall clinical condition, without necessarily eradicating the cancer.

Cancers include, but are not limited to, biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor. In a preferred embodiment, the formulations are administered for treatment or prevention of lung cancer.

In addition, therapeutic nucleic acids may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the nucleic acids to reduce the risk of developing cancers. In one embodiment, a nucleic acid in a suitable formulation may be administered to a subject who has a family history of cancer, or to a subject who has a genetic predisposition for cancer. In other embodiments, the nucleic acid in a suitable formulation is administered to a subject who has reached a particular age, or to a subject more likely to get cancer. In yet other embodiments, the nucleic acid in a suitable formulation is administered to subjects who exhibit symptoms of cancer (e.g., early or advanced). In still other embodiments, the nucleic acid in a suitable formulation may be administered to a subject as a preventive measure. In some embodiments, the nucleic acid in a suitable formulation may be administered to a subject based on demographics or epidemiological studies, or to a subject in a particular field or career.

EXAMPLES

The present invention will be further understood by reference to the following non-limiting examples.

Example 1

RAS is Regulated by the let-7 microRNA Family

Figure 10A:
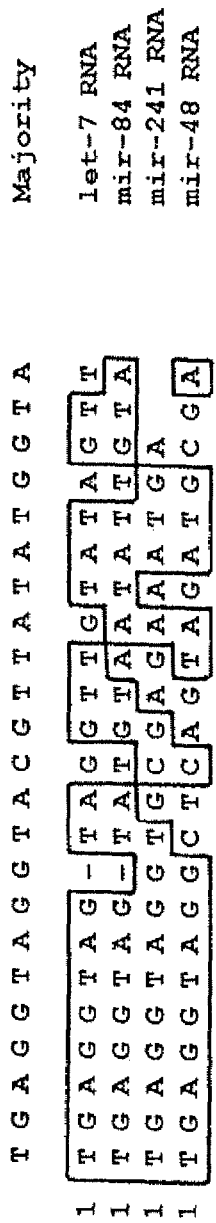
FIG. 10A is a sequence comparison of the let-7 family of miRNAs (SEQ ID Nos. 19, 21, 57, 58 and 59) in C. elegans.
Figure 10B:
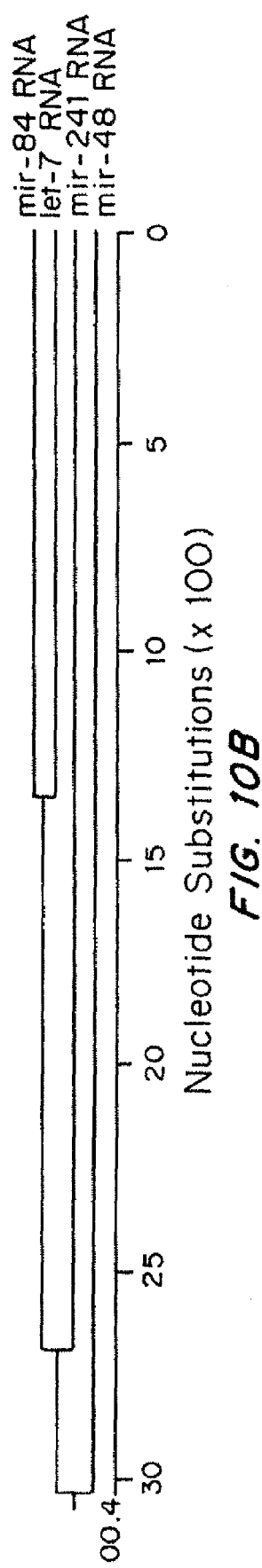
FIG. 10B is a dendrogram of let-7 family members.

C. elegans let-7, mir-48, mir-84 and mir-241 encode four developmentally regulated miRNAs that comprise the let-7 family (Lau et al., (2001) Science 294, 858-862; Lim et al., (2003) Genes Dev 17, 991-1008; Reinhart et al., (2000) Nature 403, 901-906). This family displays high sequence identity, with particular conservation at the 5' end of the mature miRNAs (FIG. 10A, 10B). The C. elegans let-7 family miRNAs, mir-84, plays a role in vulval development, a model for dissecting RAS/MAP Kinase signaling (Wang and Sternberg, (2001) Curr Top Dev Biol 51, 189-220). C. elegans let-60/RAS is regulated by members of the let-7 family. let-7 and mir-84 are complementary to multiple sites in the 3' UTR of let-60/RAS. let-7 and mir-84 are expressed in a reciprocal manner to let-60/RAS in the hypodermis and the vulva respectively.

let-7 and mir-84 genetically interact with let-60/RAS, consistent with negative regulation of RAS expression by let-7 and mir-84. The results demonstrate for the first time that miRNAs can regulate RAS, a critical human oncogene. Moreover, all three human RAS genes have let-7 complementary sites in their 3'UTRs that subject the oncogenes to let-7 miRNA-mediated regulation in cell culture. Lung tumor tissues display significantly reduced levels of let-7 and significantly increased levels of RAS protein relative to normal lung tissue, suggesting let-7 regulation of RAS as a mechanism for let-7 in lung oncogenesis.

Experimental Procedures

Plasmid Constructs. PSJ840 (mir-84::gfp) was made by amplifying 2.2 kb of genomic sequence (base pairs −2201 to −9) upstream of the mature mir-84 sequence from N2 genomic DNA and adding a SmaI site and an AgeI site to the 5' and 3' ends, respectively, using the polymerase chain reaction (PCR) with primers MIR84UP and MIR84DN (all primer sequences available upon request). This product was digested with SmaI and AgeI and then cloned into the pPD95.70 vector digested with SmaI and AgeI. The mir-84 upstream DNA contained various sequence elements that are also found in the let-7 upstream DNA. PSJo84 (mir-84(+++)) was made by amplifying 3.0 kb of genomic sequence (base pairs −2201 to +792) upstream and downstream of the mature mir-84 sequence including the mir-84 sequence itself from N2 genomic DNA and adding SmaI sites to both the 5' and 3' ends using PCR with primers MIR84UP and MIR84DN2. This product was ligated into the pCR4-TOPO vector using the TOPO TA Cloning Kit as described by the manufacturer (Invitrogen). The empty TOPO control vector was made by digesting PSJo84 with EcoRI, extracting the 4 kb vector band and self ligating it. The miR-84 deletion plasmid, o84Δ84 (Δmir-84(+++)), was made by overlap extension PCR, starting with two separate PCR reactions using primers MIR84UP with DEL84DN and MIR84DN2 with DEL84UP and PSJo84 plasmid as template. The two PCR products were purified (QIAGEN) and then used together as template for the final PCR using primers MIR84UP and MIR84DN2. This final product, identical to PSJo84 except for the deletion of the 75 nt pre-miR84 encoding sequence, was ligated into the pCR2.1-TOPO vector using the TOPO TA Cloning Kit (Invitrogen) and called o84Δ84. GFP60 was made by amplifying the 819 bp of genomic sequence encoding the let-60 3'UTR from N2 genomic DNA and adding EcoRI and SpeI sites to the 5' and 3' ends, respectively, using PCR with primers 3LET60UP and 3LET60DN. This product was digested with EcoRI and SpeI and then cloned into the pPD95.70 vector (Fire Lab) digested with EcoRI and SpeI, thus replacing the unc-54 3'UTR found in pPD95.70 with the let-60 3'UTR, The green fluorescent protein gene (GFP) followed by the let-60 3'UTR was then amplified out of this plasmid and BglII and NotI sites were added to the 5' and 3' ends respectively using PCR with primers BGLGFP and 3UTRNOT. This PCR product was digested with BglII and NotI and ligated into PB255 digested with BglII and NotI, resulting in the plasmid GFP60 containing the lin-31 promoter and enhancer driving GFP with the let-60 3UTR. GFP54 was made by amplifying gfp followed by the unc-54 3'UTR out of pPD95.70 using PCR with primers BGLGFP and 3UTRNOT. This PCR product was digested and ligated into PB255 digested with BglII and NotI, resulting in the plasmid GFP54 containing the lin-31 promoter and enhancer driving GFP with the unc-54 3UTR. pGL3-NRAS S and pGL3-NRAS L were made by amplifying the entire 1140 bp shorter form of the H.s. NRAS 3'UTR out of a IMAGE cDNA clone (accession # A1625442), or the entire 3616 bp longer form of the H.s. NRAS 3'UTR (excluding the first 43 bp) from H.s. genomic DNA, and adding NheI sites to the ends by PCR using primers SMJ100 and SMJ101 or SMJ102 and SMJ103 respectively. These products were digested with NheI and ligated into pGL3-Control (Promega) digested with XbaI and treated with CIP, resulting in Rrluc-expressing plasmids containing either the short or long form of the H.s. NRAS 3'UTR. To generate pFS1047, containing the col-10-lacZ-let-60 3'UTR reporter gene, the entire let-60 3'UTR was subcloned into the SacII and NcoI sites of plasmid B29 (Wightman, B., Ha, I., and Ruvkun, G. (1993) Cell 75, 855-862).

let-60; let-7 Double Mutants. let-60(n2021); let-7(mn112) double mutant animals were generated by crossing let-60 (n2021) heterozygotes with let-7(mn112) unc-3/0; mnDpl hemiyzgotes. From this cross, 180 individual homozygous let-7(mn112) F2 animals were female, as determined by their Unc-phenotype, due to the tight linkage of the let-7(mn112) to unc-3. Of these, 10 survived into adulthood and produced eggs. The resulting progeny from these animals died as larvae with the rod-like phenotype that is characteristic of let-60 mutant animals, thus showing that these animals all contained the let-60(n2021) mutation, and that adult survival was likely due to the let-60(n2021) mutation, confirming our RNAi data. From 180 F2s, 25% (or about 45 animals) would have been predicted to be let-60(n2021) homozygous. Since one saw survival of only 10 of these animals, this indicates a suppression of about 22%, similar to what was observed with RNAi. However, because the brood sizes were low (usually about 10 hatched larvae and several unhatched eggs); and because of a combination of larval lethality as well as limited parental survival, double mutant lines could not be established for further analysis; all progeny died as larvae.

C. elegans and Transgenic reporter analysis. All animal experiments were performed at room temperature or 20° C. unless stated otherwise. All experimental plasmids were injected in animals at 50-100 ng/µl. Two different markers, rol-6 (100 ng/µl) and myo-3::gfp (50 ng/µl), were separately co-injected with PSJo84: myo-3::gfp (50 ng/µl) was co-injected with o84Δ84; and myo-2::gfp (5 ng/µl) was co-injected with GFP60 and GFP54. These animals are mosaic for the transgenes. To compare expression between individual lines, the percent expression of GFP in each of the Pn.p cells was normalized relative to the expression of the highest expressing Pn.p cell and represented as a fraction of the highest expresser for each individual line of animals. For each construct the average of the lines was calculated along with the standard deviation for each construct represented as error bars (mir-84::gfp n=239, gfp60 n=42 and gfp54 n=40). For the mir-84(+++) analysis, animals were examined using DIC optics to score seam cell and vulval anatomy. LacZ reporter analysis was as described (Vella et al., (2004) Genes Dev 18, 132-137). The lin-41 3'UTR missing its LCSs (pFS1031) was used as a control (Reinhart et al., (2000)). RNAi methods were standard feeding procedures using synchronized L1s (Timmons et al., (2001) Gene 263, 103-112). All RNAi experiments were done in parallel to an empty vector (L4440) feeding control. See Supplemental Experimental procedures for details on the let-60; let-7 double mutant cross.

let-7/RAS association in mammalian cells. HeLa S3 cells grown in D-MEM (GIBCO) supplemented with 10% fetal bovine serum (GIBCO) were cotransfected in 12-well plates using Lipofectamine 2000 (Invitrogen) according to the manufacturer's protocol using 1.0 µg/well of Pp-luc-expressing plasmid (pGL3-Control from Promega, pGL3-NRAS S pGL3-NRAS L and pGL3-KRAS) and 0.1 µg/well of Rr-luc-expressing plasmid (pRL-TK from Promega). 24 hrs post transfection, the cells were harvested and assayed using the Dual Luciferase assay as described by the manufacturer (Promega). HeLa cells grown as above were transfected in 24-well plates with 30 pmoles of Anti-miR let-7 or negative control #1 inhibitors (Ambion) using Lipofectamine 2000. Three days post-transfection, RAS expression was monitored by immunofluorescence using an FITC conjugated primary antibody against RAS protein (US Biological). The resulting fluorescent signal was analyzed using the appropriate filter set and was quantified using MetaMorph software. The fluorescence intensity of 150-300 cells was typically measured in one or a few viewing areas. The experiments with both the precursors and the inhibitors were performed three times. The photos represent single viewing fields from one of the experiments and are representative of the triplicate experiment. Identically grown HeLa cells were cotransfected in 24-well plates using Lipofectamine 2000 (Invitrogen) according to the manufacturer's protocol using 200 ng/well of Pp-luc-expressing plasmid (pGL3-Control from Promega, pGL3-NRAS S pGL3-NRAS L and pGL3-KRAS). 48 hrs post transfection, the cells were harvested and assayed using the Luciferase assay as described by the manufacturer (Promega).

HepG2 cells grown in D-MEM (GIBCO) supplemented with 10% fetal bovine serum (GIBCO) were transfected with 15 or 5 pmole of Pre-miR Let-7c or negative control #1 Precursor miRNAs (Ambion) in 24-well plates using siPort Neo-FX (Ambion) according to the manufacturer's protocol. Three days post-transfection, RAS expression was monitored by immunofluorescence as described above.

mRNA microarray analysis procedures used by Ambion, Inc. Total RNA from tumor and normal adjacent tissue (NAT) samples from 3 breast cancer, 6 colon cancer, and 12 lung cancer patients was isolated using the mirVana RNA Isolation Kit (Ambion). Twenty µg of each total RNA sample was fractionated by polyacrylamide gel electrophoresis (PAGE) using a 15% denaturing polyacrylamide gel and the miRNA fractions for each sample were recovered. The miRNAs from all of the samples were subjected to a poly(A) polymerase reaction wherein amine modified uridines were incorporated as part of ~40 nt long tails (Ambion). The tailed tumor samples were fluorescently labeled using an amine-reactive Cy3 (Amersham) and the normal adjacent tissue samples were labeled with Cy5 (Amersham). The fluorescently labeled miRNAs were purified by glass-fiber filter binding and elution (Ambion) and the tumor and normal adjacent tissue samples from the same patient were mixed. Each sample mixture was hybridized for 14 hours with slides upon which 167 miRNA probes were arrayed. The microarrays were washed 3×2 minutes (min) in 2×SSC and scanned using a GenePix 4000B (Axon). Fluorescence intensities for the Cy3- and Cy5-labeled samples for each element were normalized by total Cy3 and Cy5 signal on the arrays. The normalized signal intensity for each element was compared between the tumor and NAT samples from each pair of patient samples and expressed as a log ratio of the tumor to normal adjacent sample.

Northern Analysis. mir-84 northerns were performed as described (Johnson et al., (2003) Dev Biol 259, 364-379). For human tissues, 1 ug of total RNA from the tumor and normal adjacent tissues of patients 1 and 5 were fractionated by PAGE using a 15% denaturing polyacrylamide gel. The RNA was transferred to a positively charged nylon membrane by electroblotting at 200 mA in 0.5×TBE for 2 hours. The Northern blot was dried and then incubated overnight in 10 ml of ULTRAhyb-Oligo (Ambion) with $10^7$ cpm of a radio-labeled transcript complementary to let-7c. The blot was washed 3×10 min at room temperature in 2×SSC, 0.5% SDS and then 1×15 min at 42° C. in 2×SSC, 0.5% SDS. Overnight phosphorimaging using the Storm system (Amersham), revealed let-7c. The process was repeated using a radio-labeled probe for 5S rRNA.

Lung tumor protein/northern/mRNA analysis. Total RNA and protein were isolated from tumor and normal adjacent tissue samples from three lung cancer patients using the mirVana PARIS Kit (Ambion). let-7 miRNA and U6 snRNA were measured using the Northern procedure described above. NRAS and B-actin mRNA as well as 18S rRNA were quantified by real-time RT-PCR using primers specific to each of the target RNAs. RAS and GAPDH protein were measured by Western analysis using the RAS antibody described above and an antibody for GAPDH (Ambion).

Accession numbers. The following sequences were searched for 3'UTR LCSs; Hs KRAS (Genbank M54968), Hs HRAS (M176795), Hs NRAS (BC005219). NRAS is known to exist as a 2 Kb and a 4.3 Kb form. BC005219 represents the short form with a 1151 nt polyadenylated 3'UTR. Two human EST clones (Genbank BU177671 and BG388501) were sequenced to obtain additional NRAS 3'UTR sequence. This revealed that the NRAS 3'UTR exists in a 3642 nt polyadenylated 3'UTR version, utilizing an alternative polyadenylation and cleavage site, 2491 nt downstream of the first. This presumably corresponds to the long NRAS form. The sequence was deposited with accession numbers AY941100 and AY941101.

Results

Figure 5A:
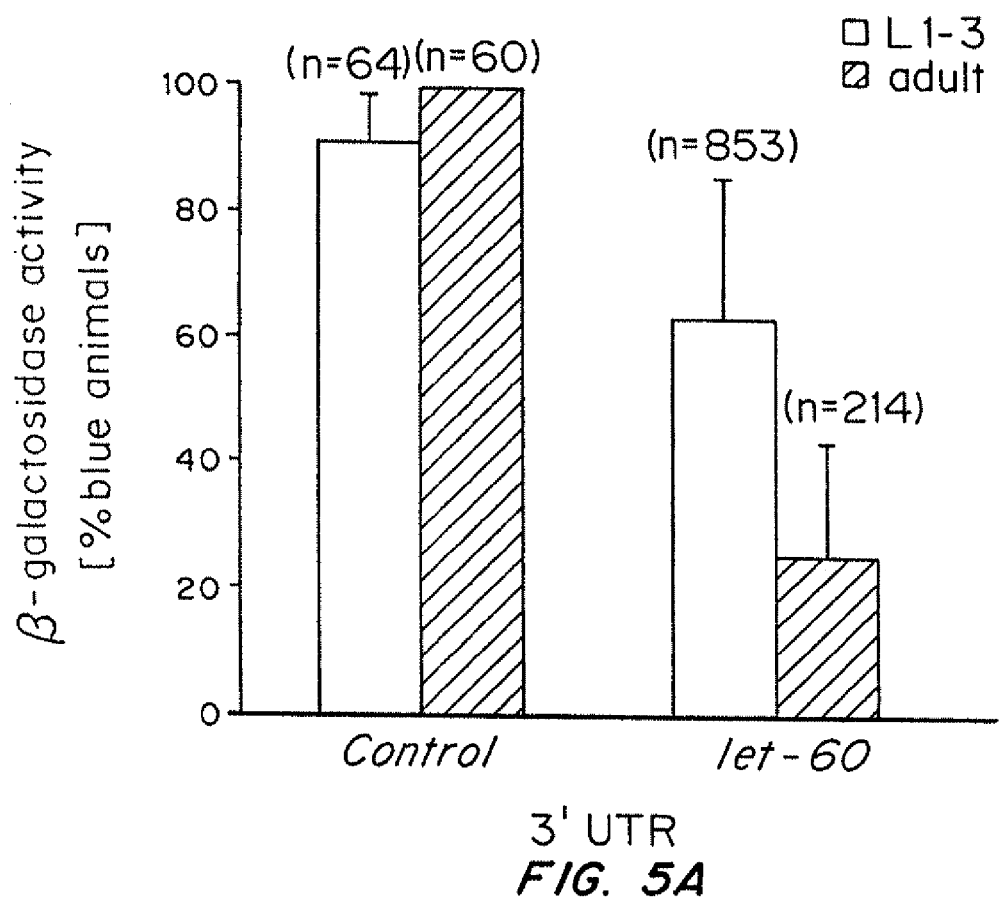
FIG. 5A is a graph of the quantitative analysis of the expression pattern from five independent wild-type transgenic lines grown at 20° C. At least 25% repression was observed in all lines. A non-regulated lin-41 3'UTR missing its LCSs (pFS1031), tested in duplicate is shown as a control.
Figure 5B:
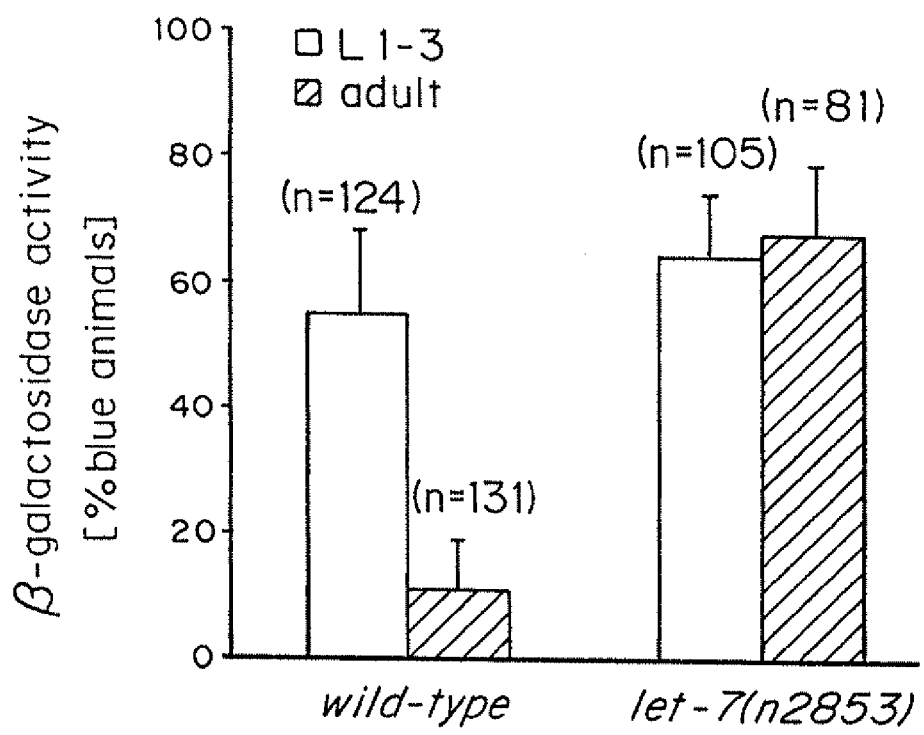
FIG. 5B is a graph depicting the down-regulation of the reporter gene expression is lost in let-7(n2853) mutant worms grown at the permissive temperature, 15° C. The parental (N2) line was tested in triplicate; four isogenic let-7(n2853) mutant lines were tested. Error bars represent standard deviations.
Figure 11:
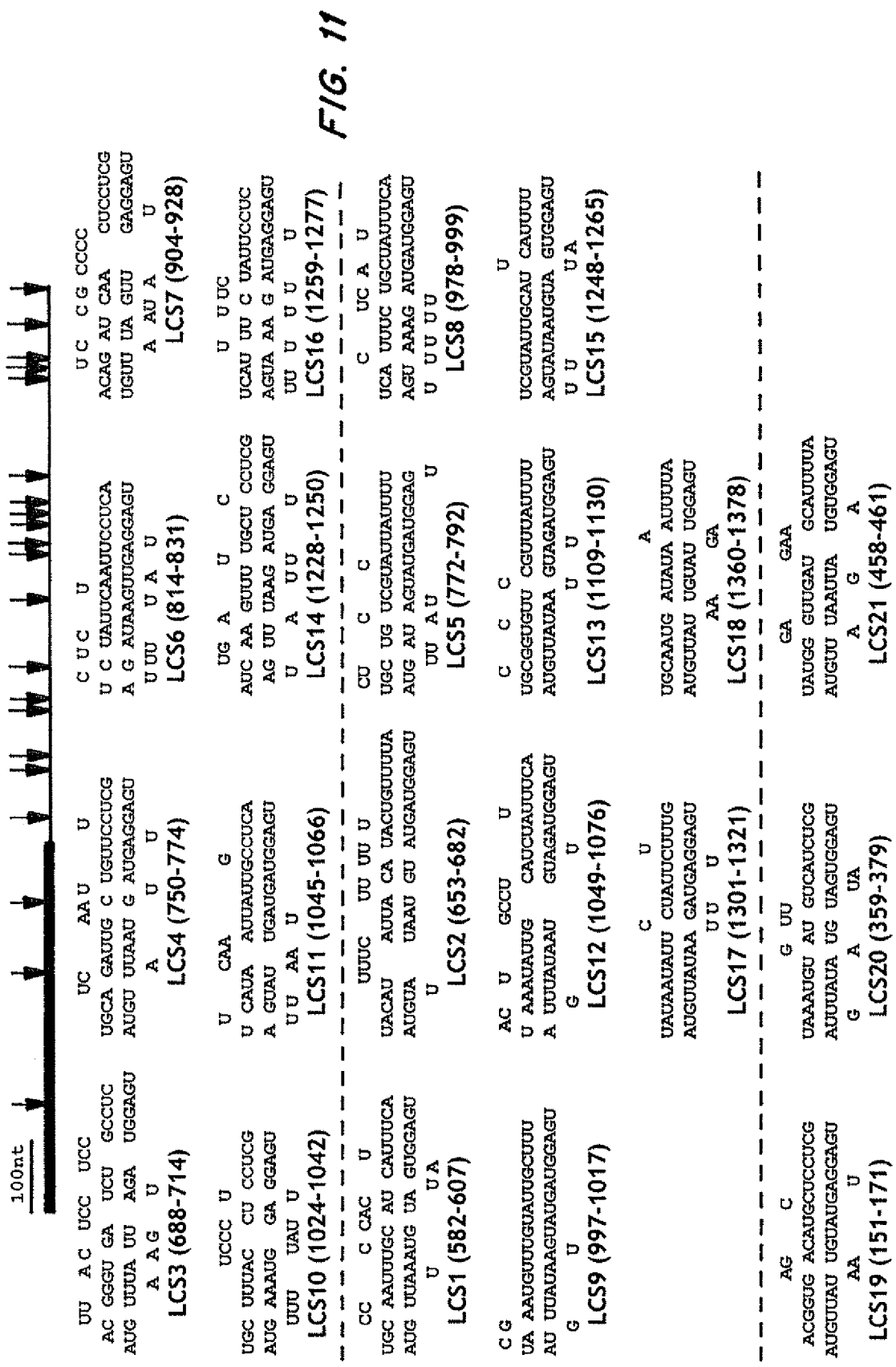
FIG. 11 depicts potential LCSs (SEQ ID Nos. 60, 61, 62, 63, 64, 65, 66, 67, 68, 69, 70, 71, 72, 73, 74, 75, 76, 77, 78, 79 and 80) in let-60/RAS in C. elegans mRNA.

Additional targets including let-60/RAS of the let-7 miRNA in *C. elegans*. The let-7 miRNA is temporally expressed in *C. elegans* (Johnson et al., (2003) Nature 426, 845-849; Pasquinelli et al., (2000) Nature 408, 86-89; Reinhart et al., (2000) Nature 403, 901-906) where it down-regulates at least two target genes, lin-41 (Slack et al., (2000) Molec Cell 5, 659-669) and hbl-1 (Abrahante et al., (2003) Dev Cell 4, 625-637; Lin et al., (2003) Dev Cell 4, 639-650), mutations which lead to precocious terminal differentiation of seam cells. To better understand the role of let-7 in *C. elegans* seam cell differentiation and its potential role in humans, additional targets of let-7 were identified. A computational screen for *C. elegans* genes was performed with let-7 family complementary sites (LCS) in their 3'UTR (Grosshans, H., et al., Dev Cell (2005) 8(3):321-30). One of the top scoring genes was let-60, encoding the *C. elegans* orthologue of the human oncogene RAS. 8 LCSs were identified in the 3'UTR of let-60 with features resembling validated LCSs (Lin et al., (2003) Dev Cell 4, 639-650; Reinhart et al., (2000) Nature 403, 901-906; Slack et al., (2000) Molec Cell 5, 659-669; Vella et al., (2004) Genes Dev 18, 132-137) (FIG. 4A) (SEQ ID Nos. 26, 27, 28, 29, 32, 33, 34 and 35). Many of the identified sites were found in the 3'UTR of let-60 from the closely related nematode *C. briggsae* (Stein et al., (2003) PLoS Biol 1, E45) (FIG. 4A, FIG. 11 and FIG. 12), suggesting that they are likely to be biologically significant. An additional three sites were found in the let-60/RAS coding sequence as well as 10 other non-conforming 3'UTR sites that may also bind to let-7 family miRNAs (FIG. 11) (SEQ ID Nos. 60, 61, 62, 63, 64, 65, 66, 67, 68, 69, 70, 71, 72, 73, 74, 75, 76, 77, 78, 79 and 80).

let-7(n2853ts) loss of function (lf) mutants express reduced let-7 miRNA and die by bursting at the vulva at the non-permissive temperature (Reinhart et al., (2000); Slack et al., (2000) Molec Cell 5, 659-669). Loss of function mutations in two previously identified targets of let-7, lin-41 and hbl-1, have the property of partially suppressing the let-7 lethal phenotype (Abrahante et al., (2003) Dev Cell 4, 625-637; Lin et al., (2003) Dev Cell 4, 639-650; Reinhart et al., (2000) Nature 403, 901-906; Slack et al., (2000) Molec Cell 5, 659-669). It was found that post-embryonic reduction of function of let-60 by feeding RNA interference (RNAi), also partially suppressed let-7(n2853) in a reproducible manner. While 5% of let-7 mutants grown on control RNAi survived at the non-permissive temperature of 25° C. (n=302), 27% of let-7(n2853); let-60(RNAi) animals survived (n=345). Thus, similar to other known let-7 targets, let-60 lf partially suppresses the let-7(n2853) lethal phenotype, suggesting that let-7 lethality may at least partially be caused by over-expression of let-60. However let-60(RNAi) did not appear to suppress the let-7 seam cell terminal differentiation defect and did not cause precocious seam cell terminal differentiation. In addition, wild-type animals subjected to let-60(RNAi) did not display typical lethal and vulvaless phenotypes associated with let-60 alleles (Beitel et al., (1990) Nature 348, 503-509; Han et al., (1990) Genetics 126, 899-913; Han and Sternberg, (1990) Cell 63, 921-931). let-60(RNAi) resulted in approximately 80% knock down of let-60 mRNA (Grosshans, H., et al., (2005) Dev Cell 8(3):321-30), suggesting that the remaining let-60 is still sufficient for seam cell differentiation and vulval development. To verify the specificity of the let-60 (RNAi), it was shown that while let-7(mn112) adults all die, let-60(n2021); let-7(mn112) adults can live (see Experimental Procedures). Interestingly, let-7(n2853); let-60(RNAi) animals delivered a brood and could lay some eggs, suggesting that the vulval bursting phenotype of let-7 was not suppressed merely because of the lack of a vulva.

let-60 and let-7 are both expressed in hypodermal seam cells (Dent and Han, 1998 Post-embryonic expression pattern of *C. elegans* let-60 ras reporter constructs. Mech Dev 72, 179-182; Johnson et al., 2003 A microRNA controlling left/right neuronal asymmetry in *Caenorhabditis elegans*. Nature 426, 845-849). The let-60 3'UTR was fused behind the *Escherichia coli* lacZ gene driven by the hypodermally-expressing col-10 promoter. It was found that reporter gene activity is down-regulated around the L4 stage (FIG. 5A), around the same time that let-7 is expressed in the seam cells (Johnson et al., (2003) Nature 426, 845-849). In contrast, the same reporter gene fused to an unregulated control 3'UTR was expressed at all stages (FIG. 5A) (Reinhart et al., (2000) Nature 403, 901-906; Slack et al., (2000) Molec Cell 5, 659-669; Vella et al., (2004) Genes Dev 18, 132-137; Wightman et al., (1993) Cell 75, 855-862). It was found that reporter down-regulation directed by the let-60 3'UTR depended on a wild-type let-7 gene, since down-regulation failed in let-7(n2853) mutants (FIG. 5B). Thus, multiple lines of evidence strongly suggest that let-60 is negatively regulated by let-7. First, the let-60 3'UTR contains multiple elements complementary to let-7; second, the let-60 3'UTR directs down-regulation of a reporter gene in a let-7 dependent manner; third, this down-regulation is reciprocal to let-7 up-regulation in the hypodermis; and finally, let-60 loss of function partially suppresses the let-7 lethal phenotype.

Figure 6A:
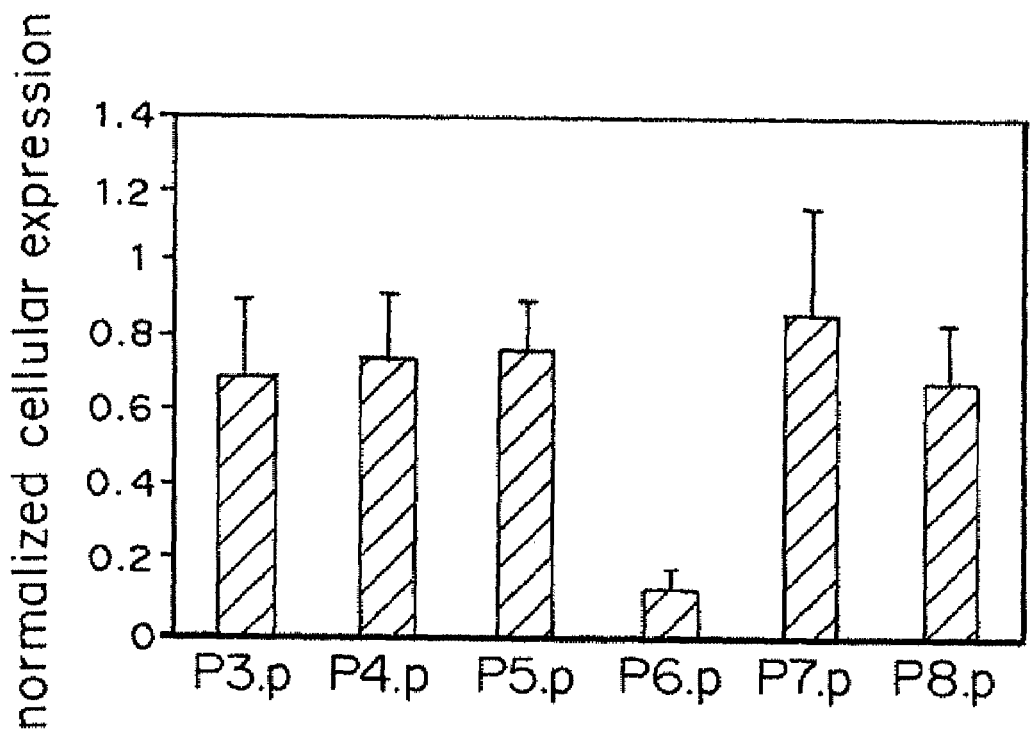
FIGS. 6A-C are graphs of the quantification of expression data. gfp54 is a fusion of gfp to the unc-54 3'UTR, driven by the lin-31 promoter. Error bars represent standard deviations.
Figure 6B:
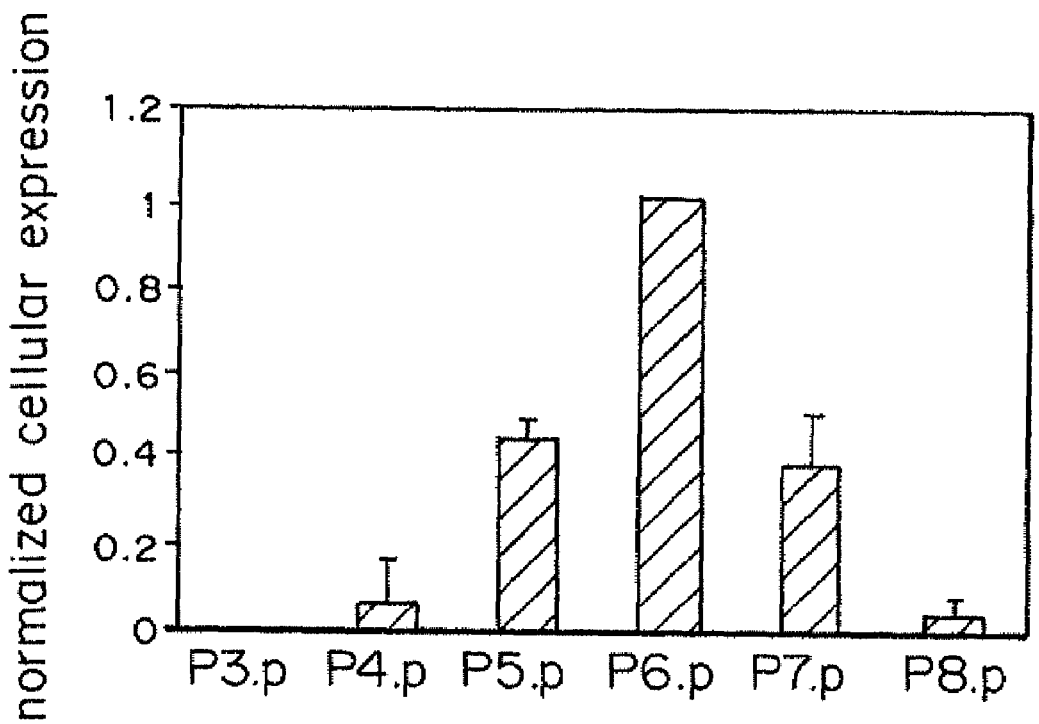
Figure 6C:
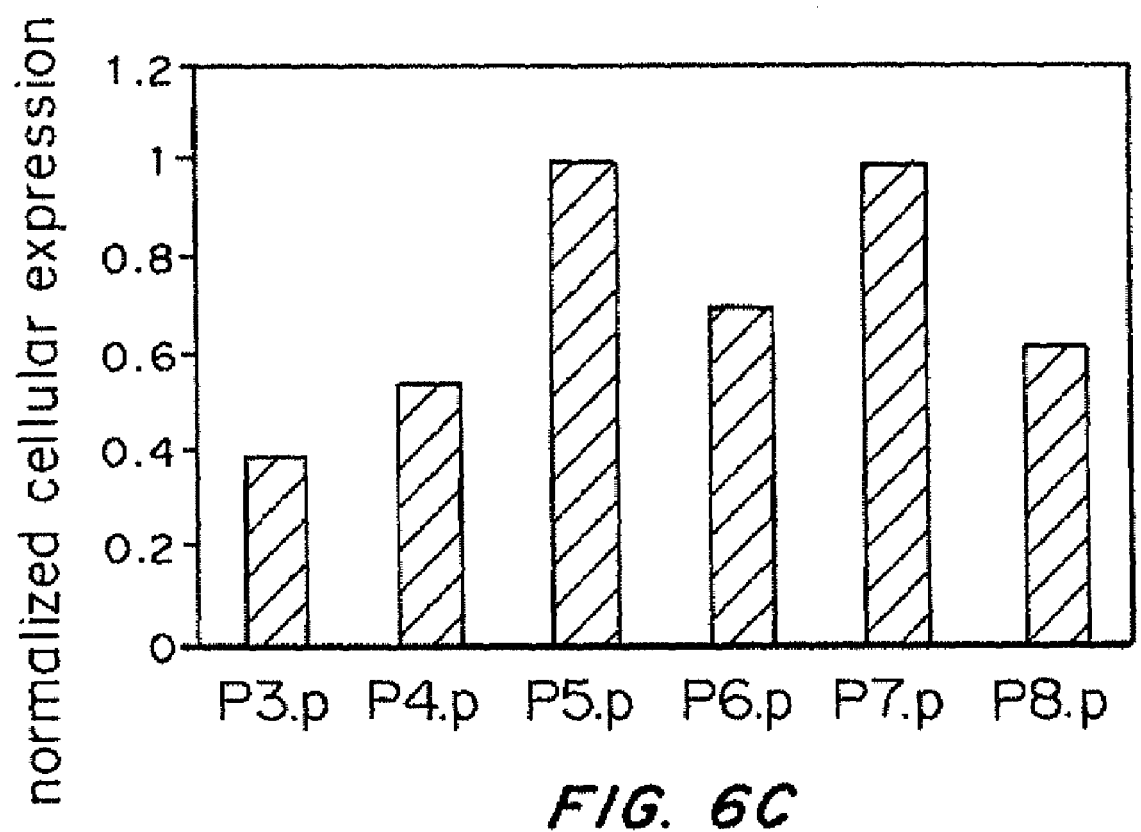

The let-7 family member mir-84 is dynamically expressed in the vulval precursor cells. let-60/RAS is best understood for its role in vulval development (Wang and Sternberg, (2001) Curr Top Dev Biol 51, 189-220), however let-7 has not been reported to be expressed in the vulva. In *C. elegans*, let-7>mir-48, mir-84 and mir-241 comprise the let-7 family (Lau et al., (2001) Science 294, 858-862; Lim et al., (2003) Genes Dev 17, 991-1008; Reinhart et al., (2000) Nature 403, 901-906) (FIGS. 10A, 10B). Previous work demonstrated that a let-7::gfp fusion faithfully recapitulates the temporal expression of let-7 and is temporally expressed in seam cell tissues affected in the let-7 mutant (Johnson et al., (2003) Dev Biol 259, 364-379). The expression pattern of mir-84, the closest let-7 relative, was examined by fusing 2.2 kilobases (Kb) of genomic sequence immediately upstream of the miR-84 encoding sequence to the green fluorescent protein (gfp) gene. mir-84::gfp was first observed in the somatic gonad in larval stage 1 (L1). In L3 animals, strong expression was observed in uterine cells including the anchor cell (AC), and weak dynamic expression was observed in the vulval precursor cells (VPCs) (FIGS. 6A-C). VPCs are multipotent ventral hypodermal cells that generate the vulva during L3 and later stages (Sulston and Horvitz, (1977) Dev Biol 56, 110-156). VPCs adopt one of three fates depending on EGF signaling from the AC (Wang and Sternberg, (2001) Curr Top Dev Biol 51, 189-220). The cell closest to the AC, P6.p, receives the most LIN-3/EGF signal (Katz et al., (1995) Cell 82, 297-307) and adopts the primary ($1°$) fate through activation of a RAS/MAPK signal transduction pathway (Beitel et al., (1990) Nature 348, 503-509; Han et al., (1990) Genetics 126, 899-913; Han and Sternberg, (1990) Cell 63, 921-931): P5.p and P7.p receive less LIN-3 as well as receiving a secondary lateral signal (Sternberg, (1988) Nature 335, 551-554) from P6.p, and adopt the secondary ($2°$) fate: P3.p, P4.p and P8.p adopt the uninduced tertiary ($3°$) fate. mir-84::gfp expression was observed during the early to mid L3 stage in all the VPCs except for P6.p, in which expression was rarely observed (FIG. 6A). Subsequent VPC expression in the mid to late L3 stage was restricted to the daughters (Pn.px) of P5.p and P7.p with weaker GFP first appearing in the P6.p daughters just before their division into P6.pxx. Thereafter, equivalent expression was observed in the granddaughters (Pn.pxx) of P5.p, P6.p and P7.p. mir-84::gfp expression was observed in all the VPCs except for P6.p at the stage when their fate in vulval development is determined by signaling from the AC (Ambros, (1999) Development 126, 1947-1956) suggesting that mir-84 could play a role in vulval cell fate determination. In the L4 stage, GFP expression was maintained in the AC and other uterine cells, appeared weakly in hypodermal seam cells, and was up-regulated to higher levels in many P5.p-P7.p descendants. A second let-7 family member, mir-48 was also expressed in non-P6.p VPCs, suggesting the potential for redundancy between mir-48 and mir-84 in the VPCs.

mir-84 overexpression causes vulval and seam defects. miR-84 was overexpressed by generating transgenic animals harboring a multi-copy array of a 3.0 Kb genomic DNA fragment that spans from 2.2 Kb upstream to 0.8 Kb downstream of the miR-84 encoding sequence (called mir-84 (+++)). These animals expressed elevated levels of miR-84 and displayed abnormal vulval development phenotypes, including protrusion and bursting of the vulva (40% of animals, n=40). Consistent with mir-84::gfp expression in seam cells, it was found that mir-84(+++) animals also exhibited precocious seam cell terminal differentiation and alae formation in the L4 stage, a characteristic seen in precocious developmental timing mutants. In fact, let-7 over-expressing strains also exhibit precocious seam cell terminal differentiation in the L4 stage (Reinhart et al., (2000) Nature 403, 901-906). In contrast, animals carrying an array containing a construct identical to mir-84(+++) except for a 75 nucleotide (nt) deletion of sequences encoding the predicted pre-mir-84 (Δmir-84 (+++)) did not display any vulval or seam defects, demonstrating that the phenotypes observed in mir-84(+++) are dependent on the miR-84 sequence.

A search was conducted for let-7 family miRNA complementary sequences (LCS) in the 3'UTRs of all genes known to play a role in vulval development (Table 2). LCSs have the potential to bind all members of the let-7 family, including mir-84. Approximately 11 vulval genes contained at least one LCS (Table 2), raising the possibility that the let-7 family may regulate multiple genes in the vulva. In this analysis though, let-60/RAS stood out due to the high number of LCS sites.

TABLE 2

LCSs in the 3'UTRs of Known Vulval Genes

Figure 13A:
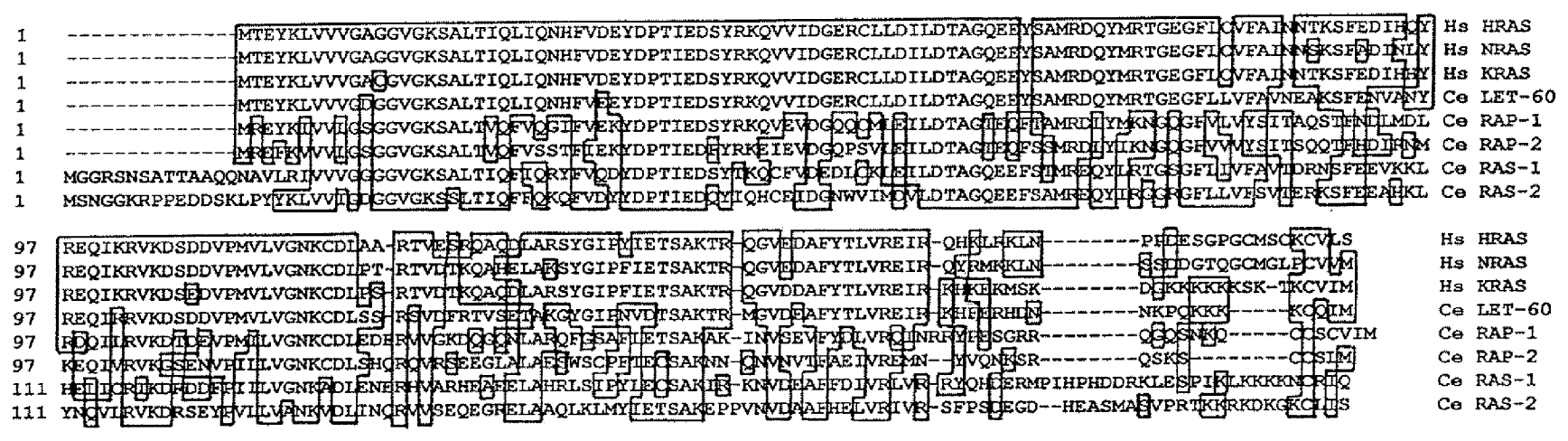

| Gene | Chromosome | LCS in 3'UTR |
| --- | --- | --- |
| eor-1 | IV | Yes |
| had-1 | V | Yes |
| let-60 | IV | Yes |
| lin-3 | IV | Yes |
| lin-9 | III | Yes |
| lin-11 | I | Yes |
| lin-36 | III | Yes |
| lin-39 | III | Yes |
| lin-45 | IV | Yes |
| mpk-1 | III | Yes |
| sem-5 | X | Yes | mir-84 overexpression partially suppresses let-60/RAS gain of function phenotypes. let-60/RAS is active in P6.p following a lin-3 EGF signal from the anchor cell that activates a MAPK signal transduction cascade transforming P6.p to the 1° vulval fate (Han and Sternberg, (1990) Cell 63, 921-931). Since mir-84 is expressed in all VPCs except P6.p, the possibility that mir-84 negatively regulates expression of let-60/RAS in cells not destined to adopt the 1° fate was examined. Activating mutations in let-60/RAS cause multiple VPCs (including the non-P6.p VPCs) to adopt 1° or 2° fates leading to a multivulva (Muv) phenotype (Han et al., 1990). It was found that over-expression of mir-84 partially suppressed the Muv phenotype of let-60(gf) mutations. In the study, 41% (n=51) of let-60(ga89) (Eisenmann and Kim, (1997) Genetics 146, 553-565) animals displayed a Muv phenotype, while only 13% (n=168) did so when also over-expressing mir-84 from a multi-copy array ($p \ll 0.0001$ Chi square test). The same suppression was observed with a second let-60(gf) allele, let-60(n1046) (Han et al., (1990) Genetics 126, 899-913): 77% (n=39) of let-60(n1046) animals displayed a Muv phenotype, while only 50% (n=113) did so when also over-expressing mir-84 ($p \ll 0.0001$ Chi square test). let-60 (n1046) animals displayed an average of 1.54 pseudovulvae per animal compared to an average of 0.66 pseudovulvae per let-60(n1046) animal over-expressing mir-84. For both let-60 (gf) alleles, animals exhibiting low mosaicism for the myo-3::gfp co-injection marker, were completely suppressed, suggesting that the partial suppression was likely due to mosaicism of the transgeneic array. Neither an empty vector control (TOPO) (n=111) (p=0.1435 Chi square test), nor the Δmir-84 (+++) array (n=129), suppressed the Muv phenotype of let-60(n1046). For all let-60(gf) experiments, three independent lines behaved similarly (FIG. 13C).

The let-60/RAS 3'UTR confines expression to P6.p. The promoter of let-60/RAS drives reporter expression in all VPCs (Dent and Han, (1998) Mech Dev 72, 179-182). However, the transgenic reporters used in this earlier work did not include the let-60 3'UTR. GFP was fused to the let-60 3'UTR and drove GFP expression in all the VPCs using the VPC-specific lin-31 (Tan et al., (1998) Cell 93, 569-580) promoter (gfp60). In the late L2 and early L3 stages, GFP was expressed in all the Pn.p cells, but by mid to late L3 stages, GFP was largely restricted to the P6.p cell (FIG. 6B), with some expression in the P5.p and P7.p cell descendants. A similar fusion construct in which the let-60 3'UTR was replaced by the unregulated unc-54 3'UTR showed GFP expression in all Pn.p cells (FIG. 6C). Since the lin-31 promoter is active in all Pn.p cells (Tan et al., (1998) Cell 93, 569-580), this result demonstrates that the let-60/RAS 3'UTR is sufficient to down-regulate a reporter gene in the non-P6.p cells.

The let-60 3'UTR was replaced with the unregulated unc-54 3'UTR in a let-60 genomic DNA fragment. While one could generate viable lines using a let-60::let-60(+)::let-60 3'UTR construct at 10 ng/μl, it was not possible to generate viable transformants using this let-60::let-60(+)::unc-54 3'UTR construct, even at 0.1 ng/μl. The results suggest that the removal of the let-60 3'UTR may severely over-express let-60 and cause lethality.

let-60/RAS is a likely target of mir-84 in the vulva. Previous work has demonstrated that VPCs are sensitive to the levels of let-60/RAS (Beitel et al., (1990) Nature 348, 503-509; Han et al. (1990)). Animals carrying extra copies of the wild-type let-60/RAS gene display a Muv phenotype, where non-P6.p VPCs can adopt the 1° fate. The data strongly suggest that mir-84 negatively regulates let-60 in non-P6.p VPCs. First, mir-84 is complementary to multiple sites in the let-60 3'UTR. Second, mir-84 is expressed in a reciprocal manner to let-60 in the VPCs. miR-84 is largely absent from P6.p, at the same time as the let-60 3'UTR confines GFP expression mainly to the P6.p cell lineage. Finally, mir-84 over-expression partially suppresses the effects of activating mutations in the let-60 gene. mir-84 modulates the expression of let-60/RAS in non-P6.p VPCs to reduce flux through the RAS/MAPK signaling pathway and hence decrease the likelihood that these cells will also adopt the 1° fate. However, mir-84 is clearly not the only regulator of let-60/RAS in non-P6.p cells: daf-12(rh61) mutants do not express mir-84 in any VPC (n=60 animals), and yet daf-12(rh61) animals do not display a Muv phenotype. Other known factors, e.g. synmuv genes, (Berset et al., (2001) Science 291, 1055-1058; Ceol and Horvitz, (004) Dev Cell 6, 563-576; Hopper et al., (2000) Mol Cell 6, 65-75; Lee et al., (1994) Genes Dev 8, 60-73; Wang and Sternberg, (2001) Curr Top Dev Biol 51, 189-220; Yoo et al., (2004) Science 303, 663-666; Yoon et al., (1995) Science 269, 1102-1105) or unknown factors may also regulate let-60/RAS signaling in these cells.

The combined results provide strong evidence that let-7 and mir-84 regulate let-60/RAS expression through its 3'UTR in seam and vulval cells, cells in which they are all naturally expressed. Given that the 3'UTR of let-60/RAS contains multiple let-7/mir-84 complementary sites, it is expected that this regulation is direct.

let-7 complementary sites in human RAS 3'UTRs. Numerous miRNAs are altered in human cancers (Calin et al., (2002) Proc Natl Acad Sci U S A 99, 15524-15529; Calin et al., (2004) Proc Natl Acad Sci USA 101, 2999-3004; Michael et al., (2003) Mol Cancer Res 1, 882-891; Tam et al., (2002) J Virol 76, 4275-4286) and three of the best understood miRNAs, lin-4 (Lee et al., (1993) Cell 75, 843-854), let-7 (Reinhart et al., (2000) Nature 403, 901-906) and bantam (Brennecke et al., (2003) Cell 113, 25-36), all regulate cell proliferation and differentiation. The closest human homologues of let-7 and mir-84 are the H.s. let-7 family miRNAs (Lagos-Quintana et al., (2002) Curr Biol 12, 735-739; Pasquinelli et al., (2000) Nature 408, 86-89). let-60/RAS (SEQ ID No. 87) is the C. elegans orthologue of human HRAS (SEQ ID No. 84), KRAS (SEQ ID No. 86), and NRAS (SEQ ID No. 85) (FIGS. 13A-B), which are commonly mutated in human cancer (Malumbres and Barbacid, (2003) Nat Rev Cancer 3, 459-465), including lung cancer. It was found that all three human RAS 3'UTRs contain multiple putative let-7 complementary sites with features of validated C. elegans LCSs (SEQ ID Nos. 36, 37, 38, 40, 41, 42, 43, 44, 45, 46, 55) (FIGS. 4B-D). Many of these are conserved in rodents, amphibians and fish (FIG. 14 and FIG. 15 (SEQ ID Nos. 97, 98, 99, 100, 101, 102, 103), suggesting functional relevance. The presence of putative LCSs in human RAS 3'UTRs indicates that mammalian let-7 family members may regulate human RAS in a manner similar to the way let-7 and mir-84 regulate let-60/RAS in C. elegans.

Figure 7A:
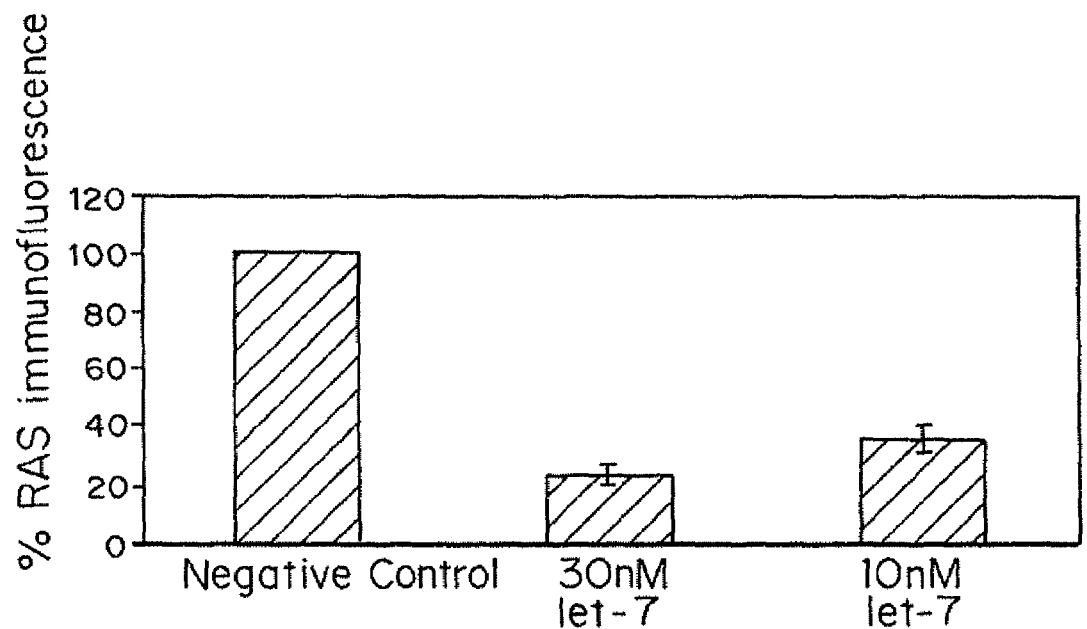
FIGS. 7A and B are graphs showing that the presence of let-7 influences the expression of RAS in human cells. HEPG2 cells were transfected with 10 and 30 nM of a let-7 or negative control precursor miRNA. Immunofluorescence using an antibody specific to NRAS, VRAS, and KRAS revealed that the let-7 transfected cells have much lower levels of the RAS proteins.
Figure 16A:
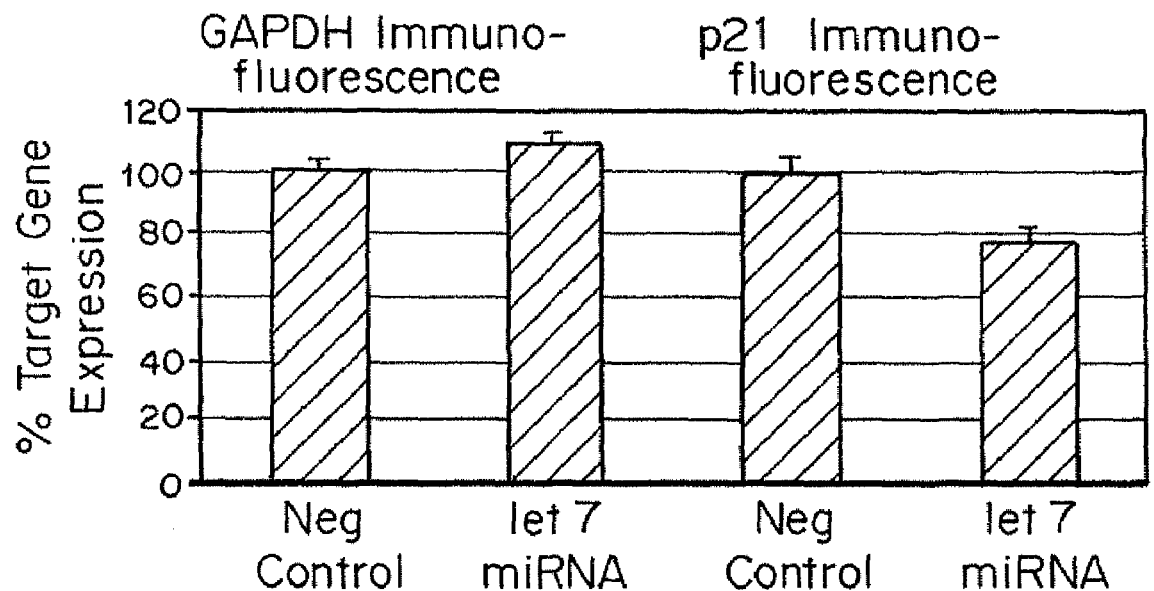
FIGS. 16A and 16B show that the presence of let-7 does not influence the expression of control proteins in human cells.
Figure 16B:
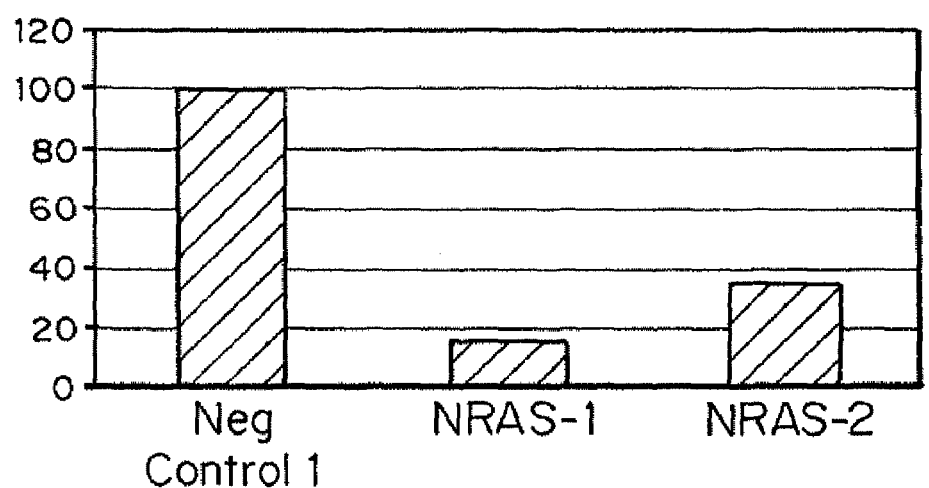

Human RAS expression is regulated by let-7 in cell culture. Microarray analysis performed by Ambion, Inc. on six different cell lines revealed that HepG2 cells express let-7 at levels too low to detect by microarray analysis. Therefore, by request, Ambion, Inc., transfected HepG2 cells with a double-stranded (ds) RNA that mimics the let-7a precursor. Consistent with the prediction that RAS expression is negatively regulated by let-7, immunofluorescence with a RAS-specific antibody revealed that the protein is reduced by approximately 70% in HepG2 cells transfected with exogenous let-7a miRNA relative to the same cells transfected with a negative control miRNA (FIG. 7A). The protein expression levels of GAPDH and $p21^{CIP1}$ were largely unaffected by the transfected let-7a and negative control pre-miRNAs (FIG. 16A), indicating that let-7a regulation is specific to RAS. To confirm that the RAS antibody is specific to RAS protein in the transfected cells, HepG2 cells were also independently transfected with two exactly complementary siRNAs targeting independent regions of NRAS. Both siRNAs reduced cell fluorescence by more than 60% as compared to negative control siRNA-transfected cells (FIG. 16B).

Figure 7B:
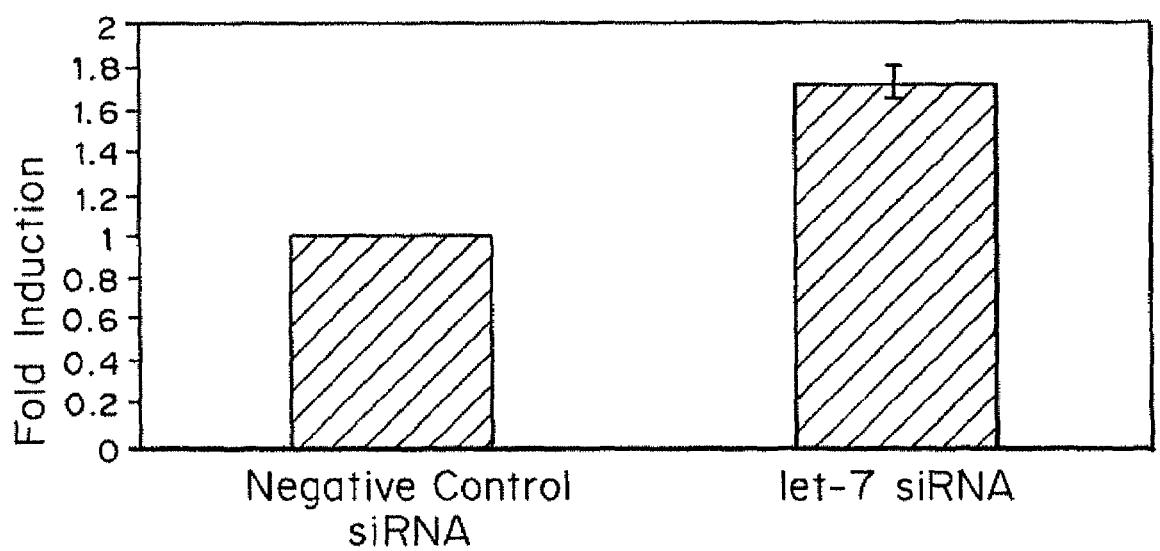
FIG. 7B is a graph of the quantification of the RAS antibody fluorescence from replicates of the transfections.

It was predicted that cells expressing native let-7 may express less RAS protein and that inhibition of let-7 may lead to derepression of RAS expression. To test this, by request, Ambion, Inc. transfected HeLa cells, which express endogenous let-7 (Lagos-Quintana et al., (2001) Science 294, 853-858; Lim et al., (2003) Genes Dev 17, 991-1008), with antisense molecules designed to inhibit the activity of let-7 (Hutvagner et al., (2004) PLoS Biol 2, E98; Meister et al., (2004) RNA 10, 544-550). Reducing the activity of let-7 in HeLa cells resulted in an about 70% increase in RAS protein levels (FIG. 7B). These results, combined with the reciprocal experiment using pre-let-7 miRNAs discussed above, indicates that let-7 negatively regulates the expression of RAS in human cells.

Figure 8A:
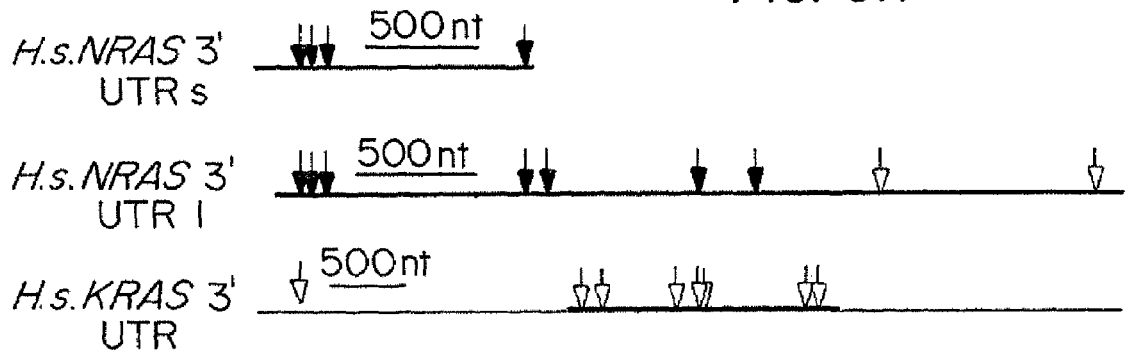
FIGS. 8A-C depict that the 3'UTRs of NRAS and KRAS enable let-7 regulation.
Figure 8B:
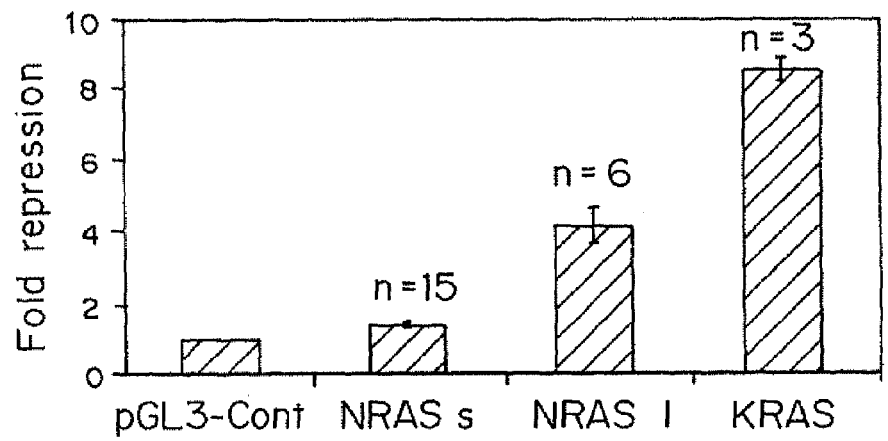

The 3'UTR of human NRAS and KRAS was fused to a luciferase reporter gene and these constructs transfected along with transfection controls into HeLa cells. NRAS contains two naturally occurring 3'UTRs that utilize alternative polyadenylylation and cleavage sites, such that one of the 3'UTRs is 2.5 kb longer than the other. It was found that while the long NRAS 3'UTR strongly repressed reporter expression compared to an unregulated control 3'UTR (FIGS. 8A-B), the short NRAS 3'UTR led to only slight, but reproducible, repression of the reporter. The short 3'UTR contains 4 LCSs, while the long form contains 9 LCSs. The KRAS 3'UTR also repressed the luciferase reporter (FIG. 5A-B), while HRAS was not tested. The results demonstrate that the 3'UTRs of NRAS and KRAS contain regulatory information, sufficient to down-regulate the reporter.

Figure 8C:
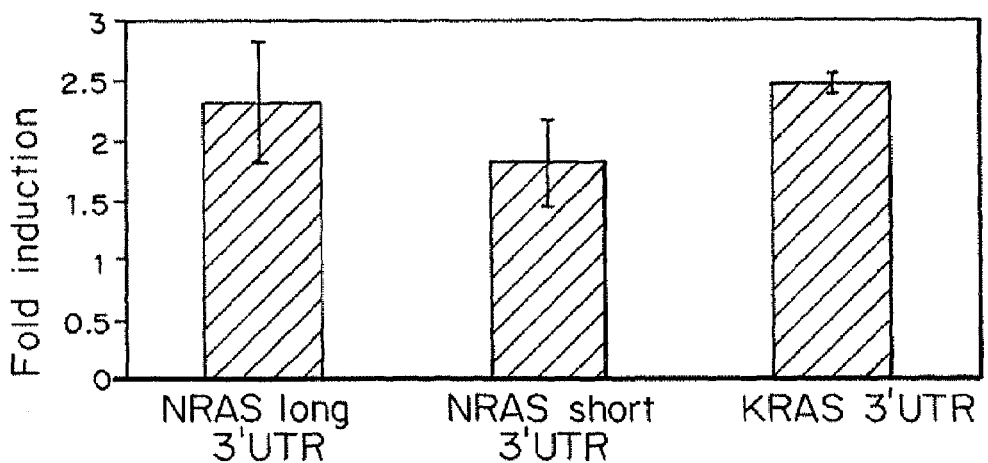
Figure 17:
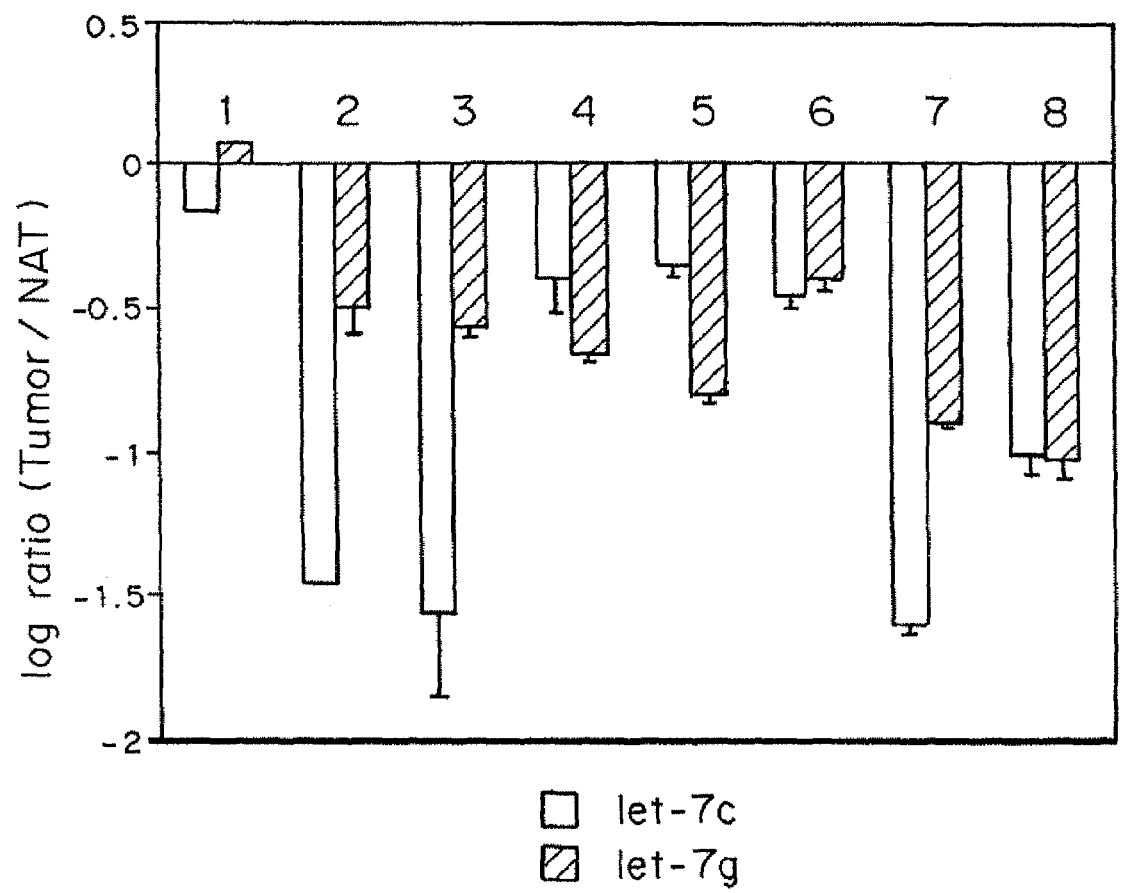
FIG. 17 is a graph of the expression of let-7c and let-7g in lung tumors relative to associated normal adjacent tissue (NAT).

As with the endogenous RAS experiments described above, the reciprocal experiment was performed wherein HeLa cells were transfected with the RAS 3' UTR reporter constructs and the let-7a anti-sense inhibitor molecule (or a control scrambled molecule). Cells transfected with the let-7a inhibitor relieved repression exerted on the reporter relative to the control transfections (FIG. 8C). Since, a loss in the extent of down-regulation is observed when let-7 is inhibited, these results strongly indicate that let-7 regulates NRAS and KRAS in human cells through their 3'UTRs.

let-7, RAS and lung cancer. Like let-60/ras, human RAS is dose-sensitive, since over-expression of RAS results in oncogenic transformation of human cells (McKay et al., (1986) Embo J 5, 2617-2621; Pulciani et al., (1985) Mol Cell Biol 5, 2836-2841). It is plausible that loss of miRNA control of RAS could also lead to over-expression of RAS and contribute to human cancer. Recent work has mapped let-7 family members to human chromosomal sites implicated in a variety of cancers (Calin et al., (2004) Proc Natl Acad Sci USA 101, 2999-3004). In particular let-7a-2 let-7c and let-7g have been linked to small chromosomal intervals that are deleted in lung cancers (Calin et al., (2004) Proc Natl Acad Sci USA 101, 2999-3004), a cancer type in which RAS mis-regulation is known to be a key oncogenic event (Ahrendt et al., (2001) Cancer 92, 1525-1530; Johnson et al., (2001) Nature 410, 1111-1116).

miRNA microarray analysis was performed by Ambion, Inc. to examine expression levels of members of the let-7 gene family in tissue from twenty-one different cancer patients, including twelve lung cancer patients with squamous cell carcinomas (stage IB or IIA). let-7 is poorly expressed in lung tumors, as shown by expression of let-7 in 21 breast, colon, and lung tumors relative to associated normal adjacent tissue ("NAT"). Fluorescently labeled miRNA was hybridized to microarrays that included probes specific to let-7a and let-7c. Fluorescence intensities for the tumor and NAT were normalized by total fluorescence signal for all elements and the relative average signal from the let-7 probes in the tumor and normal adjacent samples are expressed as log ratios. let-7a and let-7c had similar profiles suggesting cross-hybridization between the two closely related miRNAs. let-7 miRNAs were reduced in expression in a number of the tumors relative to the normal adjacent tissue samples from the same patients. let-7 was expressed at lower levels in all of the lung tumor tissues (FIG. 9A), but only sporadically in other tumor types. A similar finding was independently discovered (Takamizawa et al., (2004) Cancer Res 64, 3753-3756). On average, let-7 was expressed in lung tumors at less than 50% of expression in the associated normal lung samples. Northern analysis was used to measure let-7c in the tumor and NAT samples for the two patients from which RNA was purified (samples represented by the first and fifth lung cancer bars in FIG. 9B). Consistent with the microarray results by Ambion, Inc., northern analysis verified that the expression of let-7c was 65% lower in the tumor of patient #1 and 25% lower in the tumor of patient #5. Seven of eight examined samples also had on average 30% less let-7g expression in the tumor tissue (FIG. 17). The miRNA arrays were used to compare the lung tumors and NAT included probes for 167 total miRNAs. The expression of the vast majority of these were unchanged in the lung tumors indicating that let-7 might be important in lung cancer. In theory, down regulation of let-7 could result in up-regulation of RAS and thus induce or accentuate oncogenesis.

To test this hypothesis, Ambion, Inc. isolated total RNA and total protein from the tumor and normal adjacent tissues of three new lung cancer patients with squamous cell carcinoma. The RNA samples were split and half was used for northern analysis to measure let-7c and U6 snRNA. The other halves of the RNA samples were used for real-time PCR to measure the NRAS mRNA, 18S rRNA, and B-actin mRNA. The protein samples were used for western analysis to assess RAS and GAPDH protein levels. RAS protein was present in the tumors at levels at least ten-fold higher than in the normal adjacent samples from the same patients. Consistent with the miRNA array results of Ambion, Inc. for other lung cancer samples, all three lung tumor samples had 4- to 8-fold lower levels of let-7 than did the corresponding NAT samples. The first and third lung cancer samples had similar levels of NRAS mRNA in both the tumor and NAT while the second sample pair had significantly higher levels of NRAS mRNA in the tumor sample. RAS protein levels correlate poorly with NRAS mRNA levels but very well with let-7 levels, suggesting that the expression of the oncogene is significantly influenced at the level of translation, consistent with the known mechanism of let-7 in invertebrates.

The reciprocal expression pattern between let-7 and RAS in cancer cells closely resembles what was seen with let-7 and RAS in *C. elegans* and in the human tissue culture experiments. The correlation between reduced let-7 expression and increased RAS protein expression in the lung tumor samples indicates that one or more members of the let-7 gene family regulates RAS expression in vivo and that the level of expression of the miRNA is an important factor in limiting or contributing to oncogenesis.

These results demonstrate that the let-7 miRNA family negatively regulates RAS in two different *C. elegans* tissues and in two different human cell lines. Strikingly, let-7 is expressed in normal adult lung tissue (Pasquinelli et al., (2000) Nature 408, 86-89), but is poorly expressed in lung cancer cell lines and lung cancer tissue (Takamizawa et al., (2004) Cancer Res 64, 3753-3756). The expression of let-7 inversely correlates with expression of RAS protein in lung cancer tissues, suggesting a possible causal relationship. In addition, over-expression of let-7 inhibited growth of a lung cancer cell line in vitro (Takamizawa et al., (2004) Cancer Res 64, 3753-3756), suggesting a causal relationship between let-7 and cell growth in these cells.

These results demonstrate that the expression of the RAS oncogene is regulated by let-7 and that over-expression of let-7 can inhibit tumor cell line growth. The combined observations that let-7 expression is reduced in lung tumors, that several let-7 genes map to genomic regions that are often deleted in lung cancer patients, that over-expression of let-7 can inhibit lung tumor cell line growth, that the expression of the RAS oncogene is regulated by let-7, and that RAS is significantly over-expressed in lung tumor samples strongly implicates let-7 as a tumor suppressor in lung tissue and provides evidence of a mechanism forming the basis for treatment.

Example 2

Expression Patterns of let-7 and mir-125, the lin-4 Homologue

It was found that both let-7 and mir-125, the lin-4 homologue, are expressed in a variety of adult tissues, with prominent expression in the lung and brain. Interestingly, both are expressed at low levels in the pancreas and testis. Past work has shown that the *C. elegans* lin-4 and let-7 miRNAs are temporally expressed (Reinhart, B., et al., (2000) 403:901-906 and Feinbaum, R. and V. Ambros, (1999) Dev Biol 210 (1):87-95). Similarly, it has been shown that the mammalian homologues for these miRNAs are also temporally expressed during mouse development. Northern blots reveal that let-7 and mir-125 have very similar expression profiles. Both become expressed at around day E9.5. Interestingly, this coincides approximately with the time of lung organogenesis, and when other major organs begin to develop.

A in situ protocol using an oligonucleotide based on the mouse sequence of the let-7c miRNA, which has been digoxigenin-labeled, has been developed. Since it has been confirmed by northern analysis that let-7c is expressed at E12.5, frozen sections taken from similarly aged embryos have been analyzed. Preliminary results show let-7 is expressed in the lung epithelium by in situ. In addition to other cancers, these results indicate that let-7 is useful as a therapeutic for lung cancer therapy because let-7 is a natural compound in lung cells.

Example 3

Effect of Inhibition and Overexpression of let-7 in Lung Cancer Cells

Figure 18A:
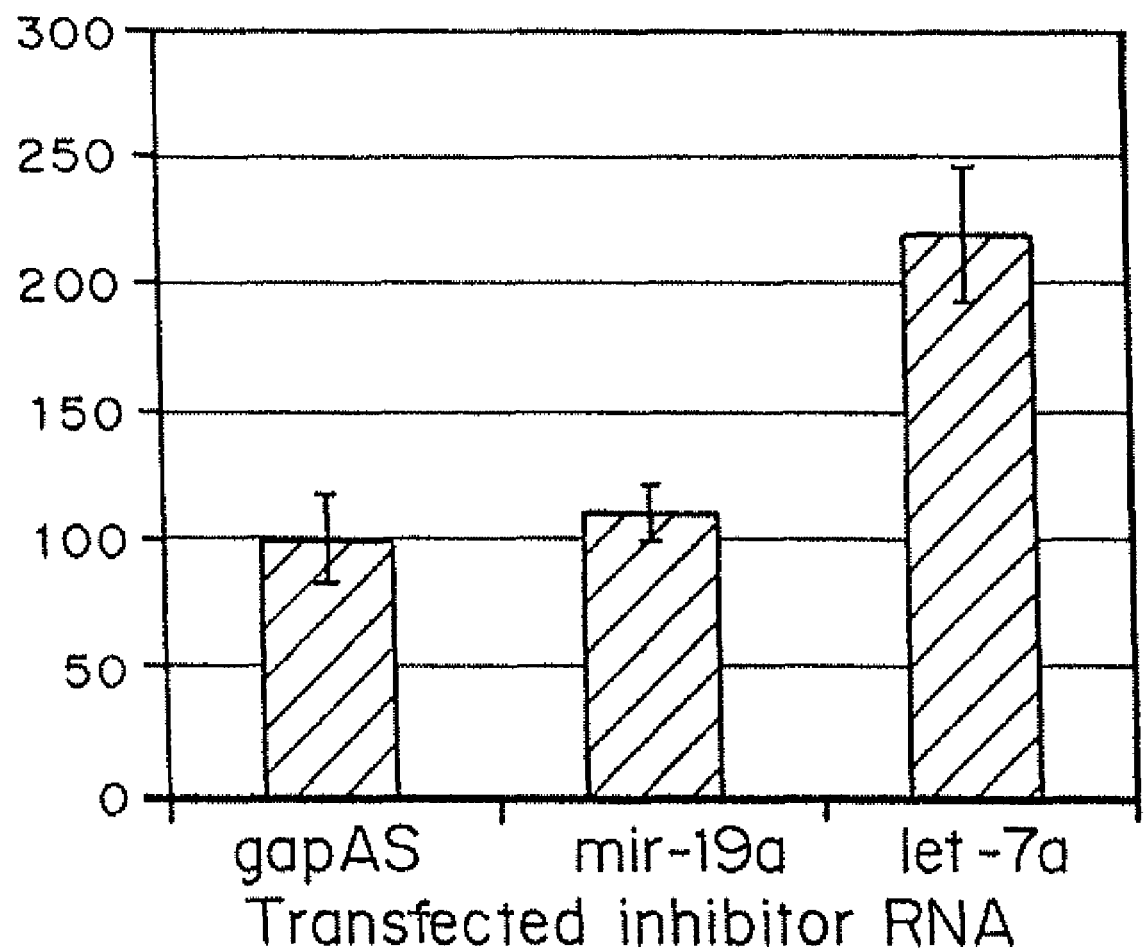
FIG. 18A is a graph of the inhibition of let-7 that results in a 100% increase of A549 cell numbers, compared to a control transfection and a control anti-miRNA (mir-19a).
Figure 18B:
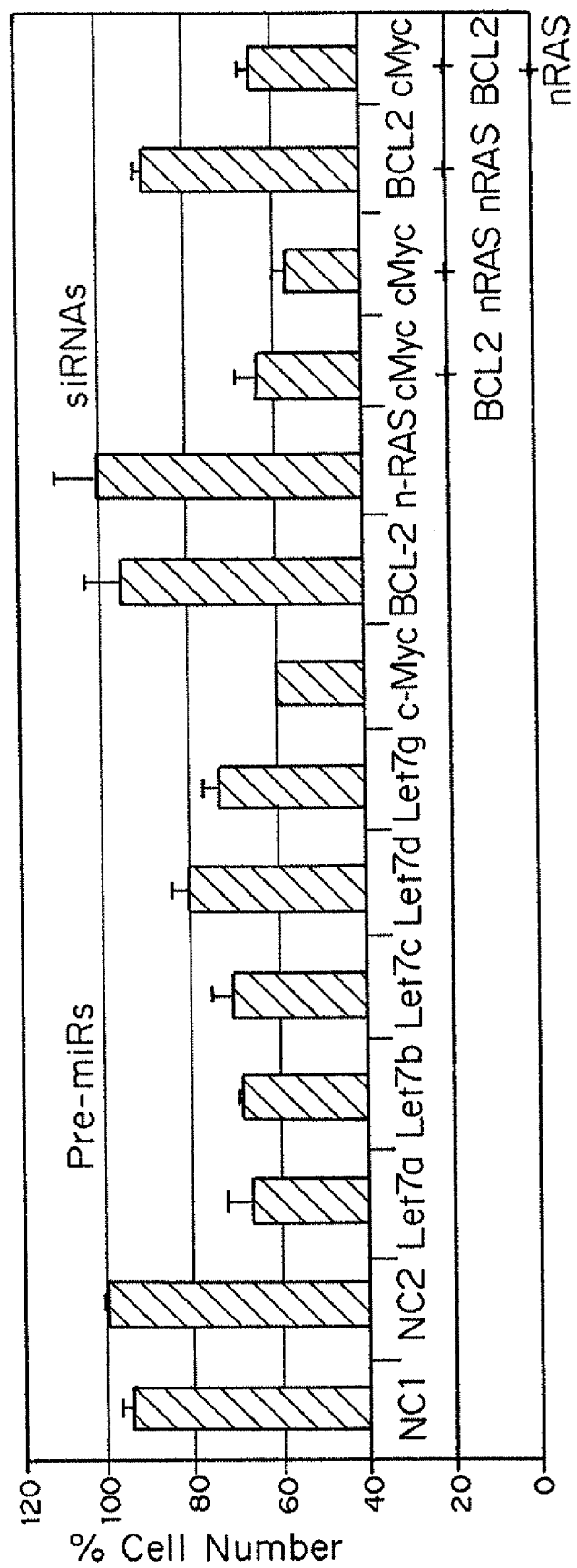
FIG. 18B is a graph of Extra let-7 that causes a decrease in A549 cell numbers compared to a control miRNA (NC).

Inhibition of let-7 function in A549 lung cancer cells via transfection (with anti-let-7 molecules) causes increased cell division of A549 lung cancer cells (FIG. 18A), while let-7 over-expression (with transfected pre-let-7) caused a reduction in A549 cell number (FIG. 18B). These results are consistent with the tumor suppressing activity of let-7. Moreover, the let-7 over-expression phenotype resembled that caused by MYC down-regulation (FIG. 18A), suggesting that the effects of let-7 on cell proliferation may also be through repression of MYC. Preliminary evidence indicates that MYC is also a direct target of let-7 in human cells. Therefore, these results indicate that let-7 may be a potential therapeutic in cancers with aberrant expression of MYC.

Figure 20A:
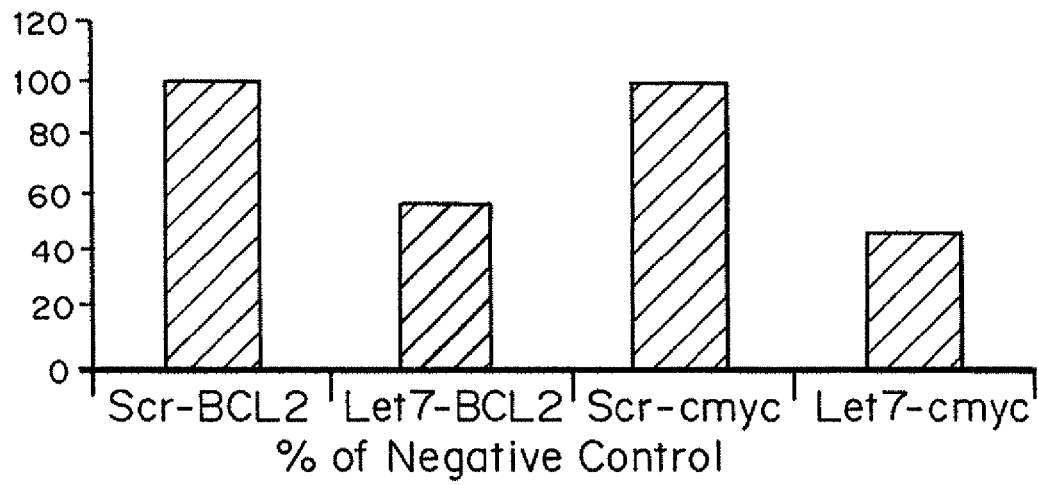
FIG. 20A is a graph of the reduced expression of MYC and BCL-2 protein in cells treated with exogenous let-7 miRNA compared to a control miRNA with a scrambled let-7 sequence.
Figure 20B:
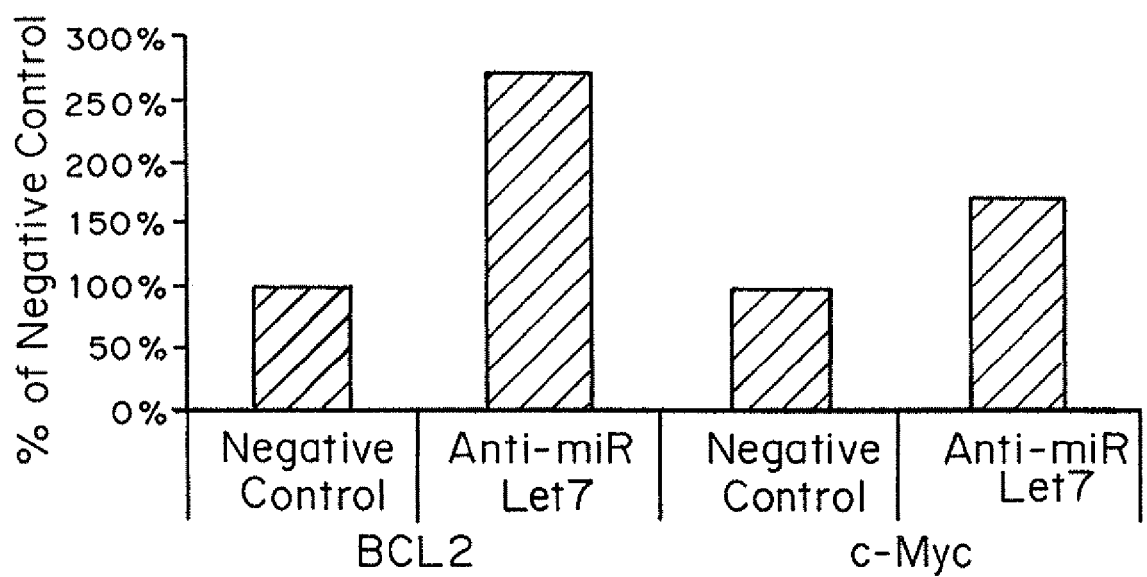
FIG. 20B is a graph of the increased expression of MYC and BCL-2 in HeLa cells transfected with an anti-let-7 molecule.

Example 4 let-7 Affects Expression of MYC and BCL-2 let-7 regulates RAS, MYC and BCL-2 protein levels, all three of which are major cancer oncogenes. Addition of let-7 to HepG2 cells (that do not make let-7 endogenously, reduces the expression of all three of these important oncoproteins (FIGS. 20, 7A, and 8). HeLa cells that make endogenous let-7 express increased levels of all three oncoproteins when transfected with an anti-let-7 inhibitor (FIGS. 20A, B and 7B). These results demonstrate that let-7 represses expression of these genes. Multiple mir-125 and mir-143 complementary sites have been identified in the human KRAS and BCL2 3'UTRs and it is expected these oncomirs may also regulate these oncogenes in a manner similar to that seen with let-7.

The results indicate that let-7 is a master regulator of cancer pathways, regulating proliferation (RAS and MYC) and survival pathways (BCL2). It is possible that let-7 also regulates telomerase (TERT) and angiogenesis (VEGF) pathways (Table 1). Since cancer is the result of multiple genetic mutations, these results indicate that introduction of let-7 to cancer patients could repress the expression of multiple oncogenes, and provide an effective therapy (effectively a one drug cocktail).

Example 5

Effects of Radiation on Cellular miRNA Expression Levels

Experimental Procedures

Total RNA was collected from cells before and 2, 8 and 24 hours post exposure to 2.5 Gray (Gy) of radiation. Total RNA was collected from cells using the mirVana kit from Ambion (per manufacturer's instructions). A total of 10 μg was used for microRNA microarray by LC Sciences. To confirm the quality of the RNA a UV test was performed and the samples were enriched for miRNAs by using a cut-off filter (um100 from microcon-modified procedure). The microRNAs were then labeled and hybridized to a microarray chip with multiple repeat regions and a miRNA probe region, which detects miRNA transcripts listed in Sanger miRBase release 8.2. This consists of 440 human miRNA sequences. Multiple control probes were included in each chip. The control probes were used for quality controls of chip production, sample labeling and assay conditions. For the in-depth data analysis of our time-point experiments, LC Sciences performed multi-array normalization, ANOVA (Analysis of Variance), and clustering analysis. The ANOVA and clustering analysis were performed on ratio data of individual arrays (with the multi-array normalization) instead of the often used intensity data of individual samples. They found this necessary in order to reveal the rather small miRNA variations among the samples of different time points. Since there was only one sample for each time point, they used repeating probe sets of the arrays to have constructed "groups" that were needed for ANOVA analysis.

Results

Figures 21A, 21B:
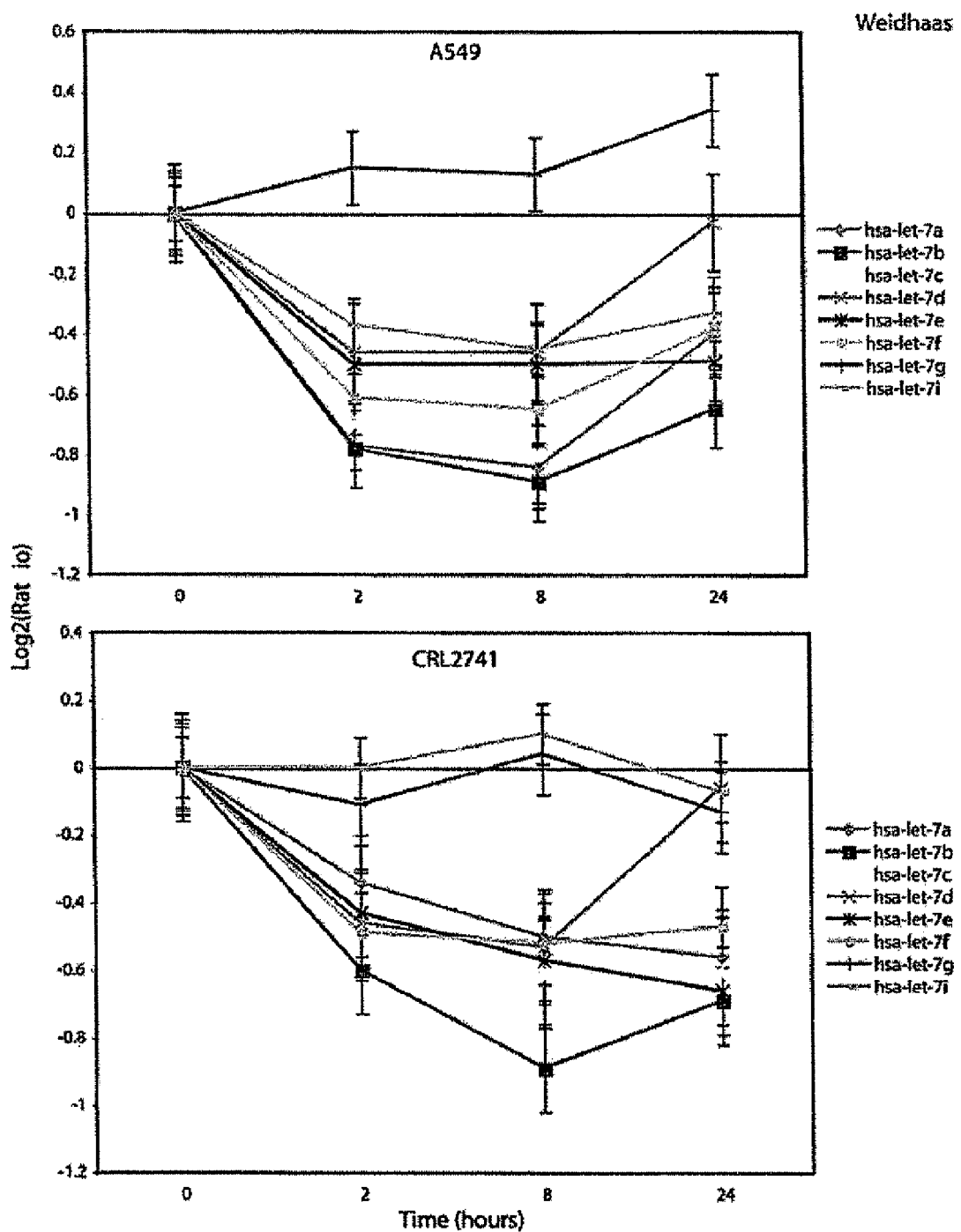
FIGS. 21A and 21B are line graphs showing the levels (Log 2 Ratio) of the indicated let-7 microRNAs (hsa-let-7a ♦; hsa-let-7b ■; hsa-let-7c ▲; hsa-let-7d ×; hsa-let-7e *; hsa-let-7f ●; hsa-let-7g +; hsa-let-7i □) collected from cells prior to, and at 2, 8 and 24 hours post irradiation (2.5 Gray). The ratio of let-7 levels is shown with the unirradiated 0 time point as a baseline and error bars represent standard deviation.

To determine whether miRNAs are involved in the cellular response to cytotoxic therapy, miRNA microarrays were utilized to compare the relative levels of cellular miRNAs before and after radiation. A lung cancer cell line, A549, in which let-7 levels are low (Johnson, et al., *Cell*, 120:635-47 (2005)) and RAS is activated (Valenzuela, and Groffen, *Nucleic Acids Res.*, 14:843-852 (1986)) was irradiated. The levels of eighty-one miRNAs significantly changed postirradiation. Significant changes in expression of most miRNAs was observed as early as two hours post-irradiation, with most of these early-affected miRNAs returning to their baseline expression levels by twenty-four hours. Interestingly, each member of the let-7 family of miRNAs, barring one (let-7g), decreased significantly by 2 hours post-irradiation (FIG. 21A). Of the 23 miRNAs with decreased expression post-irradiation, 7 (30%) were members of the let-7 family, a 17-fold enrichment over their representation on the array (1.8% [8/440 miRNAs on the array]). Real-time PCR was used to validate the microarray findings for several let-7 homologues.

Figure 21C:
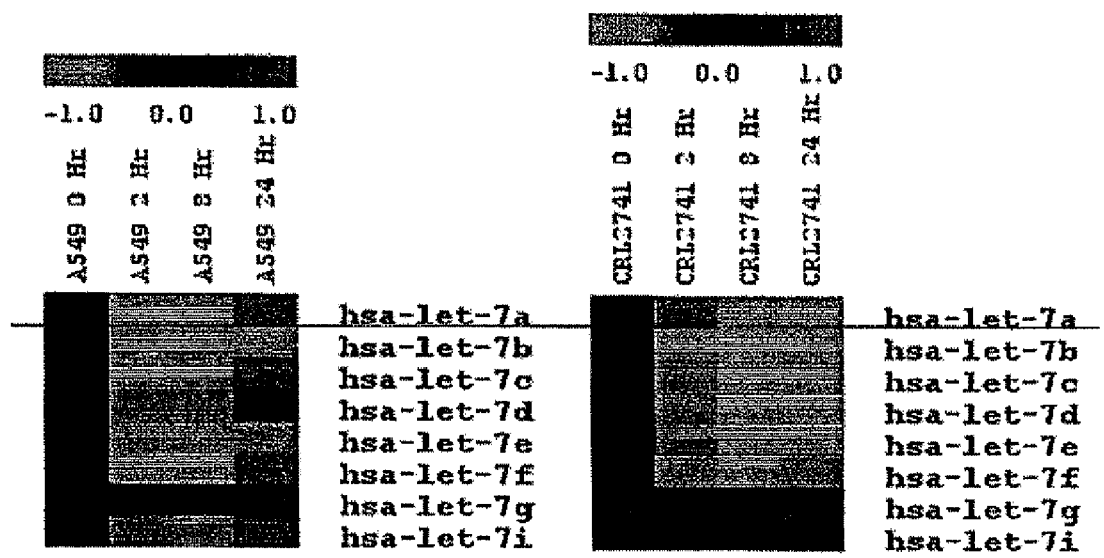
FIG. 21C shows heat maps demonstrating let-7 changes post-irradiation in A549 cells and CRL2741 cells with similar changes in let-7 ratios observed over the first twenty-four hours post-radiation.

The same microarray analysis was performed in a normal lung epithelial cell line, CLR2741. The levels of most miRNAs, including all members of the let-7 family, were significantly different between these two cell types before radiation. However, both the normal and tumor cells exhibited similar patterns of miRNA expression change in response to radiation. The similarity between the miRNA response postirradiation in the cancerous and normal epithelial cell lines suggests that a highly conserved global miRNA response exists in lung cells post-irradiation (FIGS. 21B and 21C), and further, that miRNAs are critical components of the cellular response to cytotoxic insult.

Example 6

Effects of let-7 miRNAs on the Radiation Response and Cell Survival

Experimental Procedures

A549 cells were transfected with 90 nM of the pre-let-7 or control pre-miR. Several transfection methods with different carriers were evaluated to compare toxicity versus efficiency, as measured by a luciferase reporter construct sensitive to let-7 levels (luc fused to the NRAS 3' UTR), and the method with the least toxicity and most efficient transfection (XtremeGENE, Roche, data not shown) was selected for transfections. Twenty-four hours after transfection, cells were treated with increasing doses of radiation (2.0, 4.0 or 6.0 Gy) and then plated at different dilutions and grown without being disturbed. Colonies were counted after two weeks.

Results

Figure 22A:
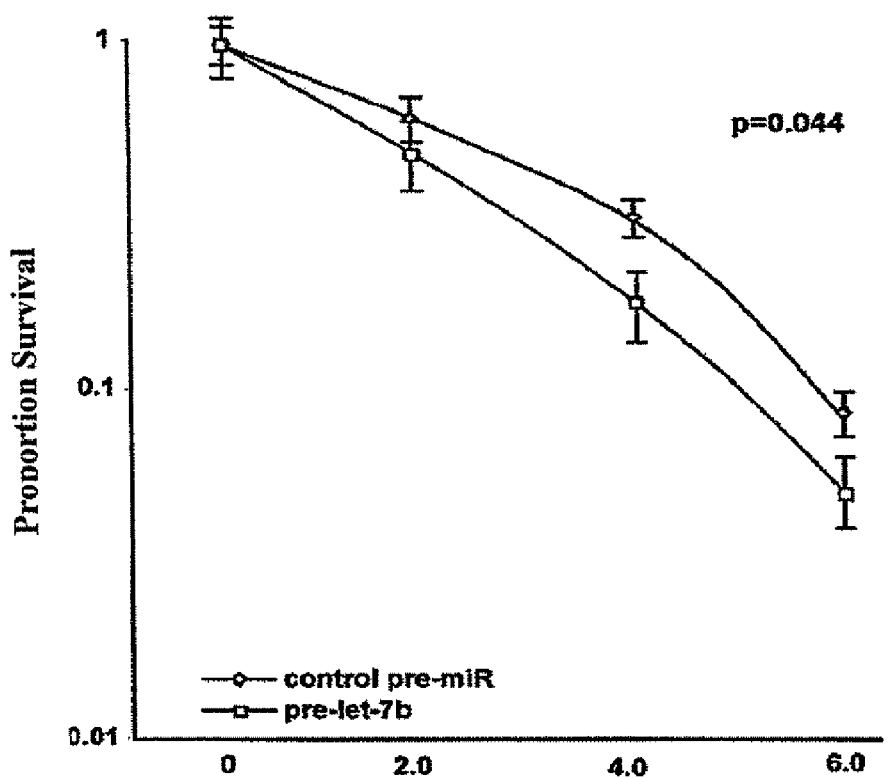
FIG. 22A is a line graph showing the survival (proportion survival) of A549 cells transfected with let-7b and irradiated 24 hours later with 2.0, 4.0 or 6.0 Grays (Gy). Survival was measured using a clonogenic assay. Error bars represent standard deviation.
Figure 22B:
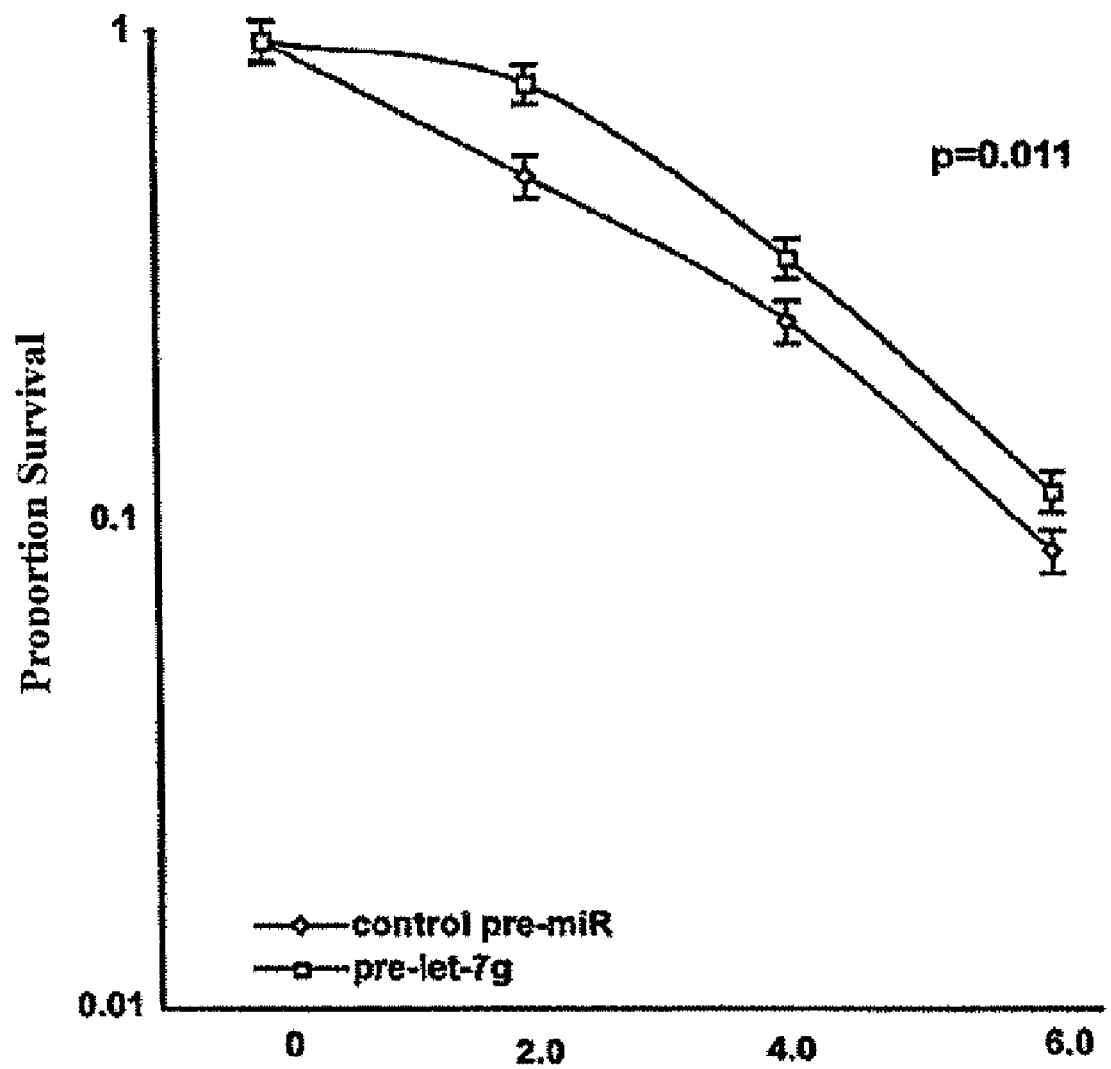
FIG. 22B is a line graph showing the survival proportion survival) of A549 cells transfected with let-7g and irradiated 24 hours later with 2.0, 4.0 or 6.0 Grays (Gy). Survival was measured using a clonogenic assay. Error bars represent standard deviation.
Figure 22C:
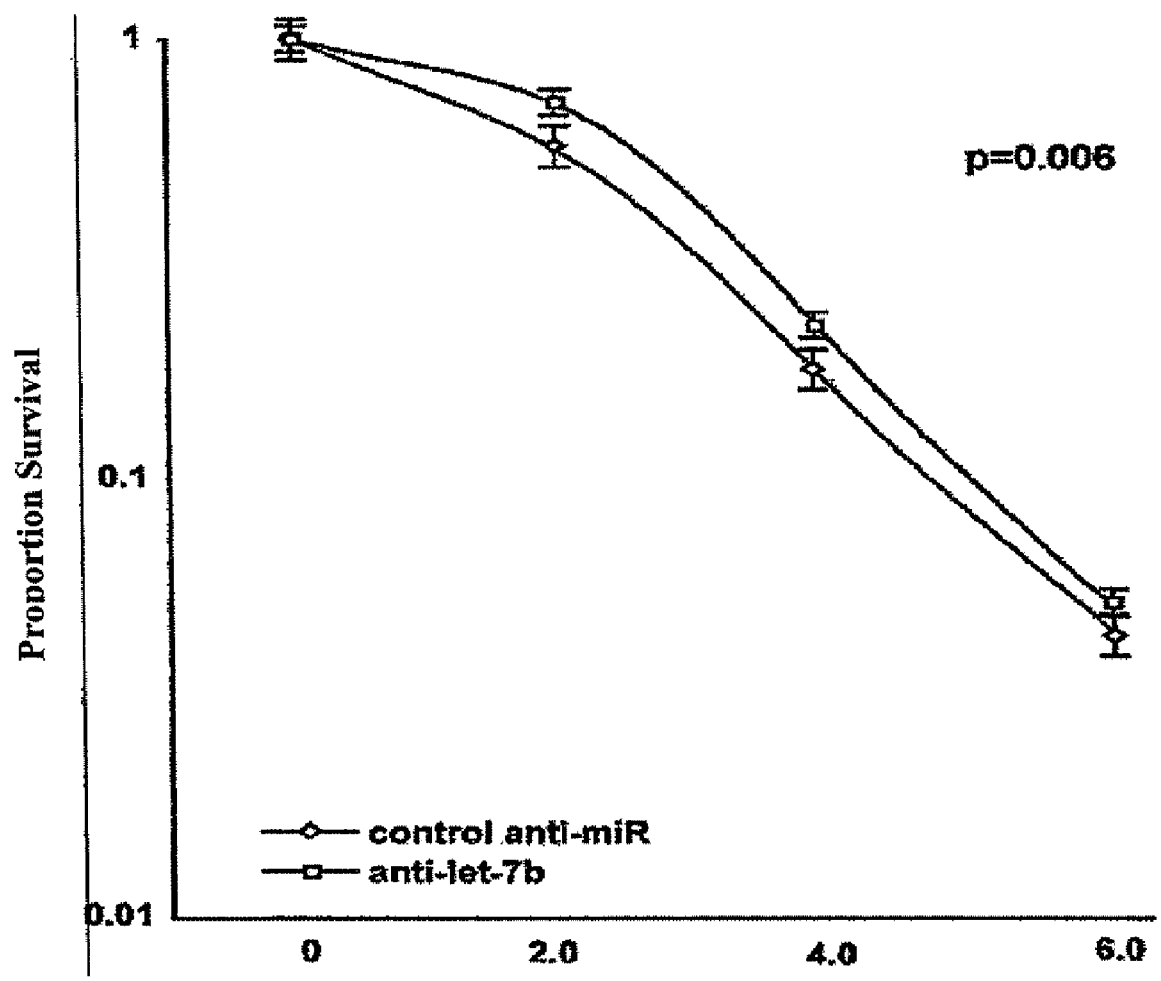
FIG. 22C is a line graph showing the survival (proportion survival) of A549 cells transfected with anti-let-7b and irradiated 24 hours later with 2.0, 4.0 or 6.0 Grays (Gy). Survival was measured using a clonogenic assay. Error bars represent standard deviation.
Figure 22D:
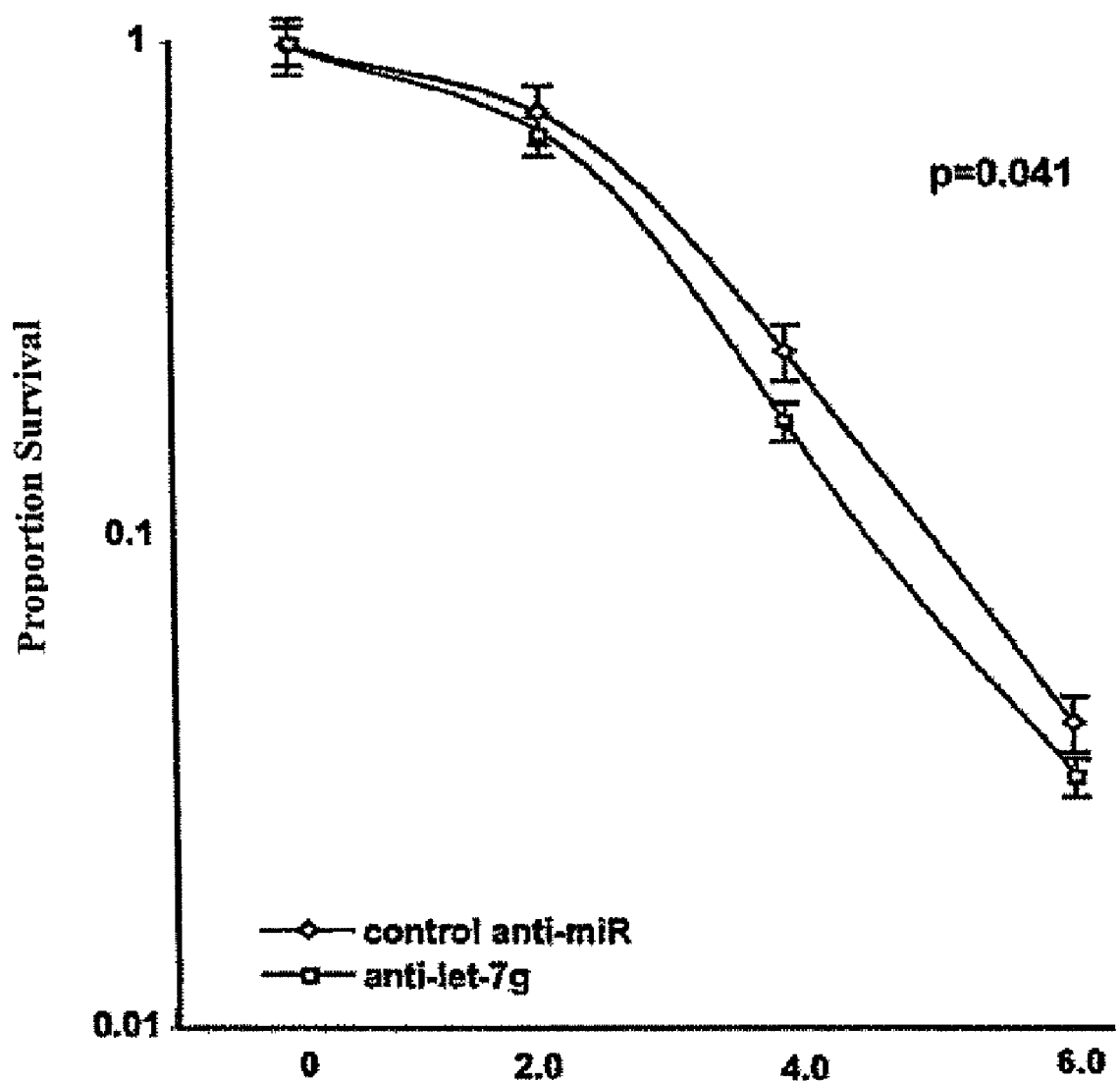
FIG. 22D is a line graph showing the survival (proportion survival) of A549 cells transfected with anti-let-7g and irradiated 24 hours later with 2.0, 4.0 or 6.0 Grays (Gy). Survival was measured using a clonogenic assay. Error bars represent standard deviation.

The results obtained in Example 5 above suggested that altering miRNA levels could be an efficacious approach to alter the cellular radiation response. Clonogenic cell survival assays measure all forms of cell death and are the recognized standard for radiation sensitivity assays (Rockwell, Lab Anim. Sci., 27:931-51 (1977)). Therefore this assay was employed to test the impact of altering let-7 levels on the radiation response and cell survival. let-7 over-expression in A549 cell lines causes defects in proliferation, but does not cause apoptosis in these cells. Specifically, the impact of let-7b, let-7a, and let-7g on the radiation response was evaluated because: let-7b drops the most significantly post-irradiation (FIGS. 1A-1C); let-7a levels have been implicated in predicting outcome in certain cancers, most notably lung cancer and; let-7g levels are upregulated post-irradiation and significantly changed only in the tumor cell line (FIGS. 1A-1C). To over-express each of the let-7 homologues of interest, A549 cells were transfected with synthetic pre-let-7 molecules or control pre-miRNA containing scrambled sequences (Ambion). Twenty-four hours after transfection, cells were treated with increasing doses of radiation and then plated at different dilutions and grown without perturbation. After two weeks, colonies were counted. Significant radiosensitization was found in cells treated with pre-let-7b as compared to control pre-miRNA (FIG. 22A). In parallel experiments, anti-miRs were delivered to A549 cells to specifically decrease let-7 miRNA activity. As expected from the effects of let-7b over-expression, anti-let-7b caused significant radioprotection (FIG. 22C). Consistent with the unique direction of altered expression levels of let-7g post-irradiation, a unique role for let-7g in the radiation response was identified. let-7g over-expression protected A549 cells from radiation (FIG. 2B), while anti-let-7g caused radiosensitization of A549 cells (FIG. 22D), opposite to the effects of let-7a and let-7b. While not wishing to be bound by theory, it is possible that over-expression of let-7a and let-7b causes radiosensitization and over-expression of let-7g radioprotection in part by overcoming the innate requirement of the cell to down- or up-regulate these miRNAs as part of the radiation response. However, the molecular mechanisms of miRNA function in the radiation response may also be related to alteration in the levels of their targets, such as RAS. These results indicate that the let-7 miRNA family is important in the radiation response and that their manipulation is a powerful method to alter mammalian cell survival post-irradiation.

Example 7

Effects of let-7 miRNAs on the Radiation Response and Cell Survival in C. elegans Experimental Procedures Methods for culturing, handling and genetic manipulation of C. elegans were as described by Brenner unless otherwise indicated (Brenner, Genetics, 77:71-94 (1974)). The animals referred to here as wild-type C. elegans correspond to the Bristol strain N2. Strains used in this study were obtained from the C. elegans Genetics Center (CGC) unless otherwise noted. let-7 over-expressing strains were generated as described (Reinhart, et al., Nature, 403: 901-6 (2000); Esquela-Kerscher, Dev. Dyn., 234:868-77 (2005)). For synchronization, gravid hermaphrodites were treated as previously described (Weidhaas, Proc. Natl. Acad. Sci. U.S.A., 103: 9946-51 (2006)). Isolated embryos were treated with radiation as previously described (Weidhaas, Proc. Natl. Acad. Sci. U.S.A., 103: 9946-51 (2006)). While the doses in these studies may appear high, when accounting for DNA size using the target theory they were comparable to human doses. Animals were anesthetized with 5 mM Levamisole HCl, placed onto 2% agarose pads and examined using 40× Nomarski optics. All data points were normalized to their 0 Gy data point to rule out any vulval defects independent of irradiation. Dose response curves were generated at the first S-phase radioresistance peak [determined as previously described (Weidhaas, Proc. Natl Acad. Sci. U.S.A, 103: 9946-51 (2006))] by dividing synchronized C. elegans populations into individual feeding plates and treating each dose point sequentially, with a start and an end same-dose control sample. For each dose, a minimum of 100 animals were treated and scored per experiment, and experiments were repeated 2-4 times. For RNAi after synchronization animals were placed on plates with the appropriate bacterial strain containing the plasmid that over-expresses dsRNA from the gene of interest and grown until appropriate time for radiation. After irradiation animals were placed on plates with the same bacterial strain and grown until phenotypic analysis. For statistical analysis each of the mutant strains were compared against the wild type using a stratified two-sample Wilcoxon rank sum test. Stratified t-tests were performed to analyze significance for all cases. The p-value was based on a two-tailed evaluation of the data.

Results

Figures 23A, 23B:
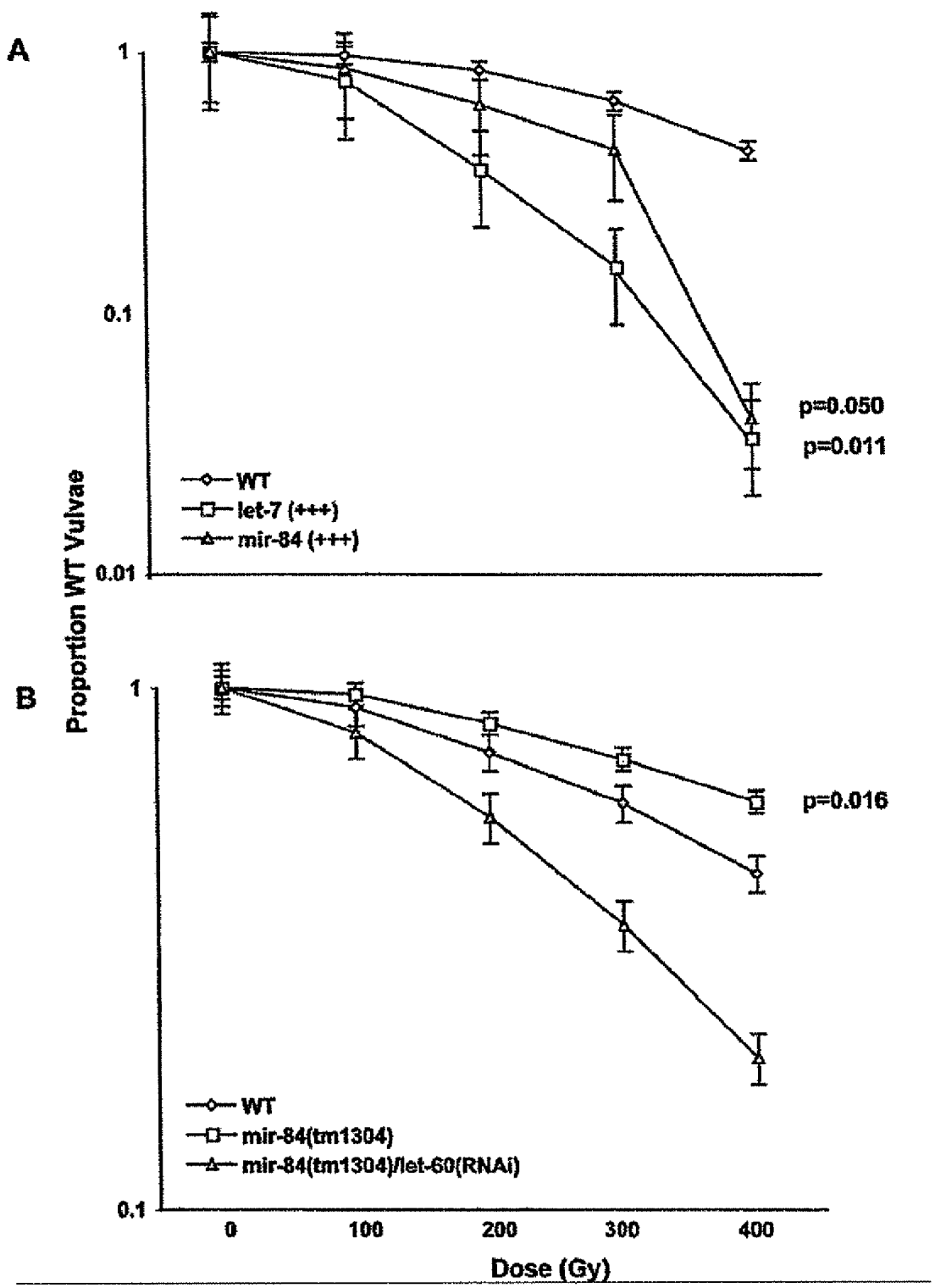
FIG. 23A is a line graph showing the effects of overexpression of let-7 and its homologue mir-84 on radiosensitization in the Radelegans *C. elegans* radiation model, Radiosensitization is measured as a percent of wild-type vulvae in wild-type (♦) let-7 overexpressing (■) or mir-84 overexpressing (▲) *C. elegans* treated with the indicated doses of radiation (Gy). P-values are listed next to the curves they represent compared to wild-type animals.
FIG. 23B is a line graph showing the effects of loss of mir-84 expression on radiosensitization in the Radelegans *C. elegans* radiation model. mir-84 deletion mutants mir-84 (tm1304) (■) were compared to wild type (♦) at the indicated doses of radiation (Gy). Radiosensitization is measured as a percent of wild-type vulvae in wild-type. The effect of RNAi against the *C. elegans* RAS homologue using let-60/RAS (RNAi) in a mir-84 deletion background (▲) is also shown. P value represents the mir-84 deletion strain compared to wild-type animals.

To confirm the ability of let-7 miRNAs to alter the radiation response in vivo, a powerful C. elegans-based in vivo model of radiation-induced reproductive cell death ("Radelegans") was employed (Weidhaas, Proc. Natl. Acad. Sci. U.S.A., 103: 9946-51 (2006)). The tissue model studied is the developing C. elegans vulva, in which multipotential vulval precursor cells (VPCs) undergo 3 rounds of cell division and differentiate into the mature vulva following RAS signaling (Han and Sternberg, Cell, 63:921-931 (1990)). VPCs represent tissue clonogens, considered the critical and determinant targets of radiation in tumors (Hewitt and Wilson, British Jour. Cancer, 14:186-94 (1960); Baker and Sanger, Int. J. Cell Cloning, 9:155-65 (1991)) and die via reproductive cell death post-irradiation (Weidhaas, Proc. Natl. Acad. Sci. U.S.A., 103: 9946-51 (2006)). Radiation resistance in VPCs depends on RAS signaling and a normal DNA damage response pathway (Weidhaas, et al., Cancer Res., 66:10434-8 (2006)). VPCs show specific expression of three let-7 paralogues, let-7, mir-48 and mir-84, that repress RAS expression in this tissue (Esquela-Kerscher, Dev. Dyn., 234:868-77 (2005)). Upon irradiation, VPCs in strains that over-express either let-7 or mir-84 were significantly radiosensitive compared to wild-type animals (FIG. 23A). This is consistent with results of the analysis of let-7a and let-7b in lung cancer cells (FIG. 22). Of note, no C. elegans toxicity was observed in these studies, suggesting that radiosensitivity mediated by let-7 over-expression is limited to the few actively dividing tissues, such as VPCs. let-7 mutants could not be analyzed for radiosensitivity due to gross defects in vulval development. Instead, animals harboring a mir-84 deletion were analyzed because they develop without obvious vulval abnormalities. In dose response experiments, mir-84(tm1304) animals exhibited significant radioresistance across all radiation doses (FIG. 23B) compared to a wild-type strain, consistent with the results of the in vitro analysis of let-7b (FIG. 22). mir-84 has been shown to regulate the let-60/RAS oncogene that is critical for protection from reproductive cell death in VPCs. Therefore, the hypothesis was tested that the radioresistance in the mir-84 mutant was partly due to let-60/RAS expression. Indeed, let-60/RAS(RNAi) suppressed the radioresistance in mir-84(tm1304) animals (FIG. 23B). Since the radioresistance of mir-84 mutants depended on a wild-type copy of let-60/RAS, this strongly suggests that RAS is a critical target of let-7 in the radioresponse. These studies in C. elegans confirm a conserved role for miRNAs in the cellular response to cytotoxic stress, such as radiation.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims. Those skilled in the art will recognize, or be able to ascertain using no more than routine experimentation, many equivalents to the specific embodiments of the invention described herein. Such equivalents are intended to be encompassed by the following claims.

We claim:

1. A method for increasing the sensitivity of a cell to radiotherapy comprising:

administering a composition comprising a let-7 miRNA and a suitable pharmaceutical carrier to a cell of a patient, that binds to and inhibits the expression of an mRNA encoded by an oncogene containing a let-7 complementary site (LCS) selected from the group consisting of NRAS, KRAS, HRAS, MYC, MYCL1, MYCN, BCL2, BCL2L1, BCL2L2, TERT, VEGF, EGF, EGFR, ERBB3, GRB2, RAF1, ARAF, MAP2K2, MAPK1, MAPK3, MET, KIT, TP73L(AIX), CCND1, CDK4, MDM2, FES, FURIN, INSL3, CSF1R, MYBL2, MYB, PIK3CD, PIK3C2B, PIK3CG, PIK3R5, AKT1, HLIN-41, VDR, PXR, FOXA1, FOXA2, ASH1L, ARID1B, GR, GLI2, 14-3-3zeta, MO25, SMGI, FRAP1, PER2 and AKT3 in a cell of a patient, and subsequently administering radiation to said patient, wherein said let-7 miRNA is administered in an effective amount to sensitize the cell to said radiotherapy and wherein said let-7 miRNA is selected from the group consisting of let-7a1, let-7a2, let-7a3, let-7b, let-7c, let-7d, let-7f, let-7h, let-7i, and mir-98.

2. The method of claim 1 wherein the miRNA is selected from the group consisting of a pri-miRNA, pre-miRNA, and mature let-7 miRNA.

3. The method of claim 2 wherein the let-7 miRNA is encoded by a nucleic acid.

4. The method of claim 3 wherein the nucleic acid is located on a vector.

5. The method of claim 4 wherein the vector is selected from the group consisting of a plasmid, cosmid, phagemid, virus, and other vehicles derived from viral or bacterial sources.

6. The method of claim 4 wherein the vector further comprises one or more in vivo expression elements.

7. The method of claim 6 wherein the in vivo expression element is selected from the group consisting of a promoter, enhancer, and combinations thereof.

8. The method of claim 1 wherein the miRNA is from 21 nucleotides to 170 nucleotides in length.

9. The method of claim 8 wherein the let-7 miRNA is from 21 to 25 nucleotides in length.

10. The method of claim 1 wherein the let-7 miRNA is administered to, or expression is increased in the cells of, a patient for treatment or prevention of cancer.

11. The method of claim 10 wherein the cancer is selected from the group consisting of lung cancer, pancreatic cancer, skin cancer, hematological neoplasms, breast cancer, brain cancer, colon cancer, follicular lymphoma, bladder cancer, cervical cancer, endometrial cancer, esophageal cancer, gastric cancer, head and neck cancer, multiple myeloma, liver cancer, lymphomas, oral cancer, osteosarcomas, ovarian cancer, prostate cancer, testicular cancer, and thyroid cancer.

* * * * *

SEQUENCE LISTING

<160> NUMBER OF SEQ ID NOS: 110

<210> SEQ ID NO 1
<211> LENGTH: 65
<212> TYPE: RNA
<213> ORGANISM: Ceanorhabditis elegans

<400> SEQUENCE: 1

-continued ugagguagua gguuguauag uuuggaauau uaccaccggu gaacuaugca auuuucuacc  60
uuacc  65

<210> SEQ ID NO 2
<211> LENGTH: 61
<212> TYPE: RNA
<213> ORGANISM: Drosophila melanogaster

<400> SEQUENCE: 2
ugagguagua gguuguauag uaguaauuac acaucauacu auacaaugug cuagcuuucu  60
u  61

<210> SEQ ID NO 3
<211> LENGTH: 70
<212> TYPE: RNA
<213> ORGANISM: Homo sapiens

<400> SEQUENCE: 3
ugagguagua gguuguauag uuuggggcuc ugcccugcua ugggauaacu auacaaucua  60
cugucuuucc  70

<210> SEQ ID NO 4
<211> LENGTH: 22
<212> TYPE: RNA
<213> ORGANISM: Ceanorhabditis elegans

<400> SEQUENCE: 4
uuauacaacc guucuacacu ca  22

<210> SEQ ID NO 5
<211> LENGTH: 20
<212> TYPE: RNA
<213> ORGANISM: Ceanorhabditis elegans

<400> SEQUENCE: 5
uuauacaacc auucugccuc  20

<210> SEQ ID NO 6
<211> LENGTH: 21
<212> TYPE: RNA
<213> ORGANISM: Ceanorhabditis elegans

<400> SEQUENCE: 6
ugagguagua gguuguauag u  21

<210> SEQ ID NO 7
<211> LENGTH: 22
<212> TYPE: DNA
<213> ORGANISM: Artificial
<220> FEATURE:
<223> OTHER INFORMATION: Nucleotides common to Let-7 sequences from
      various species

<400> SEQUENCE: 7
tgaggtagta ggttgtatag tt  22

<210> SEQ ID NO 8
<211> LENGTH: 19
<212> TYPE: DNA
<213> ORGANISM: Mus musculus

<400> SEQUENCE: 8

```
tgaggtagta gtttgtgct                                              19

<210> SEQ ID NO 9
<211> LENGTH: 22
<212> TYPE: DNA
<213> ORGANISM: Mus musculus

<400> SEQUENCE: 9
tgaggtagta gtgtgtacag tt                                          22

<210> SEQ ID NO 10
<211> LENGTH: 22
<212> TYPE: DNA
<213> ORGANISM: Mus musculus

<400> SEQUENCE: 10
tgaggtagta gtttgtacag ta                                          22

<210> SEQ ID NO 11
<211> LENGTH: 21
<212> TYPE: DNA
<213> ORGANISM: Mus musculus

<400> SEQUENCE: 11
agaggtagta gtttgcatag t                                           21

<210> SEQ ID NO 12
<211> LENGTH: 21
<212> TYPE: DNA
<213> ORGANISM: Mus musculus

<400> SEQUENCE: 12
agaggtagta ggttgcatag t                                           21

<210> SEQ ID NO 13
<211> LENGTH: 22
<212> TYPE: DNA
<213> ORGANISM: Homo sapiens

<400> SEQUENCE: 13
tgaggtagta gattgtatag tt                                          22

<210> SEQ ID NO 14
<211> LENGTH: 22
<212> TYPE: DNA
<213> ORGANISM: Homo sapiens

<400> SEQUENCE: 14
tgaggtagta ggttgtatag tt                                          22

<210> SEQ ID NO 15
<211> LENGTH: 21
<212> TYPE: DNA
<213> ORGANISM: Mus musculus

<400> SEQUENCE: 15
tgaggtagga ggttgtattg t                                           21

<210> SEQ ID NO 16
<211> LENGTH: 22
<212> TYPE: DNA
<213> ORGANISM: Homo sapiens
```

-continued

```
<400> SEQUENCE: 16
tgaggtagta gattgtatgg tt                                              22

<210> SEQ ID NO 17
<211> LENGTH: 22
<212> TYPE: DNA
<213> ORGANISM: Mus musculus

<400> SEQUENCE: 17
tgaggtagta ggttgtgtgg tt                                              22

<210> SEQ ID NO 18
<211> LENGTH: 22
<212> TYPE: DNA
<213> ORGANISM: Homo sapiens

<400> SEQUENCE: 18
tgaggtagta agttgtattg tt                                              22

<210> SEQ ID NO 19
<211> LENGTH: 22
<212> TYPE: DNA
<213> ORGANISM: Ceanorhabditis elegans

<400> SEQUENCE: 19
tgaggtagta tgtaatattg ta                                              22

<210> SEQ ID NO 20
<211> LENGTH: 21
<212> TYPE: DNA
<213> ORGANISM: Ceanorhabditis elegans

<400> SEQUENCE: 20
tgaggtaggt gcgagaaatg a                                               21

<210> SEQ ID NO 21
<211> LENGTH: 23
<212> TYPE: DNA
<213> ORGANISM: Ceanorhabditis elegans

<400> SEQUENCE: 21
tgaggtaggc tcagtagatg cga                                             23

<210> SEQ ID NO 22
<211> LENGTH: 21
<212> TYPE: DNA
<213> ORGANISM: Ceanorhabditis elegans

<400> SEQUENCE: 22
tccctgagac ctcaagtgtg a                                               21

<210> SEQ ID NO 23
<211> LENGTH: 22
<212> TYPE: DNA
<213> ORGANISM: Mus musculus

<400> SEQUENCE: 23
tccctgagac cctaacttgt ga                                              22

<210> SEQ ID NO 24
<211> LENGTH: 24
<212> TYPE: DNA
<213> ORGANISM: Ceanorhabditis elegans
```

<400> SEQUENCE: 24
tccctgagaa ttctcgaaca gctt                                          24

<210> SEQ ID NO 25
<211> LENGTH: 22
<212> TYPE: DNA
<213> ORGANISM: Mus musculus

<400> SEQUENCE: 25
tccctgagac ctttaacctg tg                                            22

<210> SEQ ID NO 26
<211> LENGTH: 26
<212> TYPE: RNA
<213> ORGANISM: Ceanorhabditis elegans

<400> SEQUENCE: 26
acuugugauc gauccucuuc cgccuc                                        26

<210> SEQ ID NO 27
<211> LENGTH: 25
<212> TYPE: RNA
<213> ORGANISM: Ceanorhabditis elegans

<400> SEQUENCE: 27
ugcaucgauu gaacuuguuc ucucg                                         25

<210> SEQ ID NO 28
<211> LENGTH: 20
<212> TYPE: RNA
<213> ORGANISM: Ceanorhabditis elegans

<400> SEQUENCE: 28
uccuucauuc uaauuccuca                                               20

<210> SEQ ID NO 29
<211> LENGTH: 24
<212> TYPE: RNA
<213> ORGANISM: Ceanorhabditis elegans

<400> SEQUENCE: 29
acaugcaucc gaaccccuc cucg                                           24

<210> SEQ ID NO 30
<211> LENGTH: 22
<212> TYPE: RNA
<213> ORGANISM: Ceanorhabditis elegans

<400> SEQUENCE: 30
auguuauaau guaugaugga gu                                            22

<210> SEQ ID NO 31
<211> LENGTH: 21
<212> TYPE: RNA
<213> ORGANISM: Ceanorhabditis elegans

<400> SEQUENCE: 31
uguuauaaug uaugauggag u                                             21

<210> SEQ ID NO 32
<211> LENGTH: 20
<212> TYPE: RNA

<213> ORGANISM: Ceanorhabditis elegans

<400> SEQUENCE: 32
ugcuuuauuc cccuuccucg                                              20

<210> SEQ ID NO 33
<211> LENGTH: 22
<212> TYPE: RNA
<213> ORGANISM: Ceanorhabditis elegans

<400> SEQUENCE: 33
uucauacaaa uuauuggccu ca                                           22

<210> SEQ ID NO 34
<211> LENGTH: 23
<212> TYPE: RNA
<213> ORGANISM: Ceanorhabditis elegans

<400> SEQUENCE: 34
aucugaaagu uuuugcuccc ucg                                          23

<210> SEQ ID NO 35
<211> LENGTH: 19
<212> TYPE: RNA
<213> ORGANISM: Ceanorhabditis elegans

<400> SEQUENCE: 35
ucauuuuucu cuauuccuc                                               19

<210> SEQ ID NO 36
<211> LENGTH: 25
<212> TYPE: RNA
<213> ORGANISM: Homo sapiens

<400> SEQUENCE: 36
aguucucaga auaacuaccu ccuca                                        25

<210> SEQ ID NO 37
<211> LENGTH: 26
<212> TYPE: RNA
<213> ORGANISM: Homo sapiens

<400> SEQUENCE: 37
ggcugucuga ccagagaaug caccuc                                       26

<210> SEQ ID NO 38
<211> LENGTH: 18
<212> TYPE: RNA
<213> ORGANISM: Homo sapiens

<400> SEQUENCE: 38
acagcacaaa cacaccuc                                                18

<210> SEQ ID NO 39
<211> LENGTH: 22
<212> TYPE: RNA
<213> ORGANISM: Homo sapiens

<400> SEQUENCE: 39
uugauauguu ggaugaugga gu                                           22

<210> SEQ ID NO 40
<211> LENGTH: 28

-continued

<212> TYPE: RNA
<213> ORGANISM: Homo sapiens

<400> SEQUENCE: 40
agcugugauc agugauuuuc aaaccuca                                      28

<210> SEQ ID NO 41
<211> LENGTH: 32
<212> TYPE: RNA
<213> ORGANISM: Homo sapiens

<400> SEQUENCE: 41
aauugccuuc aauccccuuc ucaccccacc uc                                 32

<210> SEQ ID NO 42
<211> LENGTH: 24
<212> TYPE: RNA
<213> ORGANISM: Homo sapiens

<400> SEQUENCE: 42
aucuaaauac uuacugaggu ccuc                                          24

<210> SEQ ID NO 43
<211> LENGTH: 25
<212> TYPE: RNA
<213> ORGANISM: Homo sapiens

<400> SEQUENCE: 43
aauuuuccug aggcuuauca ccuca                                         25

<210> SEQ ID NO 44
<211> LENGTH: 30
<212> TYPE: RNA
<213> ORGANISM: Homo sapiens

<400> SEQUENCE: 44
gauugcugaa agaauucua guuuaccuca                                     30

<210> SEQ ID NO 45
<211> LENGTH: 19
<212> TYPE: RNA
<213> ORGANISM: Homo sapiens

<400> SEQUENCE: 45
aacaggaacu auuggccuc                                                19

<210> SEQ ID NO 46
<211> LENGTH: 25
<212> TYPE: RNA
<213> ORGANISM: Homo sapiens

<400> SEQUENCE: 46
gacaguggaa guuuuuuuu ccucg                                          25

<210> SEQ ID NO 47
<211> LENGTH: 19
<212> TYPE: RNA
<213> ORGANISM: Homo sapiens

<400> SEQUENCE: 47
auuaguguca ucuugccuc                                                19

<210> SEQ ID NO 48

<211> LENGTH: 25
<212> TYPE: RNA
<213> ORGANISM: Homo sapiens

<400> SEQUENCE: 48
aaugcccuac aucuuauuuu ccuca                                           25

<210> SEQ ID NO 49
<211> LENGTH: 24
<212> TYPE: RNA
<213> ORGANISM: Homo sapiens

<400> SEQUENCE: 49
gguucaagcg auucucgugc cucg                                            24

<210> SEQ ID NO 50
<211> LENGTH: 24
<212> TYPE: RNA
<213> ORGANISM: Homo sapiens

<400> SEQUENCE: 50
ggcugguccg aacuccugac cuca                                            24

<210> SEQ ID NO 51
<211> LENGTH: 21
<212> TYPE: RNA
<213> ORGANISM: Homo sapiens

<400> SEQUENCE: 51
gauucaccca ccuuggccuc a                                               21

<210> SEQ ID NO 52
<211> LENGTH: 28
<212> TYPE: RNA
<213> ORGANISM: Homo sapiens

<400> SEQUENCE: 52
ggguguuaag acugacaca guaccucg                                         28

<210> SEQ ID NO 53
<211> LENGTH: 28
<212> TYPE: RNA
<213> ORGANISM: Homo sapiens

<400> SEQUENCE: 53
agugcuuaug aggggauauu uaggccuc                                        28

<210> SEQ ID NO 54
<211> LENGTH: 30
<212> TYPE: RNA
<213> ORGANISM: Homo sapiens

<400> SEQUENCE: 54
gaccgugggc cgaggugacu gcagacccuc                                      30

<210> SEQ ID NO 55
<211> LENGTH: 25
<212> TYPE: RNA
<213> ORGANISM: Homo sapiens

<400> SEQUENCE: 55
ggaaccccag cccuuagcuc cccuc                                           25

```
<210> SEQ ID NO 56
<211> LENGTH: 26
<212> TYPE: RNA
<213> ORGANISM: Homo sapiens

<400> SEQUENCE: 56
agcccuuagc uccccuccca ggccuc                                            26

<210> SEQ ID NO 57
<211> LENGTH: 23
<212> TYPE: DNA
<213> ORGANISM: Artificial
<220> FEATURE:
<223> OTHER INFORMATION: Common nucleotides in Let-7 family miRNAs in C.
      elegans

<400> SEQUENCE: 57
tgaggtaggt acgttatatg gta                                               23

<210> SEQ ID NO 58
<211> LENGTH: 22
<212> TYPE: DNA
<213> ORGANISM: Ceanorhabditis elegans

<400> SEQUENCE: 58
tgaggtagta ggttgtatag tt                                                22

<210> SEQ ID NO 59
<211> LENGTH: 21
<212> TYPE: DNA
<213> ORGANISM: Ceanorhabditis elegans

<400> SEQUENCE: 59
tgaggtaggt gcgagaaatg a                                                 21

<210> SEQ ID NO 60
<211> LENGTH: 26
<212> TYPE: RNA
<213> ORGANISM: Ceanorhabditis elegans

<400> SEQUENCE: 60
acuugggauc gauccucuuc cgccuc                                            26

<210> SEQ ID NO 61
<211> LENGTH: 25
<212> TYPE: RNA
<213> ORGANISM: Ceanorhabditis elegans

<400> SEQUENCE: 61
ugcaucgauu gaacuuguuc ucucg                                             25

<210> SEQ ID NO 62
<211> LENGTH: 20
<212> TYPE: RNA
<213> ORGANISM: Ceanorhabditis elegans

<400> SEQUENCE: 62
uccuucauuc uaauuccuca                                                   20

<210> SEQ ID NO 63
<211> LENGTH: 24
<212> TYPE: RNA
<213> ORGANISM: Ceanorhabditis elegans

<400> SEQUENCE: 63
```

```
acaugcaucc gaacccccuc cucg                                         24

<210> SEQ ID NO 64
<211> LENGTH: 20
<212> TYPE: RNA
<213> ORGANISM: Ceanorhabditis elegans

<400> SEQUENCE: 64
ugcuuuaucc cccuuccucg                                              20

<210> SEQ ID NO 65
<211> LENGTH: 22
<212> TYPE: RNA
<213> ORGANISM: Ceanorhabditis elegans

<400> SEQUENCE: 65
uucauacaaa uuauuggccu ca                                           22

<210> SEQ ID NO 66
<211> LENGTH: 23
<212> TYPE: RNA
<213> ORGANISM: Ceanorhabditis elegans

<400> SEQUENCE: 66
aucugaaagu uuuugcuccc ucg                                          23

<210> SEQ ID NO 67
<211> LENGTH: 19
<212> TYPE: RNA
<213> ORGANISM: Ceanorhabditis elegans

<400> SEQUENCE: 67
ucauuuuucu cuauuccuc                                               19

<210> SEQ ID NO 68
<211> LENGTH: 26
<212> TYPE: RNA
<213> ORGANISM: Ceanorhabditis elegans

<400> SEQUENCE: 68
ugcccaauuu cgccaacuca uuuuca                                       26

<210> SEQ ID NO 69
<211> LENGTH: 30
<212> TYPE: RNA
<213> ORGANISM: Ceanorhabditis elegans

<400> SEQUENCE: 69
uacauuuuca uuauucauuu aucuguuuua                                   30

<210> SEQ ID NO 70
<211> LENGTH: 21
<212> TYPE: RNA
<213> ORGANISM: Ceanorhabditis elegans

<400> SEQUENCE: 70
ucgucugcuc gucauuauuu u                                            21

<210> SEQ ID NO 71
<211> LENGTH: 22
<212> TYPE: RNA
<213> ORGANISM: Ceanorhabditis elegans
```

<400> SEQUENCE: 71
ucacuuucuc ugacuauuuu ca                                            22

<210> SEQ ID NO 72
<211> LENGTH: 21
<212> TYPE: RNA
<213> ORGANISM: Ceanorhabditis elegans

<400> SEQUENCE: 72
ucagaauguu uguauugcuu u                                             21

<210> SEQ ID NO 73
<211> LENGTH: 28
<212> TYPE: RNA
<213> ORGANISM: Ceanorhabditis elegans

<400> SEQUENCE: 73
uacaaauuau uggcucauc uauuuca                                        28

<210> SEQ ID NO 74
<211> LENGTH: 22
<212> TYPE: RNA
<213> ORGANISM: Ceanorhabditis elegans

<400> SEQUENCE: 74
ugccggucgu uccguuuauu uu                                            22

<210> SEQ ID NO 75
<211> LENGTH: 18
<212> TYPE: RNA
<213> ORGANISM: Ceanorhabditis elegans

<400> SEQUENCE: 75
ucguauugca uucauuuu                                                 18

<210> SEQ ID NO 76
<211> LENGTH: 21
<212> TYPE: RNA
<213> ORGANISM: Ceanorhabditis elegans

<400> SEQUENCE: 76
uauaauauuc cuauucuuuu g                                             21

<210> SEQ ID NO 77
<211> LENGTH: 19
<212> TYPE: RNA
<213> ORGANISM: Ceanorhabditis elegans

<400> SEQUENCE: 77
ugcaaugaua uaaauuuua                                                19

<210> SEQ ID NO 78
<211> LENGTH: 21
<212> TYPE: RNA
<213> ORGANISM: Ceanorhabditis elegans

<400> SEQUENCE: 78
acggugagac augccuccuc g                                             21

<210> SEQ ID NO 79
<211> LENGTH: 21
<212> TYPE: RNA
<213> ORGANISM: Ceanorhabditis elegans

<400> SEQUENCE: 79
uaaaugugau uugucaucuc g                                            21

<210> SEQ ID NO 80
<211> LENGTH: 24
<212> TYPE: RNA
<213> ORGANISM: Ceanorhabditis elegans

<400> SEQUENCE: 80
uaugggaguu gaugaagcau uuua                                         24

<210> SEQ ID NO 81
<211> LENGTH: 1372
<212> TYPE: DNA
<213> ORGANISM: C. elegans

<400> SEQUENCE: 81
atgacggagt acaagcttgt ggtagttgga gatggaggag ttggtaaatc agcactcacc    60
attcaactca tccagaatca ctttgtcgaa gaatacgacc cgaccataga ggacagctac   120
agaaagcagg ttgtgataga cggtgagaca tgcctcctcg acatattgga taccgccgga   180
caagaagaat attcggcgat gcgtgatcag tacatgagga caggcgaagg atttctgttg   240
gttttcgccg tcaacgaggc taaatctttc gagaatgtcg ctaactaccg cgagcagatt   300
cggagggtaa aggattcaga tgatgttcct atggtcttgg tagggaataa atgtgatttg   360
tcatctcgat cagtcgactt ccgaacagtc agtgagacac aaagggtta cggtattccg    420 aatgtcgaca catctgccaa aacgcgtatg ggagttgatg aagcatttta cacacttgtt   480
agagaaattc gcaagcatcg tgagcgtcac gacaataata agccacaaaa gaagaagaag   540
tgtcaaataa tgtgattcag cgtcgggaat tgcccaattt cgccaactca ttttcagtcg   600
tgtcaactcc cacccaatta tcctttctcg tactttttg gtacattttc attattcatt    660
tatctgtttt atctgaaact tgtgatcgat cctcttccgc tctacatac tcttcgaatt    720 tccacctttt tttctctatg catcgattga acttgttctc tcgtctgctc gtcattattt   780
tttctccttt tttttcttca tccttcattc taattcctca tctttcgctt agcccaaatc   840
tccattcatt cataggtgtc aaaactagct gtagtgtgtg atccatatct aaaacatgca   900
tccgaacccc ctcctcgttc caaaattggc caactctacc aaaaaaaaca tcgcaccatt   960 ttttttttcac tttctctgca tattttcaga atgtttgtat tgcttttttg atgctttatt  1020
ccccttcctc gttttcatac aaattattgg cctcatctat tttcagaagt tctctgaaaa  1080
ttaaattctt ttgcatctgc cggtcgttcc gtttatttt tctctgtttc ctctcatttt   1140
tgtcaagtaa ttatttctct ttcattaact ataatataga tacaattaga ccccatttct  1200
catacatttt ctgaacatct gaaagttttt gctccctcgt attgcattca ttttttctcta 1260 ttcctctaca ttttatagtc ctatctgaat ataatattcc tattcttttg atcaagtttt  1320
tattattatt ttattttcaa ggaagtattg caatgatata aattttaaaa ag          1372

<210> SEQ ID NO 82
<211> LENGTH: 1338
<212> TYPE: DNA
<213> ORGANISM: Ceanorhabditis briggssae

<400> SEQUENCE: 82
atgacggagt acaagcttgt ggtggttgga gatggaggag tgggaaagtc tgctctcact    60

| | |
|---|---|
| atccaactca ttcaaaacca cttcgtcgag gaatacgacc caactataga ggacagctat | 120 |
| cgaaagcagg tagtgatcga cggagagacc tgcctcctcg atatattgga tactgctggt | 180 |
| caagaggagt actcggcgat gcgcgatcag tatatgcgaa ctggagaggg attccttctg | 240 |
| gtcttcgccg tcaacgaggc caaatcgttc gaaaacgtag ccaactacag agagcaaatc | 300 |
| aggagggtga aggattcaga tgatgttcca atggttctgg ttggaaacaa gtgcgatttg | 360 |
| gcttctcggt cagtggactt ccgaacagtc agcgaaacag ccaagggata cggaatgcca | 420 |
| aatgtggata cttcagccaa aactcgcatg ggtgtcgatg aggcattcta cacactcgtt | 480 |
| cgagagatac gcaagcatcg cgagcgtcac gacaacaaca aaccacaaaa gaaaaagaag | 540 |
| tgtcaaatta tgtgattcag ccaaacccctt tcgccaacga tgtttcgttc atgtcaactc | 600 |
| gcccagctat cctttctcct gtgcttcggt acactctttt atctgtttta ctgaatttt | 660 |
| gtgattgatt ctctcccgac ctatatactc ccatacactt ttattttct atgcatcgat | 720 |
| tgaactcgtt cactcgtctg ccacttcaac ccgatattat aaattccgc acccatttt | 780 |
| cttccttcta attccgtctt tttcgcttat actatcgttc ataggtgtaa aaatagtagt | 840 |
| agtgtgattc atatctgaaa atacatctgg aacttttccg aaccaaatcc aaaatcacca | 900 |
| aaaaaaccac accatttttc actttctttg cttatttccc ctcatattat ttgtattgct | 960 |
| tccctgatgc tttattccct cttccgtgcc gttttggtt tctacccatt tatgctaatc | 1020 |
| tctgggaacc aaaatctgtt gcatctgccg gtggttcaat tcttttttt tctccgttac | 1080 |
| tattgttttt atcaaaccca ttctcttatt aacataacaa tagaatctct tagacccact | 1140 |
| ccacaagttt ttttctgaaa catctttcc ccattttttt cactttgaat gcttttcctt | 1200 |
| ccgatttata gctctatctg aatataatat ttcttaattc ttcttcacat tttttttgta | 1260 |
| tttttttgcac caatgatatg aaactgaatt tttgaatatt gatatggaaa cctaaaaata | 1320 |
| cgtcgttctc ccgtgttt | 1338 |

<210> SEQ ID NO 83
<211> LENGTH: 1012
<212> TYPE: DNA
<213> ORGANISM: Artificial
<220> FEATURE:
<223> OTHER INFORMATION: Consensus Sequence

<400> SEQUENCE: 83

| | |
|---|---|
| atgacggagt acaagcttgt ggtgttggag atggaggagt ggaatcgcct cacatcaact | 60 |
| catcaaacac ttgtcgagaa tacgacccac atagaggaca gctagaaagc aggtgtgatg | 120 |
| acgggagact gcctcctcga atattggata cgcggcaaga gatatcggcg atgcggatca | 180 |
| gtaatggacg ggaggattct tggtttcgcc gtcaacgagg caaatcttcg aaagtgcaac | 240 |
| tacggagcaa tggagggtaa ggattcagat gatgttccat ggttggtgga aaatggattt | 300 |
| gctctcgtca gtgacttccg aacagtcagg aacagcaagg gtacggatcc aatgtgaact | 360 |
| cgccaaaacc gatggggtga tgagcattta cacactgttg agaatcgcaa gcatcggagc | 420 |
| gtcacgacaa aaaccacaa aagaaaagaa gtgtcaatat gtgattcagc aactttcgcc | 480 |
| aactttctct gtcaactccc catatccttt ctcttttggt acatctttat ctgttttatc | 540 |
| tgaattgtga tgatctctcc tcctaatact ctcacttttt ttctatgcat cgattgaact | 600 |
| gttcctcgtc tgccgattat tttctttttc ttcttctaat tcctttcgct tatctcttca | 660 |
| ataggtgtaa aataggtagt gtgatcatat ctaaaatcat cgacttcgcc aaacaatcac | 720 |
| caaaaaaaca caccattttt cactttcttg ctattttcaa ttttgtattg ctttgatgct | 780 |

```
ttattccctc tctctttttgg tcctttgtct ctgaaaaatc tttgcatctg ccggtgttct    840
ttttttttct cgttcttttt tttcaaattc tcttattaac ataaatagac ttagacccat    900 ccatttctg aaaattttcc ctttcattc tttccttctt tatagctatc tgaatataat     960
attctattct tttcattttt tttattttt cacaatgata taattttaaa aa            1012
```

<210> SEQ ID NO 84
<211> LENGTH: 189
<212> TYPE: PRT
<213> ORGANISM: Homo sapiens

<400> SEQUENCE: 84

```
Met Thr Glu Tyr Lys Leu Val Val Val Gly Ala Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
                115                 120                 125

Gln Ala Gln Asp Leu Ala Arg Ser Tyr Gly Ile Pro Tyr Ile Glu Thr
                130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
                180                 185
```

<210> SEQ ID NO 85
<211> LENGTH: 189
<212> TYPE: PRT
<213> ORGANISM: Homo sapiens

<400> SEQUENCE: 85

```
Met Thr Glu Tyr Lys Leu Val Val Val Gly Ala Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Gln Glu Glu Tyr
                50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95
```

```
Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 86
<211> LENGTH: 188
<212> TYPE: PRT
<213> ORGANISM: Homo sapiens

<400> SEQUENCE: 86

```
Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 87
<211> LENGTH: 184
<212> TYPE: PRT
<213> ORGANISM: Ceanorhabditis elegans

<400> SEQUENCE: 87

```
Met Thr Glu Tyr Lys Leu Val Val Val Gly Asp Gly Val Gly Lys
1               5                   10                  15

Ser Ala Leu Thr Ile Gln Leu Ile Gln Asn His Phe Val Glu Glu Tyr
            20                  25                  30

Asp Pro Thr Ile Glu Asp Ser Tyr Arg Lys Gln Val Val Ile Asp Gly
        35                  40                  45
```

```
Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Leu
 65                  70                  75                  80

Val Phe Ala Val Asn Glu Ala Lys Ser Phe Glu Asn Val Ala Asn Tyr
                 85                  90                  95

Arg Glu Gln Ile Arg Arg Val Lys Asp Ser Asp Val Pro Met Val
                100                 105                 110

Leu Val Gly Asn Lys Cys Asp Leu Ser Ser Arg Ser Val Asp Phe Arg
                115                 120                 125

Thr Val Ser Glu Thr Ala Lys Gly Tyr Gly Ile Pro Asn Val Asp Thr
130                 135                 140

Ser Ala Lys Thr Arg Met Gly Val Asp Glu Ala Phe Tyr Thr Leu Val
145                 150                 155                 160

Arg Glu Ile Arg Lys His Arg Glu Arg His Asp Asn Asn Lys Pro Gln
                165                 170                 175

Lys Lys Lys Lys Cys Gln Ile Met
                180

<210> SEQ ID NO 88
<211> LENGTH: 188
<212> TYPE: PRT
<213> ORGANISM: Ceanorhabditis elegans

<400> SEQUENCE: 88

Met Arg Glu Tyr Lys Ile Val Val Leu Gly Ser Gly Gly Val Gly Lys
  1               5                  10                  15

Ser Ala Leu Thr Val Gln Phe Val Gln Gly Ile Phe Val Glu Lys Tyr
                 20                  25                  30

Asp Pro Thr Ile Glu Asp Ser Tyr Arg Lys Gln Val Glu Val Asp Gly
                 35                  40                  45

Gln Gln Cys Met Leu Glu Ile Leu Asp Thr Ala Gly Thr Glu Gln Phe
 50                  55                  60

Thr Ala Met Arg Asp Leu Tyr Met Lys Asn Gly Gln Gly Phe Val Leu
 65                  70                  75                  80

Val Tyr Ser Ile Thr Ala Gln Ser Thr Phe Asn Asp Leu Met Asp Leu
                 85                  90                  95

Arg Asp Gln Ile Leu Arg Val Lys Asp Thr Asp Glu Val Pro Met Ile
                100                 105                 110

Leu Val Gly Asn Lys Cys Asp Leu Glu Asp Glu Arg Val Val Gly Lys
                115                 120                 125

Asp Gln Gly Gln Asn Leu Ala Arg Gln Phe Gly Ser Ala Phe Leu Glu
130                 135                 140

Thr Ser Ala Lys Ala Lys Ile Asn Val Ser Glu Val Phe Tyr Asp Leu
145                 150                 155                 160

Val Arg Gln Ile Asn Arg Arg Tyr Pro Glu Ser Gly Arg Arg Gln Gly
                165                 170                 175

Gln Ser Asn Lys Gln Cys Cys Ser Cys Val Ile Met
                180                 185

<210> SEQ ID NO 89
<211> LENGTH: 181
<212> TYPE: PRT
<213> ORGANISM: Ceanorhabditis elegans

<400> SEQUENCE: 89
```

```
Met Arg Glu Phe Lys Val Val Leu Gly Ser Gly Val Gly Lys
1               5                   10                  15

Ser Ala Leu Thr Val Gln Phe Val Ser Ser Thr Phe Ile Glu Lys Tyr
                20                  25                  30

Asp Pro Thr Ile Glu Asp Phe Tyr Arg Lys Glu Ile Glu Val Asp Gly
            35                  40                  45

Gln Pro Ser Val Leu Glu Ile Leu Asp Thr Ala Gly Thr Glu Gln Phe
    50                  55                  60

Ser Ser Met Arg Asp Leu Tyr Ile Lys Asn Gly Gln Gly Phe Val Val
65                  70                  75                  80

Val Tyr Ser Ile Thr Ser Gln Gln Thr Phe His Asp Ile Arg Asn Met
                85                  90                  95

Lys Glu Gln Ile Val Arg Val Lys Gly Ser Glu Asn Val Pro Ile Leu
            100                 105                 110

Leu Val Gly Asn Lys Cys Asp Leu Ser His Gln Arg Gln Val Arg Ser
    115                 120                 125

Glu Glu Gly Leu Ala Leu Ala Glu Ser Trp Ser Cys Pro Phe Thr Glu
130                 135                 140

Cys Ser Ala Lys Asn Asn Gln Asn Val Asn Val Thr Phe Ala Glu Ile
145                 150                 155                 160

Val Arg Glu Met Asn Tyr Val Gln Asn Lys Ser Arg Gln Ser Lys Ser
                165                 170                 175

Cys Cys Ser Leu Met
                180

<210> SEQ ID NO 90
<211> LENGTH: 212
<212> TYPE: PRT
<213> ORGANISM: Ceanorhabditis elegans

<400> SEQUENCE: 90

Met Gly Gly Arg Ser Asn Ser Ala Thr Thr Ala Ala Gln Gln Asn Ala
1               5                   10                  15

Val Leu Arg Ile Val Val Gly Gly Gly Val Gly Lys Ser Ala
                20                  25                  30

Leu Thr Ile Gln Phe Ile Gln Arg Tyr Phe Val Gln Asp Tyr Asp Pro
            35                  40                  45

Thr Ile Glu Asp Ser Tyr Thr Lys Gln Cys Phe Val Asp Glu Asp Leu
    50                  55                  60

Cys Lys Leu Glu Ile Leu Asp Thr Ala Gly Gln Glu Glu Phe Ser Thr
65                  70                  75                  80

Met Arg Glu Gln Tyr Leu Arg Thr Gly Ser Gly Phe Leu Ile Val Phe
                85                  90                  95

Ala Val Thr Asp Arg Asn Ser Phe Glu Glu Val Lys Lys Leu His Glu
            100                 105                 110

Leu Ile Cys Arg Ile Lys Asp Arg Asp Phe Pro Ile Ile Leu Val
    115                 120                 125

Gly Asn Lys Ala Asp Leu Glu Asn Glu Arg His Val Ala Arg His Glu
130                 135                 140

Ala Glu Glu Leu Ala His Arg Leu Ser Ile Pro Tyr Ile Glu Cys Ser
145                 150                 155                 160

Ala Lys Ile Arg Lys Asn Val Asp Glu Ala Phe Phe Asp Ile Val Arg
                165                 170                 175

Leu Val Arg Lys Tyr Gln His Asp Glu Arg Met Pro Ile His Pro His
            180                 185                 190
```

```
Asp Asp Arg Lys Leu Glu Ser Pro Ile Lys Leu Lys Lys Lys Lys Asn
        195                 200                 205

Cys Arg Ile Gln
    210

<210> SEQ ID NO 91
<211> LENGTH: 211
<212> TYPE: PRT
<213> ORGANISM: Ceanorhabditis elegans

<400> SEQUENCE: 91

Met Ser Asn Gly Gly Lys Arg Pro Pro Glu Asp Ser Lys Leu Pro
1               5                   10                  15

Tyr Tyr Lys Leu Val Val Ile Gly Asp Gly Val Gly Lys Ser Ser
            20                  25                  30

Leu Thr Ile Gln Phe Phe Gln Lys Gln Phe Val Asp Tyr Tyr Asp Pro
            35                  40                  45

Thr Ile Glu Asp Gln Tyr Ile Gln His Cys Glu Ile Asp Gly Asn Trp
    50                  55                  60

Val Ile Met Asp Val Leu Asp Thr Ala Gly Gln Glu Glu Phe Ser Ala
65                  70                  75                  80

Met Arg Glu Gln Tyr Ile Arg Gly Gly Arg Gly Phe Leu Leu Val Phe
                85                  90                  95

Ser Val Thr Glu Arg Lys Ser Phe Glu Glu Ala His Lys Leu Tyr Asn
                100                 105                 110

Gln Val Leu Arg Val Lys Asp Arg Ser Glu Tyr Pro Val Leu Leu Val
            115                 120                 125

Ala Asn Lys Val Asp Leu Ile Asn Gln Arg Val Val Ser Glu Gln Glu
    130                 135                 140

Gly Arg Glu Leu Ala Ala Gln Leu Lys Leu Met Tyr Ile Glu Thr Ser
145                 150                 155                 160

Ala Lys Glu Pro Pro Val Asn Val Asp Ala Ala Phe His Glu Leu Val
                165                 170                 175

Arg Ile Val Arg Ser Phe Pro Ser Asp Glu Gly Asp His Glu Ala Ser
            180                 185                 190

Met Ala Ser Val Pro Arg Thr Lys Lys Arg Lys Asp Lys Gly Lys Cys
        195                 200                 205

Leu Ile Ser
    210

<210> SEQ ID NO 92
<211> LENGTH: 1169
<212> TYPE: DNA
<213> ORGANISM: Homo sapiens

<400> SEQUENCE: 92
caagatactt ttaaagtttt gtcagaaaag agccactttc aagctgcact gacaccctgg     60
tcctgacttc cctggaggag aagtattcct gttgctgtct tcagtctcac agagaagctc    120
ctgctacttc cccagctctc agtagtttag tacaataatc tctatttgag aagttctcag    180
aataactacc tcctcacttg gctgtctgac cagagaatgc acctcttgtt actccctgtt    240
atttttctgc cctgggttct ccacagcaca aacacacctc tgccacccca ggttttcat     300 ctgaaaagca tttcatgtct gaaacagaga accaaaccgc aaacgtgaaa ttctattgaa    360
aacagtgtct tgagctctaa agtagcaact gctggtgatt ttttttttct ttttactgtt    420
```

| | |
|---|---:|
| gaacttagaa ctatgctaat tttggagaaa tgtcataaat tactgttttg ccaagaatat | 480 |
| agttattatt gctgtttggt ttgtttataa tgttatcggc tctattctct aaactggcat | 540 |
| ctgctctaga ttcataaata caaaaatgaa tactgaattt tgagtctatc ctagtcttca | 600 |
| caactttgac gtaattaaat ccaactttca cagtgaagtg cctttttcct agaagtggtt | 660 |
| tgtagacttc ctttataata tttcagtgga atagatgtct caaaaatcct tatgcatgaa | 720 |
| atgaatgtct gagatacgtc tgtgacttat ctaccattga aggaaagcta tatctatttg | 780 |
| agagcagatg ccattttgta catgtatgaa attggttttc cagaggcctg ttttggggct | 840 |
| ttcccaggag aaagatgaaa ctgaaagcac atgaataatt tcacttaata attttttacct | 900 |
| aatctccact tttttcatag gttactacct atacaatgta tgtaatttgt ttcccctagc | 960 |
| ttactgataa acctaatatt caatgaactt ccatttgtat tcaaatttgt gtcataccag | 1020 |
| aaagctctac atttgcagat gttcaaatat tgtaaaactt tggtgcattg ttatttaata | 1080 |
| gctgtgatca gtgattttca aacctcaaat atagtatatt aacaaattac attttcactc | 1140 |
| aaaaaaaaaa aaaaaaaaa aaaaaaaa | 1169 |

```
<210> SEQ ID NO 93
<211> LENGTH: 2302
<212> TYPE: DNA
<213> ORGANISM: Homo sapiens

<400> SEQUENCE: 93
```

| | |
|---|---:|
| caaagatact tttaaagttt tgtcagaaaa gagccacttt caagctgcac tgacaccctg | 60 |
| gtcctgactt ccctggagga gaagtattcc tgttgctgtc ttcagtctca cagagaagct | 120 |
| cctgctactt ccccagctct cagtagttta gtacaataat ctctatttga gaagttctca | 180 |
| gaataactac ctcctcactt ggctgtctga ccagagaatg cacctcttgt tactccctgt | 240 |
| tatttttctg ccctgggttc ttccacagca caaacacacc tctgccaccc caggttttc | 300 |
| atctgaaaag cagttcatgt ctgaaacaga gaaccaaacc gcaaacgtga aattctattg | 360 |
| aaaacagtgt cttgagctct aaagtagcaa ctgctggtga ttttttttt ctttttactg | 420 |
| ttgaacttag aactatgcta attttttggag aaatgtcata aattactgtt ttgccaagaa | 480 |
| tatagttatt attgctgttt ggtttgttta atgttatc ggctctattc tctaaactgg | 540 |
| catctgctct agattcataa atacaaaaat gaatactgaa ttttgagtct atcctagtct | 600 |
| tcacaacttt gacgtaatta aatccaactt tcacagtgaa gtgccttttt cctagaagtg | 660 |
| gtttgtagac ttcctttata atatttcagt ggaatagatg tctcaaaaat ccttatgcat | 720 |
| gaaatgaatg tctgagatac gtctgtgact tatctaccat tgaaggaaag ctatatctat | 780 |
| ttgagagcag atgccatttt gtacatgtat gaaattggtt ttccagaggc ctgttttggg | 840 |
| gctttcccag gagaaagatg aaactgaaag cacatgaata atttcactta ataattttta | 900 |
| cctaatctcc acttttttca taggttacta cctatacaat gtatgtaatt tgttttcccc | 960 |
| tagcttactg ataaacctaa tattcaatga acttccattt gtattcaaat ttgtgtcata | 1020 |
| ccagaaaagct ctacatttgc agatgttcaa atattgtaaa actttggtgc attgttattt | 1080 |
| aatagctgtg atcagtgatt ttcaaacctc aaatatagta tattaacaaa ttacattttc | 1140 |
| actgtatatc atggtatctt aatgatgtat ataattgcct tcaatcccct ctcacccca | 1200 |
| ccctctacag cttcccccac agcaataggg gcttgattat ttcagttgag taaagcatgg | 1260 |
| tgctaatgga ccagggtcac agtttcaaaa cttgaacaat ccagttagca tcacagaaa | 1320 |
| agaaattctt ctgcatttgc tcattgcacc agtaactcca gctagtaatt ttgctaggta | 1380 |

```
gctgcagtta gccctgcaag gaaagaagag gtcagttagc acaaacccctt taccatgact    1440 ggaaaactca gtatcacgta tttaaacatt tttttttctt ttagccatgt agaaaactcta    1500 aattaagcca atattctcat ttgagaatga ggatgtctca gctgagaaac gttttaaatt    1560
ctctttattc ataatgttct ttgaagggtt taaaacaaga tgttgataaa tctaagctga    1620
tgagtttgct caaaacagga agttgaaatt gttgagacag gaatgaaaaa tataattaat    1680
tgatacctat gaggatttgg aggcttggca ttttaatttg cagataatac cctggtaatt    1740
ctcatgaaaa atagacttgg ataacttttg ataaaagact aattccaaaa tggccacttt    1800
gttcctgtct ttaatatcta aatacttact gaggtcctcc atcttctata ttatgaattt    1860
tcatttatta agcaaaatgt catattaccct tgaaattcag aagagaagaa acatatactg    1920
tgtccagagt ataatgaacc tgcagagttg tgcttcttac tgctaattct gggagctttc    1980
acactacgtc atcatttgta aatggaaatt ctgcttttct gtttctgctc cttctggagc    2040
agtgctactc tgtaattttc ctgaggttat cacctcagtc atttcttttt taaatgtctg    2100
tgactggcag tgattctttt tcttaaaaat ctattaaatt tgatgtcaaa ttagggagaa    2160
agatagttac tcatcttggg ctcttgtgcc aatagcccctt gtatgtatgt acttagagtt    2220
ttccaagtat gttctaagca cagaagtttc taaatggggc caaaattcag acttgagtat    2280
gttctttgaa taccttaaga ag                                              2302

<210> SEQ ID NO 94
<211> LENGTH: 2297
<212> TYPE: DNA
<213> ORGANISM: Rodent

<400> SEQUENCE: 94 taagacccctt taaaagttct gtcatcagaa acgagccact ttcaagcctc actgatgccc     60
tggttctgac atccctggag gagacgtgtt tctgctgctc tctgcatctc agagaagctc    120
ctgcttcctg cttccccaac ttagttactg agcacagcca tctaacctga gacctcttca    180
gaataactac ctcctcactc ggctgtccga accagagaaa tgaacctgtt tctcccccagt    240 agttctctgc cctgggtttc ccctagaaac aaacacacct gccagctggc tttgtcctcc    300
gaaaagcagt ttacattgat gcacgagaac caaactatag acaagcaatt ctgttgtcaa    360
cagtttctta agctctaagg taacaattgc tggtgatttc ccccctttgcc cccaactgtt    420 gaacttggcc ttgttagttt tgggggaaat gtaaaaatta atcctcttcc ccgagaatag    480
aattagtgtt gctgattgcc tgatttgcaa tgtgatcagc tatattctat aagctggcgt    540
ctgctctgta ttcataaatg caaacatgag tactgacgta agtgcatccc tagtcttctc    600
agctgcatgc aattaaatcc aacgttcaca acaaagtgcc ttgtcctaac agtgctctgt    660
aggcttccgt tatagttcgt attgaaatag atgtttcaag aaccattgta taggaaagtg    720
actatgagcc atctaccttg gagggaaagg tgaatctacc tgatggcaga tgcttgtata    780
tgtacacata tgtacacaaa gacagttttcc ctgtttgcgg ttctcccagg agaaagaggg    840
aactgaaacg attatgacta atttcattta attctagcta atctttttt tttttttggg    900 agggggggag taggttacca cctataaata tttgtaattt cttctagctt actgataatc    960
taatagtcaa tgagcttcca ttataataaa ttggttcata ccaggaagcc ctccatttat   1020
agttagtcag atactgtaaa aattggcatg ttattacttt tacctgtga ttaatgattc   1080 ttcaaacccctt aaatatagtt attgcaggca ggttatatct ttgctgcata gtttcttcat   1140
```

```
ggaaaaaaaa aaatatatat atatatggag agagtggccc tcagttccca tctcaccatc      1200
cctctctttc agcctagatc agttcaagca tcctatagga gcttgaataa ttatctcagt      1260
tgaacaaacc atggtgctaa tggaccaggt catggtttca aaacttgaac aagccagtta      1320
gatcacagag aaaacagttc atccatattt gcctccctgc ctattactcc tgcttgtaga      1380
cttttgcctg atgcctgctg ttcgagctat aaggataaaa gttagtgtgg ttctacacca      1440
ggactgggaa tgcctggtga gctgttgggt aagcctagac acctttacat tttcagaccc      1500
gtatttttag ccccatggaa actgaagcca gagttcacac ctccatctct tcccccatta      1560
gataaatgtt cttaatctat atagcttttt aaaagtattt aaaacatgtc tataagttag      1620
gctaccaact aacaaaagct gatgtgtttg ttcaaataaa gaggtatcct ttactacttg      1680
agaaaagaat gtaaaatgcc attaattgtt gtcatgtaga agtttgatat ttgtggtaat      1740
gccctgataa ttcattggtg agtttgttag tcatggtgat acttaaaata taactcatct      1800
cagtaatttc aatgaaaaca taaaatggga tgccttgatt gaaaaagca aacctaattc       1860 caaaatgacc attttctctt ctgatcttac acacctaaa aatctgagat ccttgggatt       1920
catttgttta acaggaac ttgctatgta atcttggctg gcctcaaact cacaatgctc        1980
ttcctgcatc agtctcaaaa tgatgggatt acaggcacat gccaccacac acctgatc       2040 tggtttctaa tgaatttta ttgttaagca aatccccatc accttgaaac taatcagaag        2100
agggaagaaa catatgttgt gctcctcagt gctaatgctg ggatctttca ccaggggttt      2160
gcattcttaa gtaaactgct gccttttttac aacataggct cagtcatcct cctgaagctg     2220
cttgagacca acacttggtc ttgttctttt ttaatgtgtg ttatgactgg tggtggatct      2280
ctaaaaagtt tattaaa                                                     2297

<210> SEQ ID NO 95
<211> LENGTH: 2225
<212> TYPE: DNA
<213> ORGANISM: Rodent

<400> SEQUENCE: 95
aagttctgtc atcagaaaag agccactttg aagctgcact gatgccctgg ttctgacatc        60
cctggaggag acctgttcct gctgctctct gcatctcaga gaagctcctg cttcctgctt       120
ccccgactca gttactgagc acagccatct aacctgagac ctcttcagaa taactacctc       180
ctcactcggc tgtctgacca gagaaatgga cctgtctctc ccggtcgttc tctgccctgg       240
gttcccctag aaacagacac agcctccagc tggctttgtc ctctgaaaag cagtttacat       300
tgatgcagag aaccaaacta gacatgccat tctgttgaca acagtttctt atactctaag       360
gtaacaactg ctggtgattt tccccctgccc ccaactgttg aacttggcct tgttggtttg     420
gggggaaaat gtcataaatt actttcttcc caaatataa ttagtgttgc tgattgattt       480
gtaatgtgat cagctatatt ccataaactg gcatctgctc tgtattcata aatgcaaaca      540
cgaatactct caactgcatg caattaaatc caacattcac aacaaagtgc cttttcccta      600
aaagtgctct gtaggctcca ttacagtttg taattggaat agatgtgtca agaaccattg      660
tataggaaag tgactctgag ccatctacct ttgagggaaa ggtgtatgta cctgatggca      720
gatgctttgt gtatgcacat gaagatagtt tccctgtctg ggattctccc aggagaaaga     780
tggaactgaa acaattacaa gtaatttcat ttaattctag ctaatctttt ttttttttt       840 tttttggta gactatcacc tataaatatt tggaatatct tctagcttac tgataatcta       900
ataattaatg agcttccatt ataatgaatt ggttcatacc aggaagccct ccatttatag      960
```

```
tatagatact gtaaaaattg gcatgttgtt actttatagc tgtgattaat gattcctcag    1020
accttgctga gatatagtta ttagcagaca ggttatatct ttgctgcata gtttcttcat    1080
ggaatatata tctatctgta tgtggagaga acgtggccct cagttccctt ctcagcatcc    1140
ctcatctctc agcctagaga agttcgagca tcctagaggg gcttgaacag ttatctcggt    1200
taaaccatgg tgctaatgga ccgggtcatg gtttcaaaac ttgaacaagc cagttagcat    1260
cacagagaaa cagtccatcc atatttgctc cctgcctatt attcctgctt acagactttt    1320
gcctgatgcc tgctgttagt gctacaagga taagcttgtg tggttctcac caggactgga    1380
agtacctggt gagctctggg gtaagcctag atatctttac attttcagac ccttattctt    1440
agccacgtgg aaactgaagc cagagtccat acctccatct ccttcccccc ccaaaaaaat    1500
tagattaatg ttctttatat agcttttta aagtatttaa acatgtcta taagttaggc     1560 tgccaactaa caaagctga tgtgtttgtt caaataaaga ggtatccttc gctactcgag     1620
agaagaatgt aaaatgccat tgattgttgt cacttggagg cttgatgttt gccctgataa    1680
ttcattagtg ggttttgttt gtcacatgat acctaagatg taactcagct cagtaattct    1740
aatgaaaaca taaattggat accttaattg aaaaaagcaa acctaattcc aaaatggcca    1800
ttttctcttc tgatcttgta atacctaaaa ttctgaggtc cttgggattc ttttgtttat    1860
aacaggatct tgctgtgtag tcctagctgg cctcaaactc acaatactct tcctggatca    1920
atctcccaag tgctgggatt acaggcacat tccaccacac acacctgact gagctcgttc    1980
ctaatgagtt ttcattaagc aaattcccca tcaccttgaa actaatcaga aggggaaca    2040 aacatttgct atgctcctga gtgctaacac tgggctcatt cacatggggt ttgcattcct    2100
aggcaaacta aactgctgcc ttttacaaca aggctcagtc atcttcctga agctgctgag    2160
accagcactt ggtcttgttt tgttttaata tgtcttatga ctggtggtgg atccgtcgac    2220
ctgca                                                                2225

<210> SEQ ID NO 96
<211> LENGTH: 464
<212> TYPE: DNA
<213> ORGANISM: Rodent

<400> SEQUENCE: 96
caagatattt aacaaagttc tatcagaaaa gagccacttt caagctgcac tgatacccctg   60 gtcctgactt ccctggagga gaagtatccc tgttgctctc ttcatctcag agaagctcct   120
gctgtttgtc cacctctcag tgtatgagca cagtctctgc ttgagaactt ctcagaataa   180
ctacctcctc acttggttgt ctgaccagag aaatgcacct cttgttaatt ccccaataat   240
tttctgccct gggctctccc caacaaaaaa caaacacttc tgccatccaa aaagcaactt   300
ggtctgaaac agaaccaaac tgtagattga aattctctta aaaagtcttg agctctaaag   360
ttagcaaccg ctggtgattt ttattttcct ttttattttt gaacttggaa ctgacctatg   420
ttagattttg gagaaatgtc ataaagtact gttgtgccaa gaag                    464

<210> SEQ ID NO 97
<211> LENGTH: 25
<212> TYPE: RNA
<213> ORGANISM: Xenopus Laevis

<400> SEQUENCE: 97
aacacuuuuc aauaccacuu accuc                                          25
```

-continued

```
<210> SEQ ID NO 98
<211> LENGTH: 21
<212> TYPE: RNA
<213> ORGANISM: Xenopus Laevis

<400> SEQUENCE: 98
aauucuugcu guuaugccuc a                                              21

<210> SEQ ID NO 99
<211> LENGTH: 20
<212> TYPE: RNA
<213> ORGANISM: Xenopus Laevis

<400> SEQUENCE: 99
aacaaauugu ugagcaccuc                                                20

<210> SEQ ID NO 100
<211> LENGTH: 23
<212> TYPE: RNA
<213> ORGANISM: Ceanorhabditis elegans

<400> SEQUENCE: 100
uugauauguu ggauggaugg agu                                            23

<210> SEQ ID NO 101
<211> LENGTH: 21
<212> TYPE: RNA
<213> ORGANISM: Danio rerio

<400> SEQUENCE: 101
aauuuaucac auuuacccuc a                                              21

<210> SEQ ID NO 102
<211> LENGTH: 21
<212> TYPE: RNA
<213> ORGANISM: Danio Rerio

<400> SEQUENCE: 102
aaugaauaua uuauuuccuc a                                              21

<210> SEQ ID NO 103
<211> LENGTH: 21
<212> TYPE: RNA
<213> ORGANISM: Ceanorhabditis elegans

<400> SEQUENCE: 103
uugauauguu gaugauggag u                                              21

<210> SEQ ID NO 104
<211> LENGTH: 407
<212> TYPE: DNA
<213> ORGANISM: Rodent

<400> SEQUENCE: 104
tcaaatgcat ggtcaagtgc aacctcacaa ccttggctgg gtcttaggat tgaaaggttt    60
agccataatg taaactgcct caaatggaat tttgggcata aagaagcttt gccatctttt   120
tgtttgtttg ttttcccttta acagatttgt atttaagaat tgttttttaaa aaatgtgtca   180 agtttacccc gttttcctgt gtaaatatgg ccataacttt aataaaacgt ttatagcagt   240
tatacaagaa ttcaaccat gtattataaa ccataatttt ttttatttaa gtacattttc   300 tgatttttc tattgttttt agaaaaaata aaatacgtgg caaatatata attgagccaa   360
```
atcttaagtt gtgagtgttt tgttttctt gccttttttt tctattt        407

<210> SEQ ID NO 105
<211> LENGTH: 378
<212> TYPE: DNA
<213> ORGANISM: Homo sapiens

<400> SEQUENCE: 105
tcaaatgcat gatcaaatgc aacctcacaa ccttggctga gtcttgagac tgaaagattt        60
agccataatg taaactgcct caaattggac tttgggcata aagaagcttt accatctttt       120
ttttttcttt aacagatttg tatttaagaa ttgtttttaa aaaaatttta agatttacac       180
aatgtttctc tgtaaatatt gccataactt taataaaacg tttatagcag ttacacagaa       240
tttcaatcct agtatatagt acctagtatt ataggtacta taaaccctaa ttttttttat       300
ttaagtacat tttgtgattt ttttctattg tttttagaaa aataaaata actggcaaat        360
aaaaaaaaaa aaaaaaa                                                      378

<210> SEQ ID NO 106
<211> LENGTH: 326
<212> TYPE: DNA
<213> ORGANISM: Rodent

<400> SEQUENCE: 106
aaaatgcatg ctcaaagcct aacctcacaa ccttggctgg ggctttggga cttcagccat        60
aatgttaact gcctcaaagt taaggcataa aagaagcttc ccatcttctt tcttttttcct      120
ttaacagatt tgtatttaat tgtttttttt aaaaaatct tccggtgtac atagggcctt        180
aactttaata aaacgtttat aacagttata caagatttta agacatgtat gataaaccat       240
aattttttt atttaaagac cttttctgat tttttctat tgtttttaga aaaaataaaa         300
taattggaaa aaatataatt gagcca                                            326

<210> SEQ ID NO 107
<211> LENGTH: 326
<212> TYPE: DNA
<213> ORGANISM: Rodent

<400> SEQUENCE: 107
ttaaaatgca tgctcaaagc taacctcac aaccttggct ggggctttgg gactgtaagc         60
ttcagccata attttaactg cctcaaactt aaatagtata aagaagcttc ccatcttttt       120
ttcttttttcc ttttaacaga tttgtattta attgttttt taaaaaaatc taaaatctat       180
ccaatttttcc catgtaaata gggccttaac tttaataaaa cgtttataac agttacaaaa       240
gatttaaga catgtaccat aatttttttt atttaaagac attttctgat ttttttctat        300
tgttttaga aaaaataaa ataatt                                              326

<210> SEQ ID NO 108
<211> LENGTH: 24
<212> TYPE: RNA
<213> ORGANISM: Homo sapiens

<400> SEQUENCE: 108
aaugcaugau caaaugcaac cuca                                              24

<210> SEQ ID NO 109
<211> LENGTH: 22
<212> TYPE: RNA

```
<213> ORGANISM: Homo sapiens

<400> SEQUENCE: 109
agccauaaug uaaacugccu ca                                        22

<210> SEQ ID NO 110
<211> LENGTH: 21
<212> TYPE: RNA
<213> ORGANISM: Ceanorhabditis elegans

<400> SEQUENCE: 110
uuguauguug gaugauggag u                                         21
```